United States Patent [19]
Barry et al.

[11] Patent Number: 5,608,149
[45] Date of Patent: Mar. 4, 1997

[54] ENHANCED STARCH BIOSYNTHESIS IN TOMATOES

[75] Inventors: Gerard F. Barry, St. Louis; Ganesh M. Kishore, Chesterfield; David M. Stark, Fenton, all of Mo.

[73] Assignee: Monsanto Company, St. Louis, Mo.

[21] Appl. No.: 398,627

[22] Filed: Mar. 3, 1995

Related U.S. Application Data

[60] Division of Ser. No. 90,523, Jul. 12, 1993, Pat. No. 5,498,830, which is a continuation-in-part of Ser. No. 709,663, Jun. 7, 1991, abandoned, which is a continuation-in-part of Ser. No. 539,763, Jun. 18, 1990, abandoned.

[51] Int. Cl.$^6$ .............................. A01H 5/00; C12N 15/54; C12N 15/62; C12N 15/82; C12N 5/04
[52] U.S. Cl. .................. 800/205; 536/23.2; 536/23.4; 536/23.7; 536/24.1; 800/DIG. 44; 435/69.1; 435/70.1; 435/69.7; 435/69.8; 435/101; 435/172.3; 435/194; 435/411
[58] Field of Search ................... 536/23.2, 23.4, 536/23.7, 24.1; 435/69.1, 70.1, 69.7, 69.8, 172.3, 240.4, 101, 134, 194; 800/205, DIG. 17, 56–58, DIG. 44

[56] References Cited

U.S. PATENT DOCUMENTS 5,498,830  3/1996  Barry et al. .............................. 800/205

OTHER PUBLICATIONS

Anderson et al. 1990. pp. 159–180 In: Mol. Cell. Biol. Potato, Vayda et al., eds., C.A.B. International: Wallingford, U.K.

Meyer et al. 1993. Arch. Biochem. Biophys. 302(1): 64–71.

*Primary Examiner*—David T. Fox
*Attorney, Agent, or Firm*—Grace L. Bonner; Dennis R. Hoerner, Jr.

[57] ABSTRACT

Promoters for enhanced expression of ADPglucose pyrophosphorylase in potato tubers and fruits such as tomato; methods of using them; DNA molecules, plant cells and plants containing them. A method of decreasing the oil content of seeds by expression of ADPglucose pyrophosphorylase.

16 Claims, 22 Drawing Sheets

```
DNA    ATGGTTAGTTTAGAGAAGAACGATCACTTAATGTTGGCGCGCCAGCTGCCATTGAAATCT
     1 ---------|---------|---------|---------|---------|---------|
Protein M  V  S  L  E  K  N  D  H  L  M  L  A  R  Q  L  P  L  K  S GTTGCCCTGATACTGGCGGGAGGACGTGGTACCCGCCTGAAGGATTTAACCAATAAGCGA
    61 ---------|---------|---------|---------|---------|---------|
       V  A  L  I  L  A  G  G  R  G  T  R  L  K  D  L  T  N  K  R GCAAAACCGGCCGTACACTTCGGCGGTAAGTTCCGCATTATCGACTTTGCGCTGTCTAAC
   121 ---------|---------|---------|---------|---------|---------|
       A  K  P  A  V  H  F  G  G  K  F  R  I  I  D  F  A  L  S  N TGCATCAACTCCGGGATCCGTCGTATGGGCGTGATCACCCAGTACCAGTCCCACACTCTG
   181 ---------|---------|---------|---------|---------|---------|
       C  I  N  S  G  I  R  R  M  G  V  I  T  Q  Y  Q  S  H  T  L GTGCAGCACATTCAGCGCGGCTGGTCATTCTTCAATGAAGAAATGAACGAGTTTGTCGAT
   241 ---------|---------|---------|---------|---------|---------|
       V  Q  H  I  Q  R  G  W  S  F  F  N  E  E  M  N  E  F  V  D CTGCTGCCAGCACAGCAGAGAATGAAAGGGGAAAACTGGTATCGCGGCACCGCAGATGCG
   301 ---------|---------|---------|---------|---------|---------|
       L  L  P  A  Q  Q  R  M  K  G  E  N  W  Y  R  G  T  A  D  A GTCACCCAAAACCTCGACATTATCCGTCGTTATAAAGCGGAATACGTGGTGATCCTGGCG
   361 ---------|---------|---------|---------|---------|---------|
       V  T  Q  N  L  D  I  I  R  R  Y  K  A  E  Y  V  V  I  L  A GGCGACCATATCTACAAGCAAGACTACTCGCGTATGCTTATCGATCACGTCGAAAAAGGT
   421 ---------|---------|---------|---------|---------|---------|
       G  D  H  I  Y  K  Q  D  Y  S  R  M  L  I  D  H  V  E  K  G GTACGTTGTACCGTTGTTTGTATGCCAGTACCGATTGAAGAAGCCTCCGCATTTGGCGTT
   481 ---------|---------|---------|---------|---------|---------|
       V  R  C  T  V  V  C  M  P  V  P  I  E  E  A  S  A  F  G  V ATGGCGGTTGATGAGAACGATAAAACTATCGAATTCGTGGAAAAACCTGCTAACCCGCCG
   541 ---------|---------|---------|---------|---------|---------|
       M  A  V  D  E  N  D  K  T  I  E  F  V  E  K  P  A  N  P  P TCAATGCCGAACGATCCGAGCAAATCTCTGGCGAGTATGGGTATCTACGTCTTTGACGCC
   601 ---------|---------|---------|---------|---------|---------|
       S  M  P  N  D  P  S  K  S  L  A  S  M  G  I  Y  V  F  D  A GACTATCTGTATGAACTGCTGGAAGAAGACGATCGCGATGAGAACTCCAGCCACGACTTT
   661 ---------|---------|---------|---------|---------|---------|
       D  Y  L  Y  E  L  L  E  E  D  D  R  D  E  N  S  S  H  D  F
```

FIG. 1A

```
        GGCAAAGATTTGATTCCCAAGATCACCGAAGCCGGTCTGGCCTATGCGCACCCGTTCCCG
721     ----------|----------|----------|----------|----------|----------|
         G  K  D  L  I  P  K  I  T  E  A  G  L  A  Y  A  H  P  F  P

CTCTCTTGCGTACAATCCGACCCGGATGCCGAGCCGTACTGGCGCGATGTGGGTACGCTG
781     ----------|----------|----------|----------|----------|----------|
         L  S  C  V  Q  S  D  P  D  A  E  P  Y  W  R  D  V  G  T  L

GAAGCTTACTGGAAAGCGAACCTCGATCTGGCCTCTGTGGTGCCGAAACTGGATATGTAC
841     ----------|----------|----------|----------|----------|----------|
         E  A  Y  W  K  A  N  L  D  L  A  S  V  V  P  K  L  D  M  Y

GATCGCAATTGGCCAATTCGCACCTACAATGAATCATTACCGCCAGCGAAATTCGTGCAG
901     ----------|----------|----------|----------|----------|----------|
         D  R  N  W  P  I  R  T  Y  N  E  S  L  P  P  A  K  F  V  Q

GATCGCTCCGGTAGCCACGGGATGACCCTTAACTCACTGGTTTCCGGCGGTTGTGTGATC
961     ----------|----------|----------|----------|----------|----------|
         D  R  S  G  S  H  G  M  T  L  N  S  L  V  S  G  G  C  V  I

TCCGGTTCGGTGGTGGTGCAGTCCGTTCTGTTCTCGCGCGTTCGCGTGAATTCATTCTGC
1021    ----------|----------|----------|----------|----------|----------|
         S  G  S  V  V  V  Q  S  V  L  F  S  R  V  R  V  N  S  F  C

AACATTGATTCCGCCGTATTGTTACCGGAAGTATGGGTAGGTCGCTCGTGCCGTCTGCGC
1081    ----------|----------|----------|----------|----------|----------|
         N  I  D  S  A  V  L  L  P  E  V  W  V  G  R  S  C  R  L  R

CGCTGCGTCATCGATCGTGCTTGTGTTATTCCGGAAGGCATGGTGATTGGTGAAAACGCA
1141    ----------|----------|----------|----------|----------|----------|
         R  C  V  I  D  R  A  C  V  I  P  E  G  M  V  I  G  E  N  A

GAGGAAGATGCACGTCGTTTCTATCGTTCAGAAGAAGGCATCGTGCTGGTAACGCGCGAA
1201    ----------|----------|----------|----------|----------|----------|
         E  E  D  A  R  R  F  Y  R  S  E  E  G  I  V  L  V  T  R  E

ATGCTACGGAAGTTAGGGCATAAACAGGAGCGATAA
1261    ----------|----------|----------|------
         M  L  R  K  L  G  H  K  Q  E  R  *
```

FIG. 1B

```
DNA      ATGGTTAGTTTAGAGAAGAACGATCACTTAATGTTGGCGCGCCAGCTGCCATTGAAATCT
      1  ----------|----------|----------|----------|----------|----------|
Protein  M  V  S  L  E  K  N  D  H  L  M  L  A  R  Q  L  P  L  K  S GTTGCCCTGATACTGGCGGGAGGACGTGGTACCCGCCTGAAGGATTTAACCAATAAGCGA
      61 ----------|----------|----------|----------|----------|----------|
         V  A  L  I  L  A  G  G  R  G  T  R  L  K  D  L  T  N  K  R GCAAAACCGGCCGTACACTTCGGCGGTAAGTTCCGCATTATCGACTTTGCGCTGTCTAAC
     121 ----------|----------|----------|----------|----------|----------|
         A  K  P  A  V  H  F  G  G  K  F  R  I  I  D  F  A  L  S  N TGCATCAACTCCGGGATCCGTCGTATGGGCGTGATCACCCAGTACCAGTCCCACACTCTG
     181 ----------|----------|----------|----------|----------|----------|
         C  I  N  S  G  I  R  R  M  G  V  I  T  Q  Y  Q  S  H  T  L GTGCAGCACATTCAGCGCGGCTGGTCATTCTTCAATGAAGAAATGAACGAGTTTGTCGAT
     241 ----------|----------|----------|----------|----------|----------|
         V  Q  H  I  Q  R  G  W  S  F  F  N  E  E  M  N  E  F  V  D CTGCTGCCAGCACAGCAGAGAATGAAAGGGGAAAACTGGTATCGCGGCACCGCAGATGCG
     301 ----------|----------|----------|----------|----------|----------|
         L  L  P  A  Q  Q  R  M  K  G  E  N  W  Y  R  G  T  A  D  A GTCACCCAAAACCTCGACATTATCCGTCGTTATAAAGCGGAATACGTGGTGATCCTGGCG
     361 ----------|----------|----------|----------|----------|----------|
         V  T  Q  N  L  D  I  I  R  R  Y  K  A  E  Y  V  V  I  L  A GGCGACCATATCTACAAGCAAGACTACTCGCGTATGCTTATCGATCACGTCGAAAAAGGT
     421 ----------|----------|----------|----------|----------|----------|
         G  D  H  I  Y  K  Q  D  Y  S  R  M  L  I  D  H  V  E  K  G GTACGTTGTACCGTTGTTTGTATGCCAGTACCGATTGAAGAAGCCTCCGCATTTGGCGTT
     481 ----------|----------|----------|----------|----------|----------|
         V  R  C  T  V  V  C  M  P  V  P  I  E  E  A  S  A  F  G  V ATGGCGGTTGATGAGAACGATAAAACTATCGAATTCGTGGAAAAACCGCTAACCCGCCG
     541 ----------|----------|----------|----------|----------|----------|
         M  A  V  D  E  N  D  K  T  I  E  F  V  E  K  P  A  N  P  P TCAATGCCGAACGATCCGAGCAAATCTCTGGCGAGTATGGGTATCTACGTCTTTGACGCC
     601 ----------|----------|----------|----------|----------|----------|
         S  M  P  N  D  P  S  K  S  L  A  S  M  G  I  Y  V  F  D  A GACTATCTGTATGAACTGCTGGAAGAAGACGATCGCGATGAGAACTCCAGCCACGACTTT
     661 ----------|----------|----------|----------|----------|----------|
         D  Y  L  Y  E  L  L  E  E  D  D  R  D  E  N  S  S  H  D  F GGCAAAGATTTGATTCCCAAGATCACCGAAGCCGGTCTGGCCTATGCGCACCCGTTCCCG
     721 ----------|----------|----------|----------|----------|----------|
         G  K  D  L  I  P  K  I  T  E  A  G  L  A  Y  A  H  P  F  P
```

FIG. 2A

```
     CTCTCTTGCGTACAATCCGACCCGGATGCCGAGCCGTACTGGCGCGATGTGGGTACGCTG
781  ---------|---------|---------|---------|---------|---------|
      L  S  C  V  Q  S  D  P  D  A  E  P  Y  W  R  D  V  G  T  L

GAAGCTTACTGGAAAGCGAACCTCGATCTGGCCTCTGTGGTGCCGGAACTGGATATGTAC
841  ---------|---------|---------|---------|---------|---------|
      E  A  Y  W  K  A  N  L  D  L  A  S  V  V  P  E  L  D  M  Y

GATCGCAATTGGCCAATTCGCACCTACAATGAATCATTACCGCCAGCGAAATTCGTGCAG
901  ---------|---------|---------|---------|---------|---------|
      D  R  N  W  P  I  R  T  Y  N  E  S  L  P  P  A  K  F  V  Q

GATCGCTCCGGTAGCCACGGGATGACCCTTAACTCACTGGTTTCCGACGGTTGTGTGATC
961  ---------|---------|---------|---------|---------|---------|
      D  R  S  G  S  H  G  M  T  L  N  S  L  V  S  D  G  C  V  I

TCCGGTTCGGTGGTGGTGCAGTCCGTTCTGTTCTCGCGCGTTCGCGTGAATTCATTCTGC
1021 ---------|---------|---------|---------|---------|---------|
      S  G  S  V  V  V  Q  S  V  L  F  S  R  V  R  V  N  S  F  C

AACATTGATTCCGCCGTATTGTTACCGGAAGTATGGGTAGGTCGCTCGTGCCGTCTGCGC
1081 ---------|---------|---------|---------|---------|---------|
      N  I  D  S  A  V  L  L  P  E  V  W  V  G  R  S  C  R  L  R

CGCTGCGTCATCGATCGTGCTTGTGTTATTCCGGAAGGCATGGTGATTGGTGAAAACGCA
1141 ---------|---------|---------|---------|---------|---------|
      R  C  V  I  D  R  A  C  V  I  P  E  G  M  V  I  G  E  N  A

GAGGAAGATGCACGTCGTTTCTATCGTTCAGAAGAAGGCATCGTGCTGGTAACGCGCGAA
1201 ---------|---------|---------|---------|---------|---------|
      E  E  D  A  R  R  F  Y  R  S  E  E  G  I  V  L  V  T  R  E

ATGCTACGGAAGTTAGGGCATAAACAGGAGCGATAA
1261 ---------|---------|---------|------
      M  L  R  K  L  G  H  K  Q  E  R  *
```

FIG. 2B

```
H
i
n
d
I
I
I
aagcttgttctcattgttgttatcattatatatagatgaccaaagcactagaccaaacct
1 ---------|---------|---------|---------|---------|---------| 60 cagtcacacaaagagtaaagaagaacaatggcttcctctatgctctcttccgctactatg
61 ---------|---------|---------|---------|---------|---------| 120
                              M  A  S  S  M  L  S  S  A  T  M gttgcctctccggctcaggccactatggtcgctcctttcaacggacttaagtcctccgct
121 ---------|---------|---------|---------|---------|---------| 180
V  A  S  P  A  Q  A  T  M  V  A  P  F  N  G  L  K  S  S  A gccttcccagccacccgcaaggctaacaacgacattacttccatcacaagcaacggcgga
181 ---------|---------|---------|---------|---------|---------| 240
A  F  P  A  T  R  K  A  N  N  D  I  T  S  I  T  S  N  G  G agagttaactgcatgcaggtgtggcctccgattggaaagaagaagtttgagactctctct
241 ---------|---------|---------|---------|---------|---------| 300
R  V  N  C  M  Q  V  W  P  P  I  G  K  K  K  F  E  T  L  S
                                                          N
                                                          c
                                                          o
                                                          I
taccttcctgaccttaccgattccggtggtcgcgtcaactgcatgcaggccatgg
301 ---------|---------|---------|---------|---------|----- 355
Y  L  P  D  L  T  D  S  G  G  R  V  N  C  M  Q  A  M
```

FIG. 3

```
  1 CCATGGCGGCTTCCATTGGAGCCTTAAAATCTTCACCTTCTTCTAACAATTGCATCAATG   60
    MetAlaAlaSerIleGlyAlaLeuLysSerSerProSerSerAsnAsnCysIleAsnG
 61 AGAGAAGAAATGATTCTACACGTGCTGTATCCAGCAGAAATCTCTCATTTTCGTCTTCTC  120
    luArgArgAsnAspSerThrArgAlaValSerSerArgAsnLeuSerPheSerSerSerH
121 ATCTCGCCGGAGACAAGTTGATGCCTGTATCGTCCTTACGTTCCCAAGGAGTCCGATTCA  180
    isLeuAlaGlyAspLysLeuMetProValSerSerLeuArgSerGlnGlyValArgPheA
181 ATGTGAGAAGAAGTCCAATGATTGTGTCGCCAAAGGCTGTTTCTGATTCGCAGAATTCAC  240
    snValArgArgSerProMetIleValSerProLysAlaValSerAspSerGlnAsnSerG
241 AGACATGTCTAGACCCAGATGCTAGCCGGAGTGTTTTGGGAATTATTCTTGGAGGTGGAG  300
    lnThrCysLeuAspProAspAlaSerArgSerValLeuGlyIleIleLeuGlyGlyGlyA
301 CTGGGACCCGACTTTATCCTCTAACTAAAAAAAGAGCAAAGCCAGCTGTTCCACTTGGAG  360
    laGlyThrArgLeuTyrProLeuThrLysLysArgAlaLysProAlaValProLeuGlyA
361 CAAATTATCGTCTGATTGACATTCCTGTAAGCAACTGCTTGAACAGTAATATATCCAAGA  420
    laAsnTyrArgLeuIleAspIleProValSerAsnCysLeuAsnSerAsnIleSerLysI
421 TTTATGTTCTCACACAATTCAACTCTGCCTCTCTGAATCGCCACCTTTCACGAGCATATG  480
    leTyrValLeuThrGlnPheAsnSerAlaSerLeuAsnArgHisLeuSerArgAlaTyrA
481 CTAGCAACATGGGAGGATACAAAAACGAGGGCTTTGTGGAAGTTCTTGCTGCTCAACAAA  540
    laSerAsnMetGlyGlyTyrLysAsnGluGlyPheValGluValLeuAlaAlaGlnGlnS
541 GTCCAGAGAACCCCGATTGGTTCCAGGGCACGGCTGATGCTGTCAGACAATATCTGTGGT  600
    erProGluAsnProAspTrpPheGlnGlyThrAlaAspAlaValArgGlnTyrLeuTrpL
601 TGTTTGAGGAGCATACTGTTCTTGAATACCTTATACTTGCTGGAGATCATCTGTATCGAA  660
    euPheGluGluHisThrValLeuGluTyrLeuIleLeuAlaGlyAspHisLeuTyrArgM
661 TGGATTATGAAAAGTTTATTCAAGCCCACAGAGAAACAGATGCTGATATTACCGTTGCCG  720
    etAspTyrGluLysPheIleGlnAlaHisArgGluThrAspAlaAspIleThrValAlaA
721 CACTGCCAATGGACGAGAAGCGTGCCACTGCATTCGGTCTCATGAAGATTGACGAAGAAG  780
    laLeuProMetAspGluLysArgAlaThrAlaPheGlyLeuMetLysIleAspGluGluG
781 GACGCATTATTGAATTTGCAGAGAAACCGCAAGGAGAGCAATTGCAAGCAATGAAAGTGG  840
    lyArgIleIleGluPheAlaGluLysProGlnGlyGluGlnLeuGlnAlaMetLysValA
```

FIG.5A

```
 841 ATACTACCATTTTAGGTCTTGATGACAAGAGAGCTAAAGAAATGCCTTTCATTGCCAGTA  900
     spThrThrIleLeuGlyLeuAspAspLysArgAlaLysGluMetProPheIleAlaSerM
 901 TGGGTATATATGTCATTAGCAAAGACGTGATGTTAAACCTACTTCGTGACAAGTTCCCTG  960
     etGlyIleTyrValIleSerLysAspValMetLeuAsnLeuLeuArgAspLysPheProG
 961 GGGCCAATGATTTTGGTAGTGAAGTTATTCCTGGTGCAACTTCACTTGGGATGAGAGTGC 1020
     lyAlaAsnAspPheGlySerGluValIleProGlyAlaThrSerLeuGlyMetArgValG
1021 AAGCTTATTTATATGATGGGTACTGGGAAGATATTGGTACCATTGAAGCTTTCTACAATG 1080
     lnAlaTyrLeuTyrAspGlyTyrTrpGluAspIleGlyThrIleGluAlaPheTyrAsnA
1081 CCAATTTGGGCATTACAAAAAAGCCGGTGCCAGATTTTAGCTTTTACGACCGATCAGCCC 1140
     laAsnLeuGlyIleThrLysLysProValProAspPheSerPheTyrAspArgSerAlaP
1141 CAATCTACACCCAACCTCGATATCTACCACCATCAAAAATGCTTGATGCTGATGTCACAG 1200
     roIleTyrThrGlnProArgTyrLeuProProSerLysMetLeuAspAlaAspValThrA
1201 ATAGTGTCATTGGTGAAGGTTGTGTGATCAAGAACTGTAAGATTCATCATTCCGTGGTTG 1260
     spSerValIleGlyGluGlyCysValIleLysAsnCysLysIleHisHisSerValValG
1261 GACTCAGATCATGCATATCAGAGGGAGCAATTATAGAAGACTCACTTTTGATGGGGGCAG 1320
     lyLeuArgSerCysIleSerGluGlyAlaIleIleGluAspSerLeuLeuMetGlyAlaA
1321 ATTACTATGAGACTGATGCTGACAGGAAGTTGCTGGCTGCAAAGGGCAGTGTCCCAATTG 1380
     spTyrTyrGluThrAspAlaAspArgLysLeuLeuAlaAlaLysGlySerValProIleG
1381 GCATCGGCAAGAATTGTCACATTAAAAGAGCCATTATCGACAAGAATGCCCGTATAGGGG 1440
     lyIleGlyLysAsnCysHisIleLysArgAlaIleIleAspLysAsnAlaArgIleGlyA
1441 ACAATGTGAAGATCATTAACAAAGACAACGTTCAAGAAGCGGCTAGGGAAACAGATGGAT 1500
     spAsnValLysIleIleAsnLysAspAsnValGlnGluAlaAlaArgGluThrAspGlyT
1501 ACTTCATCAAGAGTGGGATTGTCACCGTCATCAAGGATGCTTTGATTCCAAGTGGAATCA 1560
     yrPheIleLysSerGlyIleValThrValIleLysAspAlaLeuIleProSerGlyIleI
1561 TCATCTGATGAGCTC 1575
     leIleEndEnd
```

FIG.5B

```
  1 AACAAGATCAAACCTGGGGTTGCTTACTCTGTGATCACTACTGAAAATGACACACAGACT   60
    AsnLysIleLysProGlyValAlaTyrSerValIleThrThrGluAsnAspThrGlnThr
 61 GTGTTCGTAGATATGCCACGTCTTGAGAGACGCCGGGCAAATCCAAAGGATGTGGCTGCA  120
    ValPheValAspMetProArgLeuGluArgArgArgAlaAsnProLysAspValAlaAla
121 GTCATACTGGGAGGAGGAGAAGGGACCAAGTTATTCCCACTTACAAGTAGAACTGCAACC  180
    ValIleLeuGlyGlyGlyGluGlyThrLysLeuPheProLeuThrSerArgThrAlaThr
181 CCTGCTGTTCCGGTTGGAGGATGCTACAGGCTAATAGACATCCCAATGAGCAACTGTATC  240
    ProAlaValProValGlyGlyCysTyrArgLeuIleAspIleProMetSerAsnCysIle
241 AACAGTGCTATTAACAAGATTTTTGTGCTGACACAGTACAATTCTGCTCCCCTGAATCGT  300
    AsnSerAlaIleAsnLysIlePheValLeuThrGlnTyrAsnSerAlaProLeuAsnArg
301 CACATTGCTCGAACATATTTTGGCAATGGTGTGAGCTTTGGAGATGGATTTGTCGAGGTA  360
    HisIleAlaArgThrTyrPheGlyAsnGlyValSerPheGlyAspGlyPheValGluVal
361 CTAGCTGCAACTCAGACACCCGGGGAAGCAGGAAAAAAATGGTTTCAAGGAACAGCAGAT  420
    LeuAlaAlaThrGlnThrProGlyGluAlaGlyLysLysTrpPheGlnGlyThrAlaAsp
421 GCTGTTAGAAAATTTATATGGGTTTTTGAGGACGCTAAGAACAAGAATATTGAAAATATC  480
    AlaValArgLysPheIleTrpValPheGluAspAlaLysAsnLysAsnIleGluAsnIle
481 GTTGTACTATCTGGGGATCATCTTTATAGGATGGATTATATGGAGTTGGTGCAGAACCAT  540
    ValValLeuSerGlyAspHisLeuTyrArgMetAspTyrMetGluLeuValGlnAsnHis
541 ATTGACAGGAATGCTGATATTACTCTTTCATGTGCACCAGCTGAGGACAGCCGAGCATCA  600
    IleAspArgAsnAlaAspIleThrLeuSerCysAlaProAlaGluAspSerArgAlaSer
601 GATTTTGGGCTGGTCAAGATTGACAGCAGAGGCAGAGTAGTCCAGTTTGCTGAAAAACCA  660
    AspPheGlyLeuValLysIleAspSerArgGlyArgValValGlnPheAlaGluLysPro
661 AAAGGTTTTGATCTTAAAGCAATGCAAGTAGATACTACTCTTGTTGGATTATCTCCACAA  720
    LysGlyPheAspLeuLysAlaMetGlnValAspThrThrLeuValGlyLeuSerProGln
```

FIG.6A

```
721  GATGCGAAGAAATCCCCCTATATTGCTTCAATGGGAGTTTATGTATTCAAGACAGATGTA  780
     AspAlaLysLysSerProTyrIleAlaSerMetGlyValTyrValPheLysThrAspVal
781  TTGTTGAAGCTCTTGAAATGGAGCTATCCCACTTCTAATGATTTTGGCTCTGAAATTATA  840
     LeuLeuLysLeuLeuLysTrpSerTyrProThrSerAsnAspPheGlySerGluIleIle
841  CCAGCAGCTATTGACGATTACAATGTCCAAGCATACATTTTCAAAGACTATTGGGAAGAC  900
     ProAlaAlaIleAspAspTyrAsnValGlnAlaTyrIlePheLysAspTyrTrpGluAsp
901  ATTGGAACAATTAAATCGTTTTATAATGCTAGCTTGGCACTCACACAAGAGTTTCCAGAG  960
     IleGlyThrIleLysSerPheTyrAsnAlaSerLeuAlaLeuThrGlnGluPheProGlu
961  TTCCAATTTTACGATCCAAAAACACCTTTTTACACATCTCCTAGGTTCCTTCCACCAACC  1020
     PheGlnPheTyrAspProLysThrProPheTyrThrSerProArgPheLeuProProThr
1021 AAGATAGACAATTGCAAGATTAAGGATGCCATAATCTCTCATGGATGTTTCTTGCGAGAT  1080
     LysIleAspAsnCysLysIleLysAspAlaIleIleSerHisGlyCysPheLeuArgAsp
1081 TGTTCTGTGGAACACTCCATAGTGGGTGAAAGATCGCGCTTAGATTGTGGTGTTGAACTG  1140
     CysSerValGluHisSerIleValGlyGluArgSerArgLeuAspCysGlyValGluLeu
1141 AAGGATACTTTCATGATGGGAGCAGACTACTACCAAACAGAATCTGAGATTGCCTCCCTG  1200
     LysAspThrPheMetMetGlyAlaAspTyrTyrGlnThrGluSerGluIleAlaSerLeu
1201 TTAGCAGAGGGGAAAGTACCGATTGGAATTGGGGAAAATACAAAAATAAGGAAATGTATC  1260
     LeuAlaGluGlyLysValProIleGlyIleGlyGluAsnThrLysIleArgLysCysIle
1261 ATTGACAAGAACGCAAAGATAGGAAAGAATGTTTCAATCATAAATAAAGACGGTGTTCAA  1320
     IleAspLysAsnAlaLysIleGlyLysAsnValSerIleIleAsnLysAspGlyValGln
1321 GAGGCAGACCGACCAGAGGAAGGATTCTACATACGATCAGGGATAATCATTATATTAGAG  1380
     GluAlaAspArgProGluGluGlyPheTyrIleArgSerGlyIleIleIleIleLeuGlu
1381 AAAGCCACAATTAGAGATGGAACAGTCATCTGAACTAGGGAAGCACCTCTTGTTGAACTA  1440
     LysAlaThrIleArgAspGlyThrValIleEnd
1441 CTGGAGATCCAAATCTCAACTTGAAGAAGGTCAAGGGTGATCCTAGCACGTTCACCAGTT  1500
1501 GACTCCCCGAAGGAAGCTT  1519
```

FIG.6B

ENHANCED STARCH BIOSYNTHESIS IN TOMATOES

This is a divisional application of U.S. Ser. No. 08/090,523, filed Jul. 12, 1993, now U.S. Pat. No. 5,498,830, which was a continuation-in-part of a U.S. application having Ser. No. 07/709,663, filed on Jun. 7, 1991, now abandoned, which was a continuation-in-part of U.S. application having Ser. No. 07/539,763, filed on Jun. 18, 1990, now abandoned.

BACKGROUND OF THE INVENTION

Recent advances in genetic engineering have provided the requisite tools to transform plants to contain foreign genes. It is now possible to produce plants which have unique characteristics of agronomic and crop processing importance. Certainly, one such advantageous trait is enhanced starch and/or solids content and quality in various crop plants.

Starch is a polysaccharide primarily composed of glucose units connected by alpha 1–4 and alpha 1–6 linkages. It is found in plant cells as water-insoluble grains or granules. During photosynthesis, starch is produced and stored in chloroplasts. Starch is also synthesized in roots and storage organs such as tubers and seeds. In these non-photosynthetic tissues, the starch is found in a form of plastids called amyloplasts. As in the chloroplasts, starch is stored in the amyloplasts as starch granules. The size of the granules varies depending on the plant species.

Starch is actually composed of amylose and amylopectin, two distinct types of glucose polymers. Amylose is composed primarily of linear chains of alpha 1–4 linked glucose molecules. On average, amylose has a chain length of about 1000 glucose molecules. Amylopectin contains shorter chains linked together with alpha 1–6 linkages. On average, amylopectin has a chain length of about 20–25 glucose molecules.

Until recently, there was controversy in the literature as to whether ADPglucose or UDPglucose was the substrate for starch synthesis. With the isolation of Arabidopsis mutants lacking ADPglucose pyrophosphorylase it is now accepted that plants use ADPglucose as the substrate for starch synthesis. There are three steps in the synthesis of starch. All these reactions take place within the chloroplasts or amyloplasts. In the first step, ADPglucose is produced from glucose-1-phosphate and ATP by ADPglucose pyrophosphorylase (EC 2.7.7.27). In the second step, ADPglucose is used by starch synthase (EC 2.4.1.21) to form linear chains of starch containing the alpha 1–4 linkage. In the third step, the branching enzyme(s) (EC 2.4.1.18) introduce alpha 1–6 linkages to produce the amylopectin molecule.

The controlling step in the synthesis of starch in plants has been a topic of dispute. Although synthesis of ADPglucose by ADPglucose pyrophosphorylase has been proposed to be the controlling step in starch biosynthesis, this has not been proved. In fact, European Patent Application publication number 0368506 A2, which concerns ADPglucose pyrophosphorylase, questions the role of the enzyme as the rate limiting step in starch biosynthesis. An argument against ADPglucose pyrophosphorylase being the controlling enzyme can be made from the results with an Arabidopsis mutant (Lin, 1988a,b). This mutant, TL46, was found to contain only about 5% of the ADPglucose pyrophosphorylase activity compared to the wild type plants. However, TL46 plants still produced about 40% of the wild type starch levels. If ADPglucose pyrophosphorylase is the rate limiting enzyme, one would have expected a 95% reduction in enzyme activity to produce more than a 60% reduction in starch accumulation. Similarly, the in vitro measurements on extractable activities suggest this enzyme can only be rate limiting if its in vivo activity is substantially inhibited by the allosteric regulators of the enzyme activity.

SUMMARY OF THE INVENTION

The present invention provides structural DNA constructs which encode an ADPglucose pyrophosphorylase (ADPGPP) enzyme and which are useful in producing enhanced starch content in potato and tomato plants. In another aspect of the present invention, seeds having a reduced oil content as a result of enhanced ADPGPP expression are provided, as well as the DNA constructs useful in producing such seeds.

In accomplishing the foregoing, there is provided, in accordance with one aspect of the present invention, a method of producing genetically transformed plants which have elevated starch content, comprising the steps of:

(a) inserting into the genome of a plant cell a recombinant, double-stranded DNA molecule comprising
   (i) a promoter which for potato plants is selected from the group consisting of patatin promoters, large subunit potato ADPGPP promoter, small subunit potato ADPGPP, and granule-bound starch synthase promoter; and for tomato plants is selected from green fruit promoters,
   (ii) a structural DNA sequence that causes the production of an RNA sequence which encodes a fusion polypeptide comprising an amino-terminal plastid transit peptide and an ADPglucose pyrophosphorylase enzyme,
   (iii) a 3' non-translated DNA sequence which functions in plant cells to cause transcriptional termination and the addition of polyadenylated nucleotides to the 3' end of the RNA sequence;

(b) obtaining transformed plant cells; and (c) regenerating from the transformed plant cells genetically transformed plants which have an elevated starch content.

In accordance with another aspect of the present invention, there is provided a recombinant, double-stranded DNA molecule comprising in sequence:

(a) a promoter for potato plants is selected from the group consisting of patatin promoters, large subunit potato ADPGPP promoter, small subunit potato ADPGPP, and granule-bound starch synthase promoter; and for tomato plants is selected from green fruit promoters;

(b) a structural DNA sequence that causes the production of an RNA sequence which encodes a fusion polypeptide comprising an amino-terminal plastid transit peptide and an ADPglucose pyrophosphorylase enzyme; and (c) a 3' non-translated region which functions in plant cells to cause transcriptional termination and the addition of polyadenylated nucleotides to the 3' end of the RNA sequence, said promoter being heterologous with respect to the structural DNA.

There has also been provided, in accordance with another aspect of the present invention, transformed plant cells that contain DNA comprised of the above-mentioned elements (a), (b) and (c). In accordance with yet another aspect of the present invention, differentiated potato, tomato, and cereal plants are provided that have increased starch content in the tubers, fruit and seeds, respectively, and differentiated oil-seed crop plants are provided that have decreased oil content in the seeds.

BRIEF DESCRIPTION OF THE DRAWINGS

FIG. 1 shows the nucleotide sequence (SEQ ID NO:1) and deduced amino acid sequence (SEQ ID NO:2) for the ADPglucose pyrophosphorylase (glgC) gene from *E. coli*.

FIG. 2 shows the nucleotide sequence (SEQ ID NO:3) and deduced amino acid sequence (SEQ ID NO:4) for the mutant ADPglucose pyrophosphorylase (glgC16) gene from *E. coli*.

FIG. 3 shows the nucleotide sequence (SEQ ID NO:5) and corresponding amino acid sequence (SEQ ID NO:6) for the modified chloroplast transit peptide from the ssRUBISCO 1A gene from *Arabidopsis thaliana*.

FIG. 5 shows the nucleotide sequence (SEQ ID NO:7) and the corresponding amino acid sequence (SEQ ID NO:8) of the assembled small subunit ADPglucose pyrophosphorylase gene of potato.

FIG. 6 shows the near full length nucleotide sequence (SEQ ID NO:9) and the corresponding amino acid sequence (SEQ ID NO: 10) of the almost complete large subunit ADPglucose pyrophosphorylase gene of potato.

DETAILED DESCRIPTION OF THE INVENTION

Figure 4:
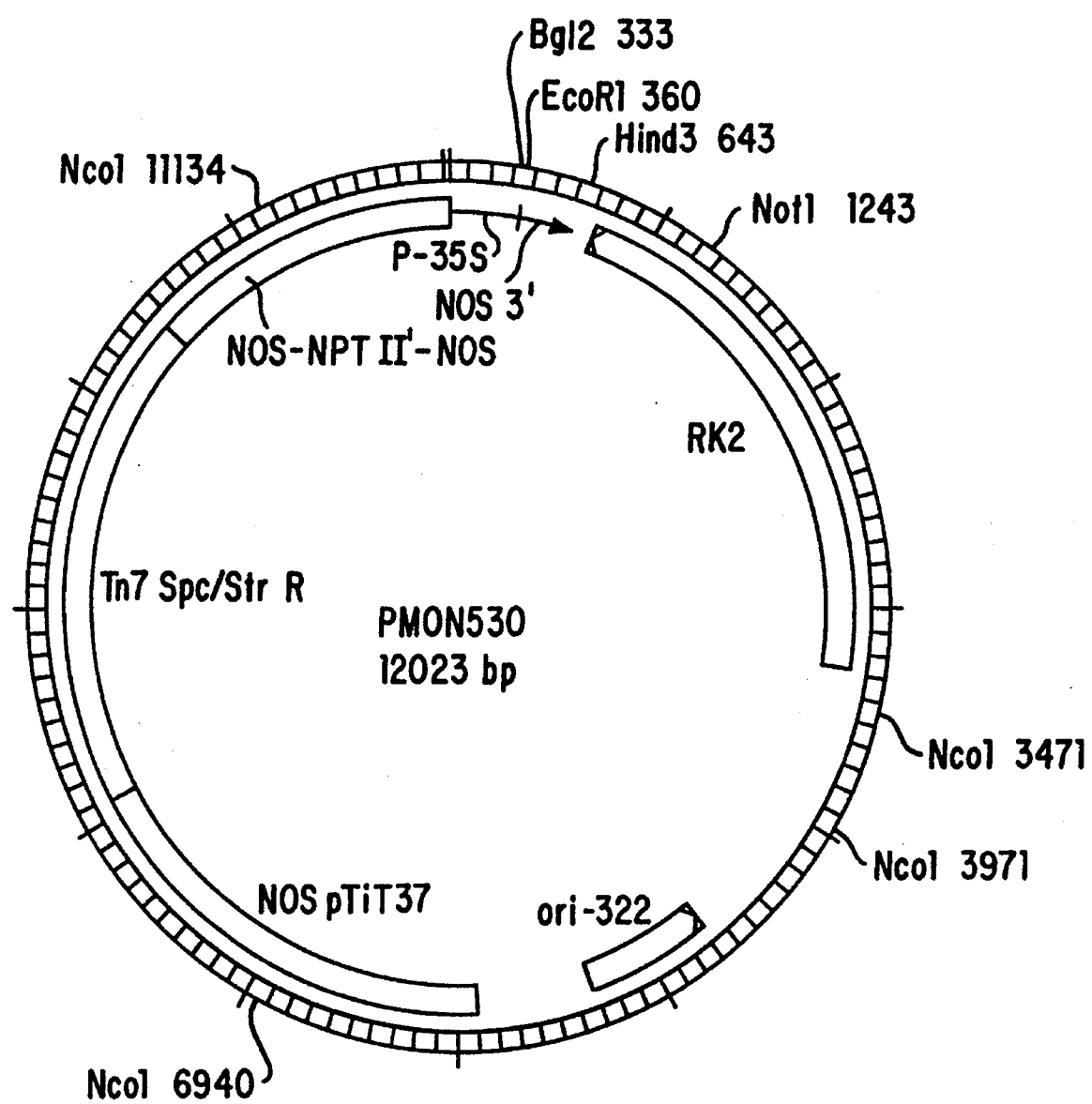
FIG. 4 shows a plasmid map for plant transformation vector pMON530.

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Transcription of DNA into mRNA is regulated by a region of DNA usually referred to as the promoter. The promoter region contains a sequence of bases that signals RNA polymerase to associate with the DNA, and to initiate the transcription of mRNA using one of the DNA strands as a template to make a corresponding complimentary strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter, etc. All of these promoters have been used to create various types of DNA constructs which have been expressed in plants; see, e.g., PCT publication WO 84/02913 (Rogers et al., Monsanto).

Promoters which are known or are found to cause transcription of DNA in plant cells can be used in the present invention. Such promoters may be obtained from a variety of sources such as plants and plant viruses and include, but are not limited to, the enhanced CaMV35S promoter and promoters isolated from plant genes such as ssRUBISCO genes. As described below, it is preferred that the particular promoter selected should be capable of causing sufficient expression to result in the production of an effective amount of ADPglucose pyrophosphorylase enzyme to cause the desired increase in starch content. In addition, it is preferred to bring about expression of the ADPGPP gene in specific tissues of the plant such as leaf, root, tuber, seed, fruit, etc. and the promoter chosen should have the desired tissue and developmental specificity. Those skilled in the art will recognize that the amount of ADPglucose pyrophosphorylase needed to induce the desired increase in starch content may vary with the type of plant and furthermore that too much ADPglucose pyrophosphorylase activity may be deleterious to the plant. Therefore, promoter function should be optimized by selecting a promoter with the desired tissue expression capabilities and approximate promoter strength and selecting a transformant which produces the desired ADPglucose pyrophosphorylase activity in the target tissues. This selection approach from the pool of transformants is routinely employed in expression of heterologous structural genes in plants since there is variation between transformants containing the same heterologous gene due to the site of gene insertion within the plant genome. (Commonly referred to as "position effect").

It is preferred that the promoters utilized in the double-stranded DNA molecules of the present invention have relatively high expression in tissues where the increased starch content and/or dry matter is desired, such as the tuber of the potato plant and the fruit of tomato. Expression of the double-stranded DNA molecules of the present invention by a constitutive promoter, expressing the DNA molecule in all or most of the tissues of the plant, will be rarely preferred and may, in some instances, be detrimental to plant growth.

The class I patatin promoter, used in Example 3 to express the *E. coli* ADPGPP, has been shown to be both highly active and tuber-specific (Bevan et al., 1986; Jefferson et al., 1990 ). A number of other genes with tuber-specific or -enhanced expression are known, including the potato tuber ADPGPP genes, both the large and small subunits, (Muller et al., 1990), sucrose synthase (Salanoubat and Belliard, 1987, 1989), the major tuber proteins including the 22 kd protein complexes and proteinase inhibitors (Hannapel, 1990), the granule bound starch synthase gene (GBSS) (Rohde et al., 1990), and the other class I and II patatins (Rocha-Sosa et al., 1989; Mignery et al., 1988). Other promoters which are contemplated to be useful in this invention include those that show enhanced or specific expression in potato tubers, that are promoters normally associated with the expression of starch biosynthetic or modification enzyme genes, or that show different patterns of expression within the potato tuber. Examples of these promoters include those for the genes for the granule-bound and other starch synthases, the branching enzymes (Kossmann et al., 1991; Blennow, A. and Johansson, G., 1991; WO 92/14827; WO 92/11375), diproportionating enzyme (Takaha et al., 1993), debranching enzymes, amylases, starch phosphorylases (Nakano et al., 1989; Mori et al., 1991), pectin esterases (Ebbelaar, et al., 1993), the 40 kD glycoprotein, ubiquitin, aspartic proteinase inhibitor (Stukerlj et al., 1990), the carboxypeptidase inhibitor, tuber polyphenol oxidases (Shahar et al., 1992; GenBank® Accession Numbers M95196 and M95197), putative trypsin inhibitor and other tuber cDNAs (Stiekema et al., 1988), and for β-amylase and sporamins (from *Ipomoea batatas;* Yoshida et al., 1992; Ohta et al., 1991).

In addition, promoters may be identified to be tuber specific by screening a cDNA library of potato for genes which are selectively or preferably expressed in tubers and then determine the promoter regions to obtain tuber selective or tuber-enhanced promoters. Twenty-two such cDNAs have been identified and the sequences are included below as SEQ ID NO:30 through SEQ ID NO:51. These sequences were identified by screening for novel tuber-specific cDNAs by a differential hybridization screening of a potato cDNA library. Independent cDNA clones were isolated on the basis of their preferential hybridization to tuber cDNA and not to shoot cDNA or to a patatin class 1 cDNA clone. Clones with homologies to several known genes (proteinase inhibitor II and 22 kD trypsin inhibitor) are not included. Partial sequence characterization of the cDNA clones reveals no homology to other sequences in the data banks and thus they are likely to represent a new set of genes and the promoters are therefore likely to be previously unknown.

In addition to the endogenous plant ADPglucose pyrophosphorylase promoters, other promoters can also be used to express an ADPglucose pyrophosphorylase gene in specific tissues, such as leaves, seeds or fruits. β-conglycinin (also known as the 7S protein) is one of the major storage proteins in soybean (*Glycine max*) (Tierney, 1987). The promoter for β-conglycinin or other seed-specific promoters can be used to over-express the *E. coli,* or any other, ADPglucose pyrophosphorylase gene specifically in seeds. This would lead to an increase in the starch content of the seeds and a decreased oil content, which would be desirable in seeds used for food, such as snacks, or for further processing, especially for foods prepared by fermentation of seed or its extracts where increased starch and reduced lipid could be substrates for the process or could enhance the extraction, such as tofu, soy sauce, miso, and natto. The β-subunit of β-conglycinin has been expressed, using its endogenous promoter, in the seeds of transgenic petunia and tobacco, showing that the promoter functions in a seed-specific manner in other plants (Bray, 1987). Example 7 below demonstrates the use of this type of promoter with an ADPglucose pyrophosphorylase in canola.

The zeins are a group of storage proteins found in maize endosperm. Genomic clones for zein genes have been isolated (Pedersen, 1982), and the promoters from these clones, including the 15 kD, 16 kD, 19 kD, 22 kD, 27 kD, and gamma genes, could also be used to express an ADPglucose pyrophosphorylase gene in the seeds of maize and other plants. Other promoters known to function in maize include the promoters for the following genes: waxy, Brittle, Shrunken 2, Branching enzymes I and II, starch synthases, debranching enzymes, oleosins, glutelins, and sucrose synthases.

Examples of promoters suitable for expression of an ADPglucose pyrophosphorylase gene in wheat include those for the genes for the ADPGPP subunits, for the granule bound and other starch synthases, for the branching and debranching enzymes, for the embryogenesis-abundant proteins, for the gliadins, and for the glutenins. Examples of such promoters in rice include those for the genes for the ADPGPP subunits, for the granule bound and other starch synthases, for the branching enzymes, for the debranching enzymes, for sucrose synthases, and for the glutelins. Examples of such promoters for barley include those for the genes for the ADPGPP subunits, for the granule bound and other starch synthases, for the branching enzymes, for the debranching enzymes, for sucrose synthases, for the hordeins, for the embryo globulins, and the aleurone specific proteins.

The solids content of tomato fruit can be increased by expressing an ADPglucose pyrophosphorylase gene behind a fruit specific promoter. The promoter from the 2A11 genomic clone (Pear, 1989) will control expression of ADPglucose pyrophosphorylase in tomato fruit. The E8 promoter (Deikman, 1988) would also express the ADPglucose pyrophosphorylase in tomato fruits. In addition, novel fruit specific promoters exhibiting high and specific expression during the development of the tomato fruit have been isolated. A differential screening approach utilizing a tomato fruit cDNA library was used to identify suitable cDNA clones that expressed specifically in green fruit. cDNA probes prepared from mRNA extracted from fruit at early and late developing stages, from combined leaf+stem tissue, and from root tissue of the tomato plant were used. Clones that expressed abundantly in green fruit and that showed no detectable expression in leaves were identified. Genomic Southern analysis indicated a small (1–2) gene copy number. The promoters for these cDNA clones were then isolated by screening a tomato genomic clone bank. The expression pattern of these promoters is confirmed by fusion to the β-glucuronidase (GUS) gene and by following the expression of the GUS enzyme during development in transgenic fruit. Promoters that exhibit expression in most cells of the fruit are then fused to the CTP-glgC16 and other glgC alleles or the ADPGPP genes derived from either algae or plants. Results of transformation with a green fruit specific promoter are shown in Example 6.

The solids content of root tissue can be increased by expressing an ADPglucose pyrophosphorylase gene behind a root specific promoter. The promoter from the acid chitinase gene (Samac et al., 1990) would express the ADPglucose pyrophosphorylase in root tissue. Expression in root tissue could also be accomplished by utilizing the root specific subdomains of the CaMV35S promoter that have been identified. (Benfey et al., 1989). The starch content of leaf tissue can be increased by expressing the ADPglucose pyrophosphorylase gene (e.g. glgC gene) using a leaf active promoter such as ssRUBISCO promoter or chlorophyll a/b binding protein gene promoter.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence as discussed above.

The DNA constructs of the present invention also contain a structural coding sequence in double-stranded DNA form, which encodes a fusion polypeptide comprising an amino-terminal plastid transit peptide and an ADPglucose pyrophosphorylase enzyme. The ADPglucose pyrophosphorylase enzyme utilized in the present invention is preferably subject to reduced allosteric control in plants. Such an unregulated ADPglucose pyrophosphorylase enzyme may be selected from known enzymes which exhibit unregulated enzymatic activity or can be produced by mutagenesis of native bacterial, or algal or plant ADPglucose pyrophosphorylase enzymes as discussed in greater detail hereinafter. In some instances, the substantial differences in the nature of regulators modulating the activity of the wild type ADPglucose pyrophosphorylase (ADPGPP) enzyme permits the use of the wild type gene itself; in these instances, the concentration of the regulators within plant organelles will facilitate elicitation of significant ADPGPP enzyme activity.

Bacterial ADPglucose Pyrophosphorylases

The *E. coli* ADPglucose pyrophosphorylase has been well characterized as a tightly regulated enzyme. The activator fructose 1,6-bisphosphate has been shown to activate the enzyme by increasing its $V_{max}$, and by increasing the affinity of the enzyme for its substrates (Preiss, 1966 and Gentner, 1967). In addition, fructose 1,6-bisphosphate (FBP) also modulates the sensitivity of the enzyme to the inhibitors adenosine-5'-monophosphate (AMP) and inorganic phosphate ($P_i$)(Gentner, 1968).

In 1981, the *E. coli* K12 ADPglucose pyrophosphorylase gene (glgC), along with the genes for glycogen synthase and branching enzyme, were cloned, and the resulting plasmid was named pOP12 (Okita, 1981). The glgC gene, which was sequenced in 1983, contains 1293 bp (SEQ ID NO:1) and encodes 431 amino acids (SEQ ID NO:2) with a deduced molecular weight of 48,762 is shown in FIG. 1 (Baecker, 1983).

The glgC16 gene was generated by chemically mutagenizing *E. coli* K12 strain PA 601 with N-methyl-N'-nitrosoguanidine (Cattaneo, 1969 and Creuzet-Sigal, 1972). Glycogen biosynthetic mutants were detected by iodine staining of mutagenized colonies. The glgC16 mutant was found to accumulate up to 48% glycogen during the stationary phase, compared to 20% glycogen in the parent strain. When the kinetics of the glgC16 ADPglucose pyrophosphorylase were compared to the parent, it was found that the glgC16 ADPglucose pyrophosphorylase had a higher affinity for ADPglucose in the absence of the activator, Fructose 1,6-bisphosphate (FBP), and the concentration of FBP needed for half-maximal activation of the enzyme was decreased in glgC16. The inhibition of the ADPglucose pyrophosphorylase activity in glgC16 by 5'-AMP (AMP) was also reduced.

The glgC16 gene from *E. coli* K-12 618 has been cloned (Leung, 1986). Two clones, with opposite orientation, were obtained. These clones, pEBL1 and pEBL3, contained both the glg 16 and the glgB (branching enzyme) genes. Both plasmids were transformed into *E. coli* mutant strains that lacked ADPglucose pyrophosphorylase activity. The *E. coli* K-12 G6MD3 is missing the glggenes, while the *E. coli* B strain, AC70R1-504, has a defective ADPglucose pyrophosphorylase gene and is derepressed five- to seven-fold for the other glycogen biosynthetic activities. Both plasmids, pEBL1 and pEBL3, produced ADPglucose pyrophosphorylase activity in both mutant strains. The cloned ADPglucose pyrophosphorylase was partially purified from *E. coli* strain AC70R1 transformed with the pEBL3 plasmid. This enzyme was kinetically compared to partially purified ADPglucose pyrophosphorylase from the original mutant strain (*E. coli* K-12 618), and to the partially purified ADPglucose pyrophosphorylase from *E. coli* K-12 strain 356, which is the wild type parent strain of strain 618. The wild type and mutant enzymes were compared in their levels of activation and inhibition. The parent strain 356 ADPglucose pyrophosphorylase was activated about 45-fold with fructose 1,6-bisphosphate. The sigmoidal activation curve had a Hill slope of 1.7, and 50% maximal stimulation was seen at 62 µM FBP. The mutant strain 618 ADPglucose pyrophosphorylase was more active in the absence of FBP, and was activated only 1.8- to 2-fold with FBP. The activation curve for the 618 ADPglucose pyrophosphorylase was hyperbolic with a Hill slope of 1.0, and 50% of maximal stimulation was seen at 15+/−3.1 µM. The enzyme expressed from the pEBL3 plasmid gave the same FBP kinetic constants as the ADPglucose pyrophosphorylase from mutant strain 618.

The DNA sequence of the glgC16 gene is now known (SEQ ID NO:3) (Kumar, 1989). Referring to FIG. 2, when the glgC16 deduced amino acid sequence (SEQ ID NO:4) was compared to the nonisogenic *E. coli* K-12 3000, one amino acid change was noted: Gly 336 to Asp (Meyer et al., 1993).

A number of other ADPglucose pyrophosphorylase mutants have been found in *E. coli*. The expression of any of these or other bacterial ADPglucose pyrophosphorylase wild type or mutants could also be used to increase starch production in plants.

*E. coli* K12 strain 6047 (glgC47) accumulates about the same amount of glycogen during stationary phase as does strain 618 (glgC16). Strain 6047, like 618, shows a higher apparent affinity for FBP, and more activity in the absence of FBP. However, the enzyme from strain 6047 is reportedly more sensitive to inhibition by AMP compared to the enzyme from strain 618 (Latil-Damotte, 1977).

The *E. coli* B mutant, SG5, has a higher affinity for its allosteric activators and a lower affinity for its allosteric inhibitor, when compared to its parent strain (Govons, 1969; Govons, 1973 and Preiss, 1973). These changes alone make the enzyme more active under physiological conditions, and this causes the bacteria to accumulate two to three times as much glycogen as the parent strain. The mutant ADPglucose pyrophosphorylase from SG5, like the wild type, exists as a homotetramer. Unlike the wild type, however, FBP causes the mutant enzyme to form higher weight oligomers (Carlson, 1976). The ADPglucose pyrophosphorylase from the *E. coli* B mutant strain CL11136-504 also has a higher apparent affinity for activators and a lower apparent affinity for inhibitors (Kappel, 1981 and Preiss, 1973). This mutant will accumulate three- to four-fold more glycogen than the wild type *E. coli*. Under activated conditions, the purified CL1136-504 enzyme and the wild type (AC70R1) enzyme have comparable specific activities. However, in the absence of any activators, the CL1136-504 enzyme is highly active, unlike the wild type enzyme.

The glgC gene from *Salmonella typhimurium* LT2 has also been cloned and sequenced (Leung and Preiss 1987a). The gene encodes 431 amino acids with a deduced molecular weight of 45,580. The *Salmonella typhimurium* LT2 glgC gene and the same gene from *E. coli* K-12 have 90% identity at the amino acid level and 80% identity at the DNA level. Like the *E. coli* ADPglucose pyrophosphorylase, the *Salmonella typhimurium* LT2 ADPglucose pyrophosphorylase is also activated by FBP and is inhibited by AMP (Leung and Preiss 1987b). This substantial conservation in amino acid sequences suggests that introduction of mutations which cause enhancement of ADPGPP activity in *E. coli* into *S. typhimurium* ADPGPP gene should have a similar effect on the ADPGPP enzyme of this organism.

A number of other bacterial ADPglucose pyrophosphorylases have been characterized by their response to activators and inhibitors (for review see: Preiss 1973). Like the *Escherichia coli* ADPglucose pyrophosphorylase, the ADPglucose pyrophosphorylases from *Aerobacter aerogenes*, *Aerobacter cloacae*, *Citrobacter freundii*, and *Escherichia aurescens* are all activated by FBP and are inhibited by AMP. The ADPglucose pyrophosphorylase from *Aeromonas formicans* is activated by fructose 6-phosphate or FBP, and is inhibited by ADP. The *Serratia marcescens* ADPglucose pyrophosphorylase, however, was not activated by any metabolite tested. The photosynthetic *Rhodospirillum rubrum* has an ADPglucose pyrophosphorylase that is activated by pyruvate, and none of the tested compounds, including $P_i$, AMP or ADP, inhibit the enzyme. Several algal ADPglucose pyrophosphorylases have been studied and found to have regulation similar to that found for plant ADPglucose pyrophosphorylases. Obviously, the ADPglucose pyrophosphorylases from many organisms could be used to increase starch biosynthesis and accumulation in plants.

In addition to *E. coli* and plant ADPGPP enzymes, other sources, including but not limited to cyanobacteria, algae, and other procaryotic and eucaryotic cells can serve as sources for ADPGPP genes. For example, isolation of the Synechocystis and the Anabaena ADPGPP genes could be performed using oligonucleotides corresponding to the *E. coli* ADPGPP activator site, (amino acid residues 25–42 of FIG. 1 ), which is highly conserved across widely divergent species. Oligonucleotides corresponding to this region would facilitate gene isolation when used as probes of genomic libraries. Alternatively, the PCR reaction (described in Example 1) could be used to amplify segments of an ADPGPP gene by using 5' primers corresponding to the *E. coli* activator site, and 3' primers corresponding to *E. coli* catalytic sites, for example, the *E. coli* ADPglucose binding site. Products of the PCR reaction could be used as probes of genomic libraries for isolation of the corresponding full length gene. The sequence of the ADPGPP gene for Synechocystis PCC6803 has been reported (Kahefuda, et al., 1992).

Plant ADPglucose Pyrophosphorylases

At one time, UDPglucose was thought to be the primary substrate for starch biosynthesis in plants. However, ADP-glucose was found to be a better substrate for starch biosynthesis than UDPglucose (Recondo, 1961). This same report states that ADPglucose pyrophosphorylase activity was found in plant material.

A spinach leaf ADPglucose pyrophosphorylase was partially purified and was shown to be activated by 3-phosphoglycerate (3-PGA) and inhibited by inorganic phosphate (Ghosh et al., 1966). The report by Ghosh et al. suggested that the biosynthesis of leaf starch was regulated by the level of ADPglucose. The activator, 3-PGA, is the primary product of $CO_2$ fixation in photosynthesis. During photosynthesis, the levels of 3-PGA would increase, causing activation of ADPglucose pyrophosphorylase. At the same time, the levels of $P_i$ would decrease because of photophosphorylation, decreasing the inhibition of ADPglucose pyrophosphorylase. These changes would cause an increase in ADPglucose production and starch biosynthesis. During darkness, 3-PGA levels would decrease, and $P_i$ levels would increase, decreasing the activity of ADPglucose pyrophosphorylase and, therefore, decreasing biosynthesis of ADPglucose and starch (Ghosh, 1966).

The ADPglucose pyrophosphorylase from spinach leaves was later purified to homogeneity and shown to contain subunits of 51 and 54 kDa (Morell, 1987). Based on antibodies raised against the two subunits, the 51 kDa protein has homology with both the maize endosperm and potato tuber ADPglucose pyrophosphorylases, but not with the spinach leaf 54 kDa protein.

The sequence of a rice endosperm ADPglucose pyrophosphorylase subunit cDNA clone has been reported (Anderson, 1989a). The clone encoded a protein of 483 amino acids. A comparison of the rice endosperm ADPglucose pyrophosphorylase and the *E. coli* ADPglucose pyrophosphorylase protein sequences shows about 30% identity. Also in 1989, an almost full-length cDNA clone for the wheat endosperm ADPglucose pyrophosphorylase was sequenced (Olive, 1989). The wheat endosperm ADPglucose pyrophosphorylase clone has about 24% identity with the *E. coli* ADPglucose pyrophosphorylase protein sequence, while the wheat and the rice clones have 40% identity at the protein level.

Further evidence for the existence of deregulated wild type plant ADPglucose pyrophosphorylases is found in the paper by Olive et al. (Olive, 1989). They claim that the wheat leaf and endosperm ADPglucose pyrophosphorylases have very different allosteric regulation. The endosperm ADPglucose pyrophosphorylase is not activated by 3-PGA and requires ten times more of the inhibitor, orthophosphate, to achieve 50% inhibition than the leaf enzyme.

The maize endosperm ADPglucose pyrophosphorylase has been purified and shown to have catalytic and regulatory properties similar to those of other plant ADPglucose pyrophosphorylases (Plaxton, 1987). The native molecular weight of the maize endosperm enzyme is 230,000, and it is composed of four subunits of similar size.

The native molecular weight of the potato tuber ADPglucose pyrophosphorylase is reported to be 200,000, with a subunit size of 50,000 (Sowokinos, 1982). Activity of the tuber ADPglucose pyrophosphorylase is almost completely dependent on 3-PGA, and as with other plant ADPglucose pyrophosphorylases, is inhibited by $P_i$. The potato tuber and leaf ADPglucose pyrophosphorylases have been demonstrated to be similar in physical, catalytic, and allosteric properties (Anderson, 1989b).

Production of Altered ADPglucose Pyrophosphorylase Genes by Mutagenesis

Those skilled in the art will recognize that while not absolutely required, enhanced results are to be obtained by using ADPglucose pyrophosphorylase genes which are subject to reduced allosteric regulation ("deregulated") and more preferably not subject to significant levels of allosteric regulation ("unregulated") while maintaining adequate catalytic activity. In cells which do not normally accumulate significant quantities of starch, expression of a "regulated" enzyme may be sufficient. In starch-accumulating cells and tissues, a "deregulated" or "unregulated" enzyme is the preferred system. The structural coding sequence for a bacterial or plant ADPglucose pyrophosphorylase enzyme can be mutagenized in *E. coli* or another suitable host and screened for increased glycogen production as described for the glgC16 gene of *E. coli*. It should be realized that use of a gene encoding an ADPglucose pyrophosphorylase enzyme which is only subject to modulators (activators/inhibitors) which are present in the selected plant at levels which do not significantly inhibit the catalytic activity will not require enzyme (gene) modification. These "unregulated" or "deregulated" ADPglucose pyrophosphorylase genes can then be inserted into plants as described herein to obtain transgenic plants having increased starch content.

For example, any ADPglucose pyrophosphorylase gene can be cloned into the *E. coli* B strain AC70R1-504 (Leung, 1986). This strain has a defective ADPglucose pyrophosphorylase gene, and is derepressed five- to seven-fold for the other glycogen biosynthetic enzymes. The ADPglucose pyrophosphorylase gene/ cDNA's can be put on a plasmid behind the *E. coli* glgC promoter or any other bacterial promoter. This construct can then be subjected to either site-directed or random mutagenesis. After mutagenesis, the cells would be plated on rich medium with 1% glucose. After the colonies have developed, the plates would be flooded with iodine solution (0.2 w/v% $I_2$, 0.4 w/v% KI in $H_2O$, Creuzet-Sigal, 1972). By comparison with an identical plate containing non-mutated *E. coli*, colonies that are producing more glycogen can be detected by their darker staining.

Since the mutagenesis procedure could have created promoter mutations, any putative ADPglucose pyrophosphorylase mutant from the first round screening will have to have the ADPglucose pyrophosphorylase gene recloned into non-mutated vector and the resulting plasmid will be screened in the same manner. The mutants that make it though both rounds of screening will then have their ADPglucose pyrophosphorylase activities assayed with and without the activators and inhibitors. By comparing the mutated ADPglucose pyrophosphorylase's responses to activators and inhibitors to the non-mutated enzymes, the new mutant can be characterized.

The report by Plaxton and Preiss in 1987 demonstrates that the maize endosperm ADPglucose pyrophosphorylase has regulatory properties similar to those of the other plant ADPglucose pyrophosphorylases (Plaxton and Preiss 1987). They show that earlier reports claiming that the maize endosperm ADPglucose pyrophosphorylase had enhanced activity in the absence of activator (3-PGA) and decreased sensitivity to the inhibitor ($P_i$), was due to proteolytic cleavage of the enzyme during the isolation procedure. By altering an ADPglucose pyrophosphorylase gene to produce an enzyme analogous to the proteolytically cleaved maize endosperm ADPglucose pyrophosphorylase, decreased allosteric regulation will be achieved. The recent report concerning the apparent novelty of the regulation of the barley endosperm ADPGPP and its apparent insensitivity to 3-PGA is not generally accepted since the report shows that the enzyme preparation was rapidly degraded and may suffer from the same problems identified for the corn endosperm preparation (Plaxton and Preiss, 1987).

To assay a liquid culture of *E. coli* for ADPglucose pyrophosphorylase activity, the cells are spun down in a centrifuge and resuspended in about 2 ml of extraction buffer (0.05M glycylglycine pH 7.0, 5.0 mM DTE, 1.0 mM EDTA) per gram of cell paste. The cells are lysed by passing twice through a French Press. The cell extracts are spun in a microcentrifuge for 5 minutes, and the supernatants are desalted by passing through a G-50 spin column.

The enzyme assay for the synthesis of ADPglucose is a modification of a published procedure/Haugen, 1976). Each 100 µl assay contains: 10 µmole Hepes pH 7.7, 50 µg BSA, 0.05 µmole of [$^{14}$C]glucose-1-phosphate, 0.15 µmole ATP, 0.5 µmole $MgCl_2$, 0.1 µg of crystalline yeast inorganic pyrophosphatase, 1 mM ammonium molybdate, enzyme, activators or inhibitors as desired, and water. The assay is incubated at 37° C. for 10 minutes, and is stopped by boiling for 60 seconds. The assay is spun down in a microcentrifuge, and 40 µl of the supernatant is injected onto a Synchrom Synchropak AX-100 anion exchange HPLC column. The sample is eluted with 65 mM KPi pH 5.5. Unreacted [$^{14}$C]glucose-1-phosphate elutes around 7–8 minutes, and [$^{14}$C]ADPglucose elutes at approximately 13 minutes. Enzyme activity is determined by the amount of radioactivity found in the ADPglucose peak.

The plant ADPGPP enzyme activity is tightly regulated, by both positive (3-phosphoglycerate; 3-PGA) and negative effectors (inorganic phosphate; $P_i$) (Ghosh and Preiss, 1966; Copeland and Preiss 1981; Sowokinos and Preiss 1982; Morell et al., 1987; Plaxton and Preiss, 1987; Preiss, 1988;) and the ratio of 3-PGA:$P_i$ plays a prominent role in regulating starch biosynthesis by modulating the ADPGPP activity (Santarius and Heber, 1965; Heldt et al., 1977; Kaiser and Bassham, 1979). The plant ADPGPP enzymes are heterotetramers of two large/"shrunken" and two small/"Brittle" subunits (Morell et al., 1987; Lin et al., 1988a, 1988b; Krishnan et al., 1986; Okita et al., 1990) and there is strong evidence to suggest that the heterotetramer is the most active form of ADPGPP. Support for this suggestion comes from the isolation of plant "starchless" mutants that are deficient in either of the subunits (Tsai and Nelson, 1966; Dickinson and Preiss, 1969; Lin et al., 1988a. 1988b) and from the characterization of an "ADPGPP" homotetramer of small subunits that was found to have only low enzyme activity (Lin et al., 1988b). In addition, proposed effector interaction residues have been identified for both subunits (Morell et al., 1988). Direct evidence for the active form of the enzyme and further support of the kinetic data reported for the purified potato enzyme comes from the expression of potato ADPGPP activity in *E. coli* and the comparison of the kinetic properties of this material and that from potato tubers (Iglesias et al., 1993).

Unregulated enzyme variants of the plant ADPGPP are identified and characterized in a manner similar to that which resulted in the isolation of the *E. coli* glgC16 and related mutants. A number of plant ADPGPP cDNA's, or portions of such cDNA's, for both the large and small subunits, have been cloned from both monocots and dicots (Anderson et al., 1989a; Olive et al., 1989; Muller et al., 1990; Bhave et al., 1990; du Jardin and Berhin, 1991) The proteins encoded by the plant cDNA's, as well as those described from bacteria, show a high degree of conservation (Bhave et al., 1990). In particular, a highly conserved region, also containing some of the residues implicated in enzyme function and effector interactions, has been identified (Morell et al., 1988; du Jardin and Berhin, 1991; Smith-White and Preiss, 1992). Clones of the potato tuber ADPGPP subunit genes have been isolated. These include a complete small subunit gene, assembled by addition of sequences from the first exon of the genomic clone with a nearly full-length cDNA clone of the same gene, and an almost complete gene for the large subunit. The nucleotide sequence (SEQ ID NO:7) and the amino acid sequence (SEQ ID NO:8) of the assembled small subunit gene is presented in FIG. 5. The nucleotide sequence presented here differs from the gene originally isolated in the following ways: a BglII+NcoI site was introduced at the ATG codon to facilitate the cloning of the gene into E. coli and plant expression vectors by site directed mutagenesis utilizing the oligonucleotide primer sequence

GTTGATAACAAGATCTGTTAACCATGGCGGCTTCC (SEQ ID NO:11).

A SacI site was introduced at the stop codon utilizing the oligonucleotide primer sequence

CCAGTTAAAACGGAGCTCATCAGATGATGATTC (SEQ ID NO:12).

The SacI site serves as a 3' cloning site. An internal BglII site was removed utilizing the oligonucleotide primer sequence

GTGTGAGAACATAAATCTTGGATATGTTAC (SEQ ID NO:13).

This assembled gene was expressed in E. coli under the control of the recA promoter in a PrecA-gene10L expression cassette (Wong et al., 1988) to produce measurable levels of the protein. An initiating methionine codon is placed by site-directed mutagenesis utilizing the oligonucleotide primer sequence

GAATTCACAGGGCCATGGCTCTAGACCC (SEQ ID NO:14)

to express the mature gene.

The nucleotide sequence (SEQ ID NO:9) and the amino acid sequence (SEQ ID NO:10) of the almost complete large subunit gene is presented in FIG. 6. An initiating methionine codon has been placed at the mature N-terminus by site-directed mutagenesis utilizing the oligonucleotide primer sequence

AAGATCAAACCTGCCATGGCTTACTCTGTGATCACTACTG (SEQ ID NO:15).

The purpose of the initiating methionine is to facilitate the expression of this large subunit gene in E. coli. A HindIII site is located 103 bp after the stop codon and serves as the 3' cloning site. The complete large ADPGPP gene is isolated by the 5' RACE procedure (Rapid Amplification of cDNA Ends; Frohman, 1990; Frohman et al., 1988; Loh et al., 1989). The oligonucleotide primers for this procedure are as follows:

1) GGGAATTCAAGCTTGGATCCCGGGC-CCCCCCCCCCCCCC (SEQ ID NO:16);

2) GGGAATTCAAGCTTGGATCCCGGG (SEQ ID NO:17); and

3) CCTCTAGACAGTCGATCAGGAGCAGATGTACG (SEQ ID NO:18).

The first two are the equivalent to the ANpolyC and the AN primers of Loh et al. (1989), respectively, and the third is the reverse complement to a sequence in the large ADPGPP gene, located after the Pst I site in the sequence in FIG. 6. The PCR 5' sequence products are cloned as EcoRI/HindIII/BamHI-PstI fragments and are easily assembled with the existing gene portion.

The weakly regulated enzyme mutants of ADPGPP are identified by initially scoring colonies from a mutagenized E. coli culture that show elevated glycogen synthesis, by iodine staining of 24–48 hour colonies on Luria-Agar plates containing glucose at 1%, and then by characterizing the responses of the ADPGPP enzymes from these isolates to the positive and negative effectors of this activity (Cattaneo et al., 1969; Preiss et al., 1971). A similar approach is applied to the isolation of such variants of the plant ADPGPP enzymes. Given an expression system for each of the subunit genes, mutagenesis of each gene is carried out separately, by any of a variety of known means, both chemical or physical (Miller, 1972) on cultures containing the gene or on purified DNA. Another approach is to use a PCR procedure (Ehrlich, 1989) on the complete gene in the presence of inhibiting Mn++ ions, a condition that leads to a high rate of misincorporation of nucleotides. A PCR procedure may also be used with primers adjacent to just a specific region of the gene, and this mutagenized fragment then recloned into the non-mutagenized gene segments. A random synthetic oligonucleotide procedure may also be used to generate a highly mutagenized short region of the gene by mixing of nucleotides in the synthesis reaction to result in misincorporation at all positions in this region. This small region is flanked by restriction sites that are used to reinsert this region into the remainder of the gene. The resultant cultures or transformants are screened by the standard iodine method for those exhibiting glycogen levels higher than controls. Preferably this screening is carried out in an E. coli strain deficient only in ADPGPP activity and is phenotypically glycogen-minus and that is complemented to glycogen-plus by glgC. The E. coli strain should retain those other activities required for glycogen production. Both genes are expressed together in the same E. coli host by placing the genes on compatible plasmids with different selectable marker genes, and these plasmids also have similar copy numbers in the bacterial host to maximize heterotetramer formation. An example of such an expression system is the combination of pMON17335 and pMON17336 (Iglesias et al., 1993). The use of separate plasmids enables the screening of a mutagenized population of one gene alone, or in conjunction with the second gene following transformation into a competent host expressing the other gene, and the screening of two mutagenized populations following the combining of these in the same host. Following re-isolation of the plasmid DNA from colonies with increased iodine staining, the ADPGPP coding sequences are recloned into expression vectors, the phenotype verified, and the ADPGPP activity and its response to the effector molecules determined. Improved variants will display increased $V_{max}$, reduced inhibition by the negative effector ($P_i$), or reduced dependence upon activator (3-PGA) for maximal activity. The assay for such improved characteristics involves the determination of ADPGPP activity in the presence of $P_i$ at 0.045 mM ($I_{0.5}$=0.045 mM) or in the presence of 3-PGA at 0.075 mM ($A_{0.5}$=0.075 mM). The useful variants will display <40% inhibition at this concentration of $P_i$ or display >50% activity at this concentration of 3-PGA. Following the isolation of improved variants and the determination of the subunit or subunits responsible, the mutation(s) are determined by nucleotide sequencing. The mutation is confirmed by recreating this change by site-directed mutagenesis and reassay of ADPGPP activity in the presence of activator and inhibitor. This mutation is then transferred to the equivalent complete ADPGPP cDNA gene, by recloning the region containing the change from the altered bacterial expression form to the plant form containing the amyloplast targeting sequence, or by site-directed mutagenesis of the complete native ADPGPP plant gene.

Chloroplast/Amyloplast Directed Expression of ADPglucose Pyrophosphorylase Activity Starch biosynthesis is known to take place in plant chloroplasts and amyloplasts (herein collectively referred to as plastids. In the plants that have been studied, the ADPglucose pyrophosphorylase is localized to these plastids. ADPglucose pyrophosphorylase is restricted to the chloroplasts in pea shoots (Levi, 1978). In spinach leaves, all of the ADPglucose pyrophosphorylase activity, along with the starch synthase activity, is found in the chloroplasts (Mares, 1978 and Okita, 1979). Immunocytochemical localization shows that the potato tuber ADPglucose pyrophosphorylase is found exclusively in the amyloplasts (Kim, 1989). Studies with rice endosperm also shows that the ADPglucose pyrophosphorylase activity is localized in the amyloplasts (Nakamura, 1989).

Many chloroplast-localized proteins are expressed from nuclear genes as precursors and are targeted to the chloroplast by a chloroplast transit peptide (CTP) that is removed during the import steps. Examples of such chloroplast proteins include the small subunit of Ribulose-1,5-bisphosphate carboxylase (ssRUBISCO, SSU), 5-enolpyruvateshikimate-3-phosphate synthase (EPSPS), Ferredoxin, Ferredoxin oxidoreductase, the Light-harvesting-complex protein I and protein II, and Thioredoxin F. It has been demonstrated in vivo and in vitro that non-chloroplast proteins may be targeted to the chloroplast by use of protein fusions with a CTP and that a CTP sequence is sufficient to target a protein to the chloroplast. Likewise, amyloplast-localized proteins are expressed from nuclear genes as precursors and are targeted to the amyloplast by an amyloplast transit peptide (ATP). It is further believed that the chloroplast and amyloplast are developed from common proplastids and are functionally distinct only in that the former is found in photosynthetic cells and the latter in non-photosynthetic cells. In fact, interconversion between the two organella has been observed in plants such as Picea abies (Senser, 1975). There are also reports showing that the amyloplast and chloroplast genomes from the same plant are indistinguishable (Scott, 1984; Macherel, 1985 and Catley, 1987). It has been further shown that an amyloplast transit peptide functions to import the associated polypeptide into chloroplasts (Klösgen, 1989).

In the exemplary embodiments, a specialized CTP, derived from the ssRUBISCO 1A gene from Arabidopsis thaliana (SSU 1A) (Timko, 1988) was used. This CTP (CTP1) was constructed by a combination of site-directed mutageneses. The CTP1 nucleotide sequence (SEQ ID NO:5) and the corresponding amino acid sequence (SEQ ID NO:6) is also shown in FIG. 3. CTP1 is made up of the SSU 1A CTP (amino acid 1–55), the first 23 amino acids of the mature SSU 1A protein (56–78), a serine residue (amino acid 79), a new segment that repeats amino acids 50 to 56 from the CTP and the first two from the mature protein (amino acids 80–87), and an alanine and methionine residue (amino acid 88 and 89). An NcoI restriction site is located at the 3' end (spans the Met codon, to facilitate the construction of precise fusions to the 5' of an ADPglucose pyrophosphorylase gene. At a later stage, a BglII site was introduced upstream of the N-terminus of the SSU 1A sequences to facilitate the introduction of the fusions into plant transformation vectors. A fusion was assembled between the structural DNA encoding the CTP1 CTP and the glgC16 gene from E. coli to produce a complete structural DNA sequence encoding the plastid transit peptide/ADPglucose pyrophosphorylase fusion polypeptide.

Those skilled in the art will recognize that if either a single plant ADPglucose pyrophosphorylase cDNA encoding shrunken and/or brittle subunits or both plant ADPGPP cDNA's encoding shrunken and brittle subunits is utilized in the practice of the present invention, the endogenous CTP or ATP could most easily and preferably be used. Hence, for purposes of the present invention the term "plastid transit peptides" should be interpreted to include both chloroplast transit peptides and amyloplast transit peptides. Those skilled in the art will also recognize that various other chimeric constructs can be made which utilize the functionality of a particular plastid transit peptide to import the contiguous ADPglucose pyrophosphorylase enzyme into the plant cell chloroplast/amyloplast depending on the promoter tissue specificity.

The functionality of the fusion polypeptide can be confirmed using the following in vitro plastid uptake assay: Intact chloroplasts are isolated from lettuce (Latuca sativa, var. longifolia) by centrifugation in Percoll/ficoll gradients as modified from Bartlett et al (1982). The final pellet of intact chloroplasts is suspended in 0.5 ml of sterile 330 mM sorbitol in 50 mM Hepes-KOH, pH 7.7, assayed for chlorophyll (Arnon, 1949), and adjusted to the final chlorophyll concentration of 4 mg/ml (using sorbitol/Hepes). The yield of intact chloroplasts from a single head of lettuce is 3–6 mg chlorophyll. A typical 300 µl uptake experiment contained 5 mM ATP, 8.3 mM unlabeled methionine, 322 mM sorbitol, 58.3 mM Hepes-KOH (pH 8.0), 50 µl reticulocyte lysate translation products, and intact chloroplasts from L. sativa (200 µg chlorophyll). The uptake mixture is gently rocked at room temperature (in 10×75 mm glass tubes) directly in front of a fiber optic illuminator set at maximum light intensity (150 Watt bulb). Aliquots of the uptake mix (50 µl) are removed at various times and fractionated over 100 µl silicone-oil gradients (in 150 µl polyethylene tubes) by centrifugation at 11,000×g for 30 seconds Under these conditions, the intact chloroplasts form a pellet under the silicone-oil layer and the incubation medium (containing the reticulocyte lysate) floats on the surface. After centrifugation, the silicone-oil gradients are immediately frozen in dry ice. The chloroplast pellet is then resuspended in 50–100 µl of lysis buffer (10 mM Hepes-KOH pH 7.5, 1 mM PMSF, 1 mM benzamidine, 5 mM α-amino-n-caproic acid, and 30 µg/ml aprotinin) and centrifuged at 15,000×g for 20 minutes to pellet the thylakoid membranes. The clear supernatant (stromal proteins) from this spin, and an aliquot of the reticulocyte lysate incubation medium from each uptake experiment, are mixed with an equal volume of 2× NaDodSO4-PAGE sample buffer for electrophoresis (see below). SDS-PAGE is carried out according to Laemmli (1970) in 3–17% (w/v) acrylamide slab gels (60 mm×1.5 mm) with 3% (w/v) acrylamide stacking gels (5 mm×1.5 mm). The gel is fixed for 20–30 minutes in a solution with 40% methanol and 10% acetic acid. Then, the gel is soaked in EN³HANCE™ (DuPont) for 20–30 minutes, followed by drying the gel on a gel dryer. The gel is imaged by autoradiography, using an intensifying screen and an overnight exposure to determine whether the ADPglucose pyrophosphorylase is imported into the isolated chloroplasts.

An alternative means for enhancing ADPglucose levels in plant cells will be to isolate genes encoding transcription factors which interact with the upstream regulatory elements of the plant ADPglucose pyrophosphorylase gene(s). Enhanced expression of these transcription factors in plant cells can cause enhanced expression of the ADPglucose pyrophosphorylase gene. Under these conditions, the increased starch content is still realized by an increase in the activity of the ADPglucose pyrophosphorylase enzyme although the mechanism is different. Methods for the isolation of transcription factors have been described (Katagiri, 1989).

Polyadenylation Signal

The 3' non-translated region of the chimeric plant gene contains a polyadenylation signal which functions in plants to cause the addition of polyadenylate nucleotides to the 3' end of the RNA. Examples of suitable 3' regions are (1) the 3' transcribed, non-translated regions containing the polyadenylated signal of Agrobacterium the tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gent. An example of a preferred 3' region is that from the NOS gene, described in greater detail in the examples below.

Plant Transformation/Regeneration

Plants which can be made to have increased starch content by practice of the present invention include, but are-not limited to, corn, wheat, rice, carrot, onion, pea, tomato, potato, sweet potato, peanut, canola/oilseed rape, cotton, barley, sorghum, cassava, banana, soybean, lettuce, apple, sunflower, almond, cashew, pecan, and walnut.

A double-stranded DNA molecule of the present invention containing the functional plant ADPglucose pyrophosphorylase gene can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1983,), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A plasmid expression vector, suitable for the expression of the *E. coli* glgC16 and other ADPGPP genes in monocots is composed of the following: a promoter that is specific or enhanced for expression in the starch storage tissues in monocots, generally the endosperm, such as promoters for the zein genes found in the maize endosperm (Pedersen et al., 1982); an intron that provides a splice site to facilitate expression of the gene, such as the ADH1 intron (Callas et al., 1987); and a 3' polyadenylation sequence such as the nopaline synthase 3' sequence (NOS 3'; Fraley et al., 1983). This expression cassette may be assembled on high copy replicons suitable for the production of large quantities of DNA.

A particularly useful Agrobacterium-based plant transformation vector for use in transformation of dicotyledonous plants is plasmid vector pMON530 (Rogers, S. G., 1987). Plasmid pMON530 (see FIG. 4) is a derivative of pMON505 prepared by transferring the 2.3 kb StuI-HindIII fragment of pMON316 (Rogers, S. G., 1987) into pMON526. Plasmid pMON526 is s simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers, S. G., 1987) in which the Ti plasmid homology region, LIH, has been replaced with a 3.8 kb HindIII to SmaI segment of the mini RK2 plasmid, pTJS75 (Schmidhauser & Helinski, 1985). This segment contains the RK2 origin of replication, oriV, and the origin of transfer, oriT, for conjugation into Agrobacterium using the triparental mating procedure (Horsch & Klee, 1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny and a pBR322 origin of replication for ease in making large amounts of the vector in *E. coli*. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

When adequate numbers of cells (or protoplasts) containing the ADPglucose pyrophosphorylase gene or cDNA are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, corn, etc.), Solanaceae (potato, tobacco, tomato, peppers), various floral crops, such as sunflower, and nut-bearing trees, such as almonds, cashews, walnuts, and pecans. See, e.g., Ammirato, 1984; Shimamoto, 1989: Fromm, 1990; Vasil, 1990; Vasil, 1992; Hayashimoto, 1989; Shimamoto, 1989; and Datta, 1990.

The following examples are provided to better elucidate the practice of the present invention and should not be interpreted in any way to limit the scope of the present invention. Those skilled in the art will recognize that various modifications, truncations, etc. can be made to the methods and genes described herein while not departing from the spirit and scope of the present invention.

EXAMPLES

Example 1

To express the *E. coli* glgC16 gene in plant cells, and to target the enzyme to the plastids, the gene needed to be fused to a DNA encoding the plastid-targeting transit peptide (hereinafter referred to as the CTP/ADPglucose pyrophosphorylase gene), and to the proper plant regulatory regions. This was accomplished by cloning the glgC16 gene into a series of plasmid vectors that contained the needed sequences.

The plasmid pLP226 contains the glgC16 gene on a HincII fragment, cloned into a pUC8 vector at the HincII site (Leung et al. 1986). pLP226 was obtained from Dr. Jack Preiss at Michigan State University, and was transformed into frozen competent *E. coli* JM101 cells, prepared by the calcium chloride method (Sambrook et al., 1989). The transformed cells were plated on 2XYT (infra) plates that contained ampicillin at 100 μg/ml. The plasmid pLP226 was purified by the rapid alkaline extraction procedure (RAE) from a 5 ml overnight culture (Birnboim and Doly 1979).

To fuse the glgC16 gene to the DNA encoding the chloroplast transit peptide, a NcoI site was needed at the 5' end of the gene. A SacI site downstream of the termination codon was also needed to move the CTP/ADPglucose pyrophosphorylase gene into the next vector. In order to introduce these sites, a PCR reaction (#13) was run using approximately 20 ng of rapid alkaline extraction-purified plasmid pLP226 for a template. The reaction was set up following the recommendations of the manufacturer (Perkin Elmer Cetus). The primers were QSP3 and QSP7. QSP3 was designed to introduce the NcoI site that would include the start codon for the glgC 16 gene. The QSP7 primer hybridized in the 3' nontranslated region of the glgC16 gene and added a SacI site. The Thermal Cycler was programmed for 30 cycles with a 1 minute 94° C. denaturation step, a 2 minute 50° C. annealing step, and a 3 minute 72° C. extension step. After each cycle, the extension step was increased by 15 seconds.

QSP3 Primer (SEQ ID NO:19): 5'-GGAGTTAGCCATG-GTTAGTTTAGAG-3'

QSP7 Primer (SEQ ID NO:20):

5'-GGCCGAGCTCGTCAACGCCGTCTGCGATTTGTGC-3'
(SEQ ID NO:20)

The vector that the PCR product was cloned into was pGEM3zf+ (obtained from Promega, Madison, Wis.) that had been digested with SacI and Hind III, and had the DNA for the modified Arabidopsis small subunit CTP1 ligated at the HindIII site. The DNA (SEQ ID NO:5) and amino acid sequence (SEQ ID NO:6) of this CTP1 are shown in FIG. 3.

The linearized vector was treated with 5 units of calf intestinal alkaline phosphatase for 30 minutes at 56° C. Then, both the vector and the PCR #13 fragment, which had the glgC16 gene with the new NcoI and SacI sites, were run on an agarose gel and the fragments were purified by binding to DEAE membranes. The protocol used for the fragment purification with the DEAE membrane is from Schleicher and Schuell, and is titled "Binding and Recovery of DNA and RNA Using S and S DEAE Membrane."

Ligation #5 fused the glgC16 gene to the DNA for the modified Arabidopsis SSU CTP with the pGEM3zf+. The ligation contained 3 μl of vector that had been digested with NcoI and SacI, along with 3 μl of the PCR #13 product, that had also been cut with NcoI and SacI and repurified on a gel. 5 μl (of 20 μl total) of ligation #5 was transformed into frozen competent JM101 cells, and the transformed cells were plated on 2XYT plates (16 g/l Bacto-tryptone, 10 g/l yeast extract, 10 g/l NaCl, pH 7.3, and solidified with 1.5% agar) containing ampicillin.

Sample 1 was picked from a plate after overnight growth. This sample was inoculated into 4 ml of 2XYT media and grown overnight at 37° C. The plasmid was isolated by the rapid alkaline extraction procedure, and the DNA was digested with EcoRI, NcoI, and EcoRI and NcoI together. The digest was separated on an agarose gel, and the expected fragments were observed. The plasmid isolated from sample 1 was designated pMON20100, and consisted of pGEM3zf+, the DNA for the modified Arabidopsis SSU CTP, and the glgC16 gene. The fusion was in the orientation that allowed it to be transcribed from the SP6 polymerase promoter.

To test this construct for import of the ADPglucose pyrophosphorylase into isolated lettuce chloroplasts, the CTP/ADPglucose pyrophosphorylase fusion needed to be transcribed and translated to produce [$^{35}$S]-labeled ADPglucose pyrophosphorylase. To make a DNA template for transcription by the SP6 polymerase, the CTP/ADPglucose pyrophosphorylase region of pMON20100 was amplified by PCR to generate a large amount of linear DNA. To do this, about 0.1 μl of pMON20100, that had been purified by rapid alkaline extraction, was used as a template in PCR reaction #80. The primers were a commercially available SP6 promoter primer (Promega) and the oligo QSP7. The SP6 primer hybridized to the SP6 promoter in the vector, and included the entire SP6 promoter sequence. Therefore, a PCR product primed with this oligonucleotide will contain the recognition sequence for the SP6 polymerase. The QSP7 primer will hybridize in the 3' nontranslated region of the glgC16 gene. This is the same primer that was used to introduce a SacI site downstream of the glgC16 termination codon. The Thermal Cycler was programmed for 30 cycles with a 1 minute denaturation at 94° C., a 2 minute annealing at 55° C., and a 3 minute extension at 72° C. After each cycle, 15 seconds were added to the extension step.

SP6 Promoter Primer (SEQ ID NO:21): 5'-GATTTAG-GTGACACTATAG-3'

5 μl of PCR reaction #80 was run on an agarose gel and purified by binding to DEAE membrane. The DNA was eluted and dissolved in 20 μl of TE. 2 μl of the gel-purified PCR #80 product was used in an SP6 RNA polymerase in vitro transcription reaction. The reaction conditions were those described by the supplier (Promega) for the synthesis of large amounts of RNA (100 μl reaction). The RNA produced from the PCR reaction #80 DNA was used for in vitro translation with the rabbit reticulocyte lysate system (Promega). $^{35}$S-labeled protein made from pMON20100 (i.e., PCR reaction#80) was used for an in vitro chloroplast import assay as previously described. After processing the samples from the chloroplast import assay, the samples were subjected to electrophoresis on SDS-PAGE gels with a 3–17% polyacrylamide gradient. The gel was fixed for 20–30 minutes in a solution with 40% methanol and 10% acetic acid. Then, the gel was soaked in EN$^3$HANCE™ for 20–30 minutes, followed by drying the gel on a gel dryer. The gel was imaged by autoradiography, using an intensifying screen and an overnight exposure. The results demonstrated that the fusion protein was imported into the isolated chloroplasts.

The construct in pMON20100 was next engineered to be fused to the Enhanced-CaMV35S promoter (Kay, R. 1987) and the NOS 3' end (Bevan, M. 1983) isolated from pMON999. PCR reaction 114 contained plasmid pMON 20100 as a template, and used primers QSM11 and QSM10. QSM11 annealed to the DNA for the modified Arabidopsis SSU CTP and created a BglII site 7 bp upstream from the ATG start codon. QSM10 annealed to the 3' end of the glgC16 gene and added an XbaI site immediately after the termination codon, and added a SacI site 5 bp after the termination codon. The SacI site that had earlier been added to the glgC16 gene was approximately 100 bp downstream of the termination codon. The Thermal Cycler was programmed for 25 cycles with a 1 minute 94° C. denaturation, a 2 minute 55° C. annealing, and a 3 minute 72° C. extension step. With each cycle, 15 seconds was added to the extension step.

QSM11 Primer (SEQ ID NO:22): 5'-AGAGAGATCTA-GAACAATGGCTTCCTCTATGCTCTCTTCCGC-3'

QSM10 Primer (SEQ ID NO:23): 5'-GGCCGAGCTCTA-GATTATCGCTCCTGTTTATGCCCTAAC-3'

Ninety-five (95) µl (from 100 µl total volume) of PCR reaction #114 was ethanol precipitated, and resuspended in 20 µl of TE. Five (5) µl of this was digested with BglII (4 units) and SacI (10 units) overnight at 37° C. Five (5) µl (5 µg) of the vector, pMON999, which contains the Enhanced CaMV35S promoter and the NOS 3' end, was digested in the same manner. After digestion with the restriction enzymes, the DNAs were run on an agarose gel and purified by binding to DEAE membranes. Each of the DNAs were dissolved in 20 µl of TE. One (1) µl of PCR 114 was ligated with 3 µl of the vector, in a total volume of 20 µl. The ligation mixture was incubated at 14° C. for 7 hours. Ten (10) µl of the ligation was transformed into frozen competent MM294 cells and plated on LB plates (10 g/l Bactotryptone, 5 g/l yeast extract, 10 g/l NaCl, and 1.5% agar to solidify) with 100 µg/ml ampicillin. Colonies were picked and inoculated into tubes with 5 ml of LB media with 100 µg/ml ampicillin, for overnight growth. The 5 ml overnight cultures were used for rapid alkaline extractions to isolate the plasmid DNAs. The DNAs were digested with EcoRI, and separate aliquots were digested with NotI. After analyzing these samples on agarose gels, the plasmid pMON20102 was confirmed to have the 497 bp EcoRI fragment that is characteristic of the glgC16 gene. This plasmid also contained the 2.5 kb NotI fragment which contained the Enhanced CaMV35s promoter, the DNA for the modified Arabidopsis SSU CTP, the glgC16 gene, and the NOS 3' end.

The 2.5 kb NotI cassette was then transferred into a plant transformation vector, pMON530 (FIG. 4). pMON530 contains a unique NotI site in the RK2 region, exactly 600 bp after the HindIII site. A description of the construction of pMON530 can be found in Rogers et al., 1987. Twenty (20) µg of pMON530 was digested with 40 units of NotI overnight at 37° C. The digested vector was then dephosphorylated with 22 units of calf alkaline intestinal phosphatase at 37° C. for about 1 hour. The pMON530 vector was extracted with phenol/chloroform, then chloroform, and was ethanol precipitated. Ten (10) µg of plasmid pMON20102 was also digested overnight at 37° C. with 40 units of NotI. The NotI-digested pMON530 vector was ligated to the NotI cassette from plasmid pMON20102 at 15° C. overnight. The ligation was transformed into frozen competent JM101 *E. coli* cells, and the transformed cells were plated on LB with 75 µg/ml spectinomycin.

Nine colonies were picked from the transformation plate and grown in 5 ml LB cultures for screening. Plasmids from 5 ml cultures were prepared by the rapid alkaline extraction procedure. The DNAs were first screened by SalI digestions which were separated on a 1% agarose gel. By comparing the resulting pattern with the SalI digest of the parent plasmid, pMON530, the correct construct was isolated. The construct was designated pMON20104 and the orientation determined by PstI digestion and NcoI/BglII double digestion. The Enhanced CaMV35s promoter driving the CTP/ADPglucose pyrophosphorylase gene is in the same orientation as the CaMV35S promoter that was already present in pMON530.

In preparation for transforming tobacco cells, pMON20104 was mated into Agrobacterium ASE by a triparental mating with the helper plasmid pRK2013. The Agrobacterium was grown 1.5 days in LB with 25 µg/ml chloramphenicol and 50 µg/ml kanamycin at 30° C. *E. coli* containing pRK2013 was grown overnight in kanamycin (50 µg/ml). This culture was started with several colonies from a plate. *E. coli* with pMON20104 was grown in LB with 75 µg/ml spectinomycin. After all of the cultures were grown, 4 ml of LB was added to a tube with 100 µl each of Agrobacterium ASE, pRK2013, and pMON20104. This mixture was spun in a microfuge for 5 minutes and decanted. The pellet was resuspended in the remaining liquid, and pipetted into the middle of an LB plate. After overnight growth at 30° C., a loop of cells from this plate was streaked onto an LB plate with 75 µg/ml spectinomycin and 25 µg/ml chloramphenicol.

After 1–2 days at 30° C., the plate from the triparental mating of pMON20104, Agrobacterium ASE, and pRK2013, had growing colonies, while the control plate from the mating of pMON20104 and ASE (without pRK2013, which is needed for mobilization) did not. After the triparental mating, 2 colonies were picked from the plate, inoculated into a liquid culture with 75 µg/ml spectinomycin, 25 µg/ml chloramphenicol, and 50 µg/ml kanamycin, and grown at 30° C. These two cultures were used for transformation into tobacco.

The tobacco leaf disc transformation protocol uses healthy leaf tissue about 1 month old. After a 15–20 minute surface sterilization with 10% Clorox plus a surfactant, the leaves were rinsed 3 times in sterile water. Using a sterile paper punch, leaf discs are punched and placed upside doom on MS104 media (MS salts 4.3 g/l, sucrose 30 g/l, B5 vitamins 500×2 ml/l, NAA 0.1 mg/l, and BA 1.0 mg/l) for a 1 day preculture.

The discs were then inoculated with an overnight culture of Agrobacterium ASE:pMON20104 that had been diluted 1/5 (i.e.,: about 0.6 OD). The inoculation was done by placing the discs in centrifuge tubes with the culture. After 30 to 60 seconds, the liquid was drained off and the discs were blotted between sterile filter paper. The discs were then placed upside down on MS104 feeder plates with a filter disc to co-culture.

After 2–3 days of co-culture, the discs were transferred, still upside down, to selection plates with MS104 media. After 2–3 weeks, callus formed, and individual clumps were separated from the leaf discs. Shoots were cleanly cut from the callus when they were large enough to distinguish from stems. The shoots were placed on hormone-free rooting media (MSO: MS salts 4.3 g/l, sucrose 30 g/l, and B5 vitamins 500×2 ml/l) with selection. Roots formed in 1–2 weeks. Rooted shoots were placed in soil and were kept in a high humidity environment (i.e., plastic containers or bags). The shoots were hardened off by gradually exposing them to ambient humidity conditions.

Starch levels of transformed callus tissue was quantitated by a modification of the procedure of Lin et al. (Lin et al. 1988a). Clumps of callus were removed from their plates, taking care not to include any agar. The callus was put into 1.5 ml microcentrifuge tubes and dried under a vacuum in a SPEED VAC™ (Savant). After several hours of drying, the tubes were removed and weighed on an analytical balance to the closest 0.1 mg. The tubes were returned to the SPEED VAC™ for several more hours, then were reweighed to determine if a stable dry weight had been obtained. The dried callus was ground in the tube and thoroughly mixed, to give a homogenous sample. An aliquot of each dried callus sample was removed and put into a preweighed 1.5 ml microcentrifuge tube. These new tubes were then reweighed, and the weight of the calli samples in them was determined. The samples ranged from 9 to 34 mg.

Approximately 1 ml of 80% ethanol was added to each tube, and the tubes were incubated in a 70° C. water bath for 10–20 minutes. The samples were then spun down, and the ethanol was removed. The ethanol wash was done 2 more times. After the last ethanol wash, the samples were dried in a Speed Vac™, then 200 μl of 0.2N KOH was added to each tube. The samples were ground using an overhead stirrer, then the samples were heated at 100° C. for 30 minutes. Before heating the tubes, several small holes were made in the caps with a needle. This prevented the caps from popping off and causing a loss of sample. After the heating step, 40 μl of 1N acetic acid was added to each sample. 35 μl (7.4 units) of pancreatic alpha-amylase was added, followed by a 30 minute incubation at 37° C. Next, 5 units (in 5 μl) amyloglucosidase (from *Aspergillus niger*) was added to each sample, along with 160 μl of 100 mM sodium acetate pH. 4.6. The samples were heated to 55° C. for 1 hour, boiled for 2–3 minutes, and briefly spun down in a microcentrifuge. At this point, the samples were again dried in a Speed Vac™, and were resuspended in 1000 μl of 100 mM Tris-Cl pH 7.5.

The samples were then assayed for glucose using the Glucose [HK] assay from Sigma (catalogue #16-10). Using this assay, glucose in the samples (+ATP) is converted to glucose-6-phosphate+ADP by hexokinase. The glucose-6-phosphate (+NAD) is converted to 6-phosphogluconate+ NADH. The increase in absorbance at 340 nm, due to NADH, is measured and is directly proportional to the glucose concentration. All assays and calculations were done as recommended by Sigma. The assays were conducted following Sigma's "Alternate Procedure," at room temperature with 10 μl of sample per assay, or 5 μl of sample+5 μl of 100 mM Tris-Cl pH 7.5. The percent starch was determined by dividing the amount (weight) of glucose by the dry weight of the callus.

For the Western blots, a portion of the dried, homogenized callus from each of the 12 samples, plus the 2 control samples, was resuspended in 200 μl of extraction buffer (100 mM Tris-Cl pH 7.1, 1 mM EDTA, 10% glycerol, 5 mM DTT, 1 mM benzamidine). Each sample was ground with an overhead stirrer, spun in a microcentrifuge for 5 minutes at full speed, and the supernatants were removed to new tubes. The protein concentration in each sample was determined by the BioRad protein assay (Lowry et al. 1951 ), with BSA as a standard. Twenty-five (25) μg of each sample was loaded onto SDS polyacrylamide gels, with a 7–17% polyacrylamide gradient. Since the samples were loaded onto two gels, the same control callus sample was loaded onto each gel. In addition, a control spiked with 10 ng of pure *E. coli* ADPglucose pyrophosphorylase was loaded onto each gel.

After electrophoresis, the gels were blotted to nitrocellulose using a PolyBlot™ apparatus from American Bionetics. The Western blots were processed according to the protocol provided by Promega. The filters were blocked with 1% BSA in TBST (10 mM Tris-Cl pH 8.0, 150 mM NaCl, and 0.05% Tween 20), for 30 minutes. Ten (10.0) ml of TBST plus 1.3 μl of the primary rabbit anti-*E. coli* ADPglucose pyrophosphorylase antibody were mixed, and the filters was incubated with this primary antibody for 30 minutes. The filters were then washed 3 times with about 50 ml of TBST per wash, for 3 washes of 5 minutes each. Ten (10.0) ml of TBST plus 1.3 μl of the secondary antibody (goat-anti-rabbit conjugated to alkaline phosphatase, Promega) was incubated with the filters for 30 minutes followed again by 3 TBST washes. The signals were visualized using the reaction of alkaline phosphatase with BCIP and NBT, and they were quantitated with a laser densitometer.

Results

| Callus Sample | % Starch | Peak Area |
|---|---|---|
| 1 | 26.9% | 0.573 |
| 2 | 4.6 | 0.170 |
| 3 | 6.4 | 0.0 |
| 4 | 12.3 | 0.344 |
| 5 | 15.3 | 0.376 |
| 6 | 11.1 | 0.314 |
| Control 2 + 10 ng | * | 0.369 |
| 7 | 5.5 | ND |
| 8 | 5.6 | 0.117 |
| 9 | 9.7 | 0.095 |
| 10 | 6.6 | 0.0 |
| 11 | 11.4 | 0.376 |
| 12 | 13.3 | 0.342 |
| Control 2 + 10 ng | * | 0.329 |
| Control 1 | 3.0 | |
| Control 2 | 3.7 | |

*The spiked samples were only used on the Western blots.
ND = not determined

The above results show the results of the quantitative starch assays and the integrated peak areas from the Western blots. The % Starch is reported as the percent of starch relative to the dry weight of the callus. The peak area is the integrated area under the peak from a densitometer scan of the corresponding sample on a Western blot. Samples 1–6 were run on one gel, and samples 7–12 were run on another gel. Control 2 was run on both blots with and without 10 ng of purified *E. coli* ADPglucose pyrophosphorylase. The unspiked samples on both gels showed no interfering bands. The spiked samples had the peak areas shown. These results demonstrate that increased ADPglucose leads to increased starch content in plant cells.

Example 2 pMON20104, as described in Example 1, has also been transformed into the Desiree potato strain using the published tuber disc transformation protocol of Sheerman and Bevan (Sheerman and Bevan 1988). Virus-free tubers of *Solanum tuberosum* var. Desiree, were peeled, washed briefly in distilled water, and surface sterilized for 15 minutes in 10% sodium hypochlorite which contained a few drops of Tween 20. The tubers were washed 6 times in sterile water, then were immersed in liquid MS medium. A sterile 1 cm diameter cork borer was used to remove sections of the tubers, and these sections were then cut with a scalpel into 1–2 mm discs. The discs were floated in 20 ml of MS medium containing Agrobacterium ASE:pMON20104. A 10 ml culture of Agrobacterium ASE:pMON20104 was spun down and resuspended in 20 ml of MS medium before use. The culture and the discs were gently shaken in a petri dish. After 20 minutes, the discs were transferred to tobacco feeder plates with 3C5ZR medium (MS salts, 1 mg/l Thiamine HCl, 0.5 mg/l nicotinic acid, 0.5 mg/l pyridoxine HCL, 3% sucrose, 5 μM zeatin riboside, and 3 μM IAA aspartic acid, pH 5.9).

After 48 hours, infected discs were put on the new plates with the same medium, but without the feeder layer, and with 500 μg/ml carbenicillin and 100 μg/ml kanamycin. The plates were sealed with parafilm and incubated at 25° C. with 16 hours of light/day. The discs were subcultured onto fresh plates every 3 weeks, and the carbenicillin concentration was lowered from 500 to 200 μg/ml after 4 weeks in culture. Developing shoots were removed and placed in large test tubes containing MS salts and R3 vitamins (1 mg/l Thiamine HCl, 0.5 mg/l nicotinic acid, 0.5 mg/l pyridoxine HCl) plus 200 μg/ml carbenicillin and 100 μg/ml kanamycin. After roots have formed, the plants are transferred to soil and are gradually hardened off.

These preliminary experiments demonstrate that recovering transgenic plants expressing the ADPGPP gene under the control of the Enhanced-CaMV35S promoter is problematic. One potato plant was produced on a sucrose containing medium, but when removed from the medium and placed in soil, it did not survive. This result is not unexpected. The Enhanced-CaMV35S promoter is a constitutive promoter and causes expression of the ADPGPP in all tissues of the plant. The constitutive expression of the ADPGPP gene most likely causes a deprivation of the sucrose supply to the growing parts of the plant due to the ADPGPP mediated conversion of sucrose to starch in the sugar exporting cells and tissues of the plant. Thus, this example illustrates the expression of ADPGPP in plant cells and the preference, in most cases, that the ADPGPP be expressed specifically in the target tissue, such as the tuber of a potato or the fruit of a tomato. One of ordinary skill in the art would be able to select from a pool of plants transformed with the Enhanced-CaMV35S promoter, a plant expressing ADPGPP within the desired range.

Example 3

Potato tissue has also been transformed to express a CTP/ADPglucose pyrophosphorylase fusion polypeptide driven by a patatin promoter. This construct causes specific expression of the ADPGPP in potato tubers and increases the level of starch in the tubers.

The vector used in the potato transformation is a derivative of the Agrobacterium mediated plant transformation vector pMON886. The pMON886 plasmid is made up of the following well characterized segments of DNA. A 0.93 kb fragment isolated from transposon Tn7 which encodes bacterial spectinomycin/streptomycin (Spc/Str) resistance and is a determinant for selection in *E. coli* and *Agrobacterium tumefaciens* (Fling et al., 1985). This is joined to a chimeric kanamycin resistance gene engineered for plant expression to allow selection of the transformed tissue. The chimeric gene consists of the 0.35 kb cauliflower mosaic virus 35S promoter (P-35S) (Odell eta[., 1985), the 0.83 kb neomycin phosphotransferase type II gene (NPTII), and the 0.26 kb 3'-nontranslated region of the nopaline synthase gene (NOS 3') (Fraley et al., 1983). The next segment is a 0.75 kb origin of replication from the RK2 plasmid (ori-V) (Stalker et al., 1981). It is joined to a 3.1 kb SalI to PvuI segment of pBR322 which provides the origin of replication for maintenance in *E. coli* (ori-322) and the bom site for the conjugational transfer into the *Agrobacterium tumefaciens* cells. Next is a 0.36 kb PvuI fragment from the pTiT37 plasmid which contains the nopaline-type T-DNA right border region (Fraley et al., 1985).

Figure 7:
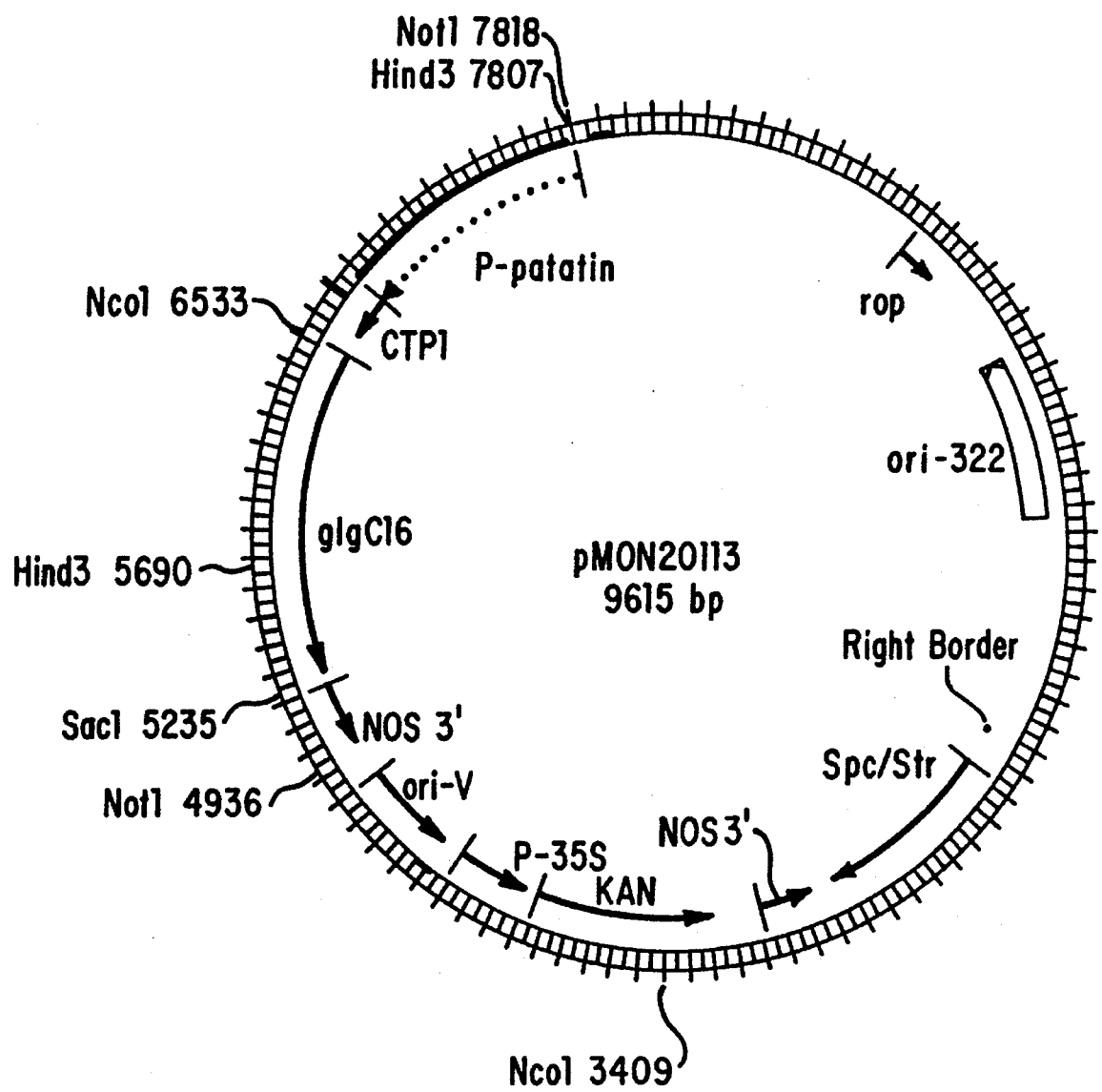
FIG. 7 shows a plasmid map for plant transformation vector pMON20113.

The glgC16 gene was engineered for expression primarily in the tuber by placing the gene under the control of a tuber-specific promoter. The GlgC16 protein was directed to the plastids within the plant cell due to its synthesis as a C-terminal fusion with a N-terminal protein portion encoding a chloroplast targeting sequence (CTP) derived from that from the SSU 1A gene from *Arabidopsis thaliana* (Timko et al., 1989). The CTP portion is removed during the import process to liberate the GlgC16 enzyme. Other plant expression signals also include the 3' polyadenylation sequences which are provided by the NOS 3' sequences located downstream from the coding portion of the expression cassette. This cassette was assembled as follows: The patatin promoter was excised from the pBI241.3 plasmid as a HindIII-BamHI fragment (The pBI241.3 plasmid contains the patatin-1 promoter segment comprising from the AccI site at 1323 to the DraI site at 2289 [positions refer to the sequence in Bevan et al., 1986] with a HindIII linker added at the former and a BamHI linker added at the latter position; Bevan et al., 1986) and ligated together with the CTP1-glgC16 fusion (the BglII-SacI fragment from pMON20102—see Example 1) and pUC-type plasmid vector cut with HindIII and SacI (these cloning sites in the vector are flanked by NotI recognition sites). The cassette was then introduced, as a NotI site in pMON886, such that the expression of the glgC16 gene is in the same orientation as that of the NPTII (kanamycin) gene. This derivative is pMON20113 which is illustrated in FIG. 7.

The pMON20113 vector was mobilized into disarmed *Agrobacterium tumefaciens* strain by the triparental conjugation system using the helper plasmid pRK2013 (Ditta et al., 1980). The disarmed strain ABI was used, carrying a Ti plasmid which was disarmed by removing the phytohormone genes responsible for crown gall disease. The ABI strain is the A208 *Agrobacterium tumefaciens* carrying the disarmed pTiC58 plasmid pMP90RK (Koncz and Schell, 1986). The disarmed Ti plasmid provides the trfA gene functions required for autonomous replication of the pMON vector after the conjugation into the ABI strain. When the plant tissue is incubated with the ABI::pMON conjugate, the vector is transferred to the plant cells by the vir functions encoded by the disarmed pMP90RK Ti plasmid.

The pMON20113 construct is then transformed into the Russet Burbank potato variety. To transform Russet Burbank potatoes, sterile shoot cultures of Russet Burbank are maintained in sundae cups containing 8 ml of PM medium supplemented with 25 mg/L ascorbic acid (Murashige and Skoog (MS) inorganic salts, 30 g/l sucrose, 0.17 g/l $NaH_2PO_4H_2O$, 0.4 mg.l thiamine-HCl, and 100 mg/l myo-inositol, solidified with 2 g/l Gelrite at pH 6.0). When shoots reach approximately 5 cm in length, stem internode segments of 3–5 mm are excised and inoculated with a 1:10 dilution of an overnight culture of *Agrobacterium tumefaciens* from a 4 day old plate culture. The stem explants are co-cultured for 2 days at 20° C. on a sterile filter paper placed over 1.5 ml of a tobacco cell feeder layer overlaid on 1/10 P medium (1/10 strength MS inorganic salts and organic addenda without casein as in Jarret et al. (1980), 30 g/l sucrose and 8.0 g/l agar). Following co-culture, the explants are transferred to full strength P-1 medium for callus induction, composed of MS inorganic salts, organic additions as in Jarret et al. (1980), with the exception of casein, 5.0 mg/l zeatin riboside (ZR), and 0.10 mg/l naphthaleneacetic acid NAA (Jarret et al., 1980a, 1980b). Carbenicillin (500 mg/l) and cefotaxime (100 mg/L) are included to inhibit bacterial growth, and 100 mg/l kanamycin is added to select for transformed cells. Transformed potato plants expressing the patatin promoter—CTP/ADP-glucose pyrophosphorylase—NOS gene show an increased starch content in the tuber.

After 4 weeks, the explants are transferred to medium of the same composition, but with 0.3 mg/l gibberellic acid (GA3) replacing the NAA (Jarret et al., 1981) to promote shoot formation. Shoots begin to develop approximately 2 weeks after transfer to shoot induction medium. These shoots are excised and transferred to vials of PM medium for rooting. After about 4 weeks on the rooting medium, the plants are transferred to soil and are gradually hardened off.

Shoots are tested for kanamycin resistance conferred by the enzyme neomycin phosphotransferase II, by placing the shoots on PM medium for rooting, which contains 50 mg/L kanamycin, to select for transformed cells.

Russet Burbank Williams plants regenerated in culture were transplanted into 6 inch (~15.24 cm) pots and were grown to maturity under greenhouse conditions. Tubers were harvested and were allowed to suberize at room temperature for two days. All tubers greater than 2 cm. in length were collected and stored at 9° C. under high humidity.

Specific gravity (SG) was determined 3 days after harvest for the largest 2 or 3 tubers front each plant, with typical weights being 20–40 grams per tuber. Specific gravity calculations were performed by the weight in air less weight in water method, where SG=weight in air/(weight in air−weight in water). Calculations for percent starch and percent dry matter based on SG were according to the following formulas (von Scheelem, 1937):

% starch=17.546+(199.07)(SG−1.0988)

% dry matter=24.182+(211.04)(SG−1.0988).

Western blot analysis was performed on protein extracted from fresh, center sections of tuber tissue as described for tomato leaf tissue. Starch analysis was performed on similar fresh tuber sections as described (Lin, 1988a). Briefly, approximately 300 mg. center sections were cut, placed in 1.5 ml centrifuge tubes, and frozen on dry ice. The tissue was then dried to a stable weight in a Savant Speed-Vac Concentrator, and final dry weight was determined. Starch content was determined using approximately 60 mg. of dry material from each tuber. Soluble sugars were first removed by extracting three times with 1 ml of 80% ethanol at 70° C., for 20 minutes per treatment. After the final incubation, all remaining ethanol was removed by desiccation in a Speed Vac Concentrator. The solid material was resuspended in 400 μl 0.2M potassium hydroxide, ground, and then incubated for 30 minutes at 100° C. to solubilize the starch. The solutions were cooled and neutralized by addition of 80 μl 1N acetic acid. Starch was degraded to glucose by treatment with 14.8 units of pancreatic alpha-amylase (Sigma Chemical, St. Louis) for 30 minutes at 37° C., followed by 10 units of amyloglucosidase (Sigma Chemical, St. Louis) for 60 minutes at 55° C. Glucose released by the enzymatic digestions was measured using the Sigma Chemical (St. Louis) hexokinase kit.

Western blot and quantitative starch analyses were performed on center cuts from tubers generated under standard greenhouse conditions. Tubers from potato plants expressing E. coli ADPGPP contain on average 26.4% higher levels of starch than controls. The range of individual data points shows that two distinct populations exist with respect to starch content. One population, represented by the control tubers, range in starch content from 10.2% up to 15%, with an average starch content of 12.67%. The second population represents expressors of E. coli ADPGPP, which range in starch content from 12.1% up to 19.1%, with an average of 16%. The observed increase in starch content correlated with expression levels of E. coli ADPGPP, demonstrating that this expression leads to an increase in starch content in potato tubers.

Specific gravity was determined for the largest 2 or 3 tubers from each of 36 independent transformants by the weight in air less weight in water method (Kleinkopf, 1987). The data show that tubers expressing E. coli ADPGPP had a significant increase in specific gravity compared to controls. On average, the specific gravity increased from 1.068 in control tubers up to 1.088 in transgenic tubers (Table 1a), with the best lines averaging specific gravities of about 1.100. Specific gravity values varied among tubers of the same plant, as well as between tubers from different plants, as expected. However, only lines expressing E. coli ADPGPP produced tubers with elevated specific gravities, and these increases roughly correlated with the levels of glgC16 expression. Starch and dry matter content increased on average 35.0% and 23.9% respectively in tubers expressing E. coli ADPGPP, with the best lines containing approximately 59.3% and 40.6% increases, respectively.

The starch content determined by the glucose method for a total of 26 potato lines was compared with the starch content calculated for these same tubers using specific gravity measurements. The levels of starch as calculated from specific gravity were in good agreement with that determined directly (Table 1b). For example, tubers expressing E. coli ADPGPP contained 16.01% starch as determined by quantitative analysis versus 16.32% as determined by specific gravity. When increases in individual lines were examined, the experimentally determined starch content strongly correlated with the observed increase in dry matter (and expression of the glgC16 gene). Therefore, the observed increase in dry matter content in tubers expressing E. coli ADPGPP is largely due to the increased deposition of starch.

TABLE 1

| a) | | Average Specific Gravity | Average % Starch | Average % Dry Matter |
| --- | --- | --- | --- | --- |
| E. coli ADPGPP+ | (15) | 1.088 (0.012) | 15.40 | 21.90 |
| Controls | (21) | 1.068 (0.010) | 11.41 | 17.68 |

The number of plants tested is indicated in parenthesis, with two or three tubers per plant being weighed. Sample standard deviation follows specific gravity (in parenthesis). Percent starch and dry matter were calculated from the average specific gravity as described. Controls consist of a combination of tubers transformed to contain only the DNA vector, without the glgC16 gene, and tubers from the glgC16 transformation event which do not express E. coli ADPGPP.

| (b) | | Avg % Starch Specific Gravity | Avg % Starch Enzymatic |
| --- | --- | --- | --- |
| E. coli ADPGPP+ | (11) | 16.32 (1.47) | 16.01 (2.00) |
| Controls | (15) | 11.96 (1.37) | 12.67 (1.33) |

Average values for percent starch determined experimentally by enzymatic degradation to starch content and calculated from specific gravity measurements. Sample standard deviations are in parenthesis. Differences between E. coli ADPGPP+ and controls, calculated by specific gravity or enzymatic methods, are significant at >0.005 level of significance by the Student T-test.

Example 4

The enzyme ADPGPP is encoded by a single gene in *E. coli* (glgC), whose active form functions as a homotetramer (Preiss, 1984), while the plant enzyme is a heterotetramer encoded by at least two different genes (Copeland and Preiss, 1981). Both *E. coli* and plant ADPGPP's are subject to tight regulation, with the bacterial enzyme being activated by fructose 1,6-bisphosphate and inhibited by AMP (Preiss, 1984), while the plant enzymes are activated by 3-phosphoglycerate and inhibited by $P_i$ (Copeland and Preiss, 1981; Preiss, 1984). Several mutants of *E. coli* ADPGPP have been characterized and the kinetic properties of a few are summarized and compared in Table 2. (Romeo, T. and Preiss, J., 1989).

TABLE 2

| Strain | Glycogen accumulation (mg/g cells) | Fructose 1,6-bisphosphate $A_{0.5}$ (µM) | AMP $I_{0.5}$ (µM) |
| --- | --- | --- | --- |
| wild type | 20 | 68 | 75 |
| SG5 | 35 | 22 | 170 |
| CL1136 | 74 | 5.2 | 680 |
| 618 | 70 | 15 | 860 |

It has been demonstrated that expression of the glgC16 variant, found in *E. coli* strain 618, leads to enhanced starch biosynthesis in plant cells. Expression of other bacterial ADPGPP enzymes in plant cells also enhance starch content.

Figure 8:
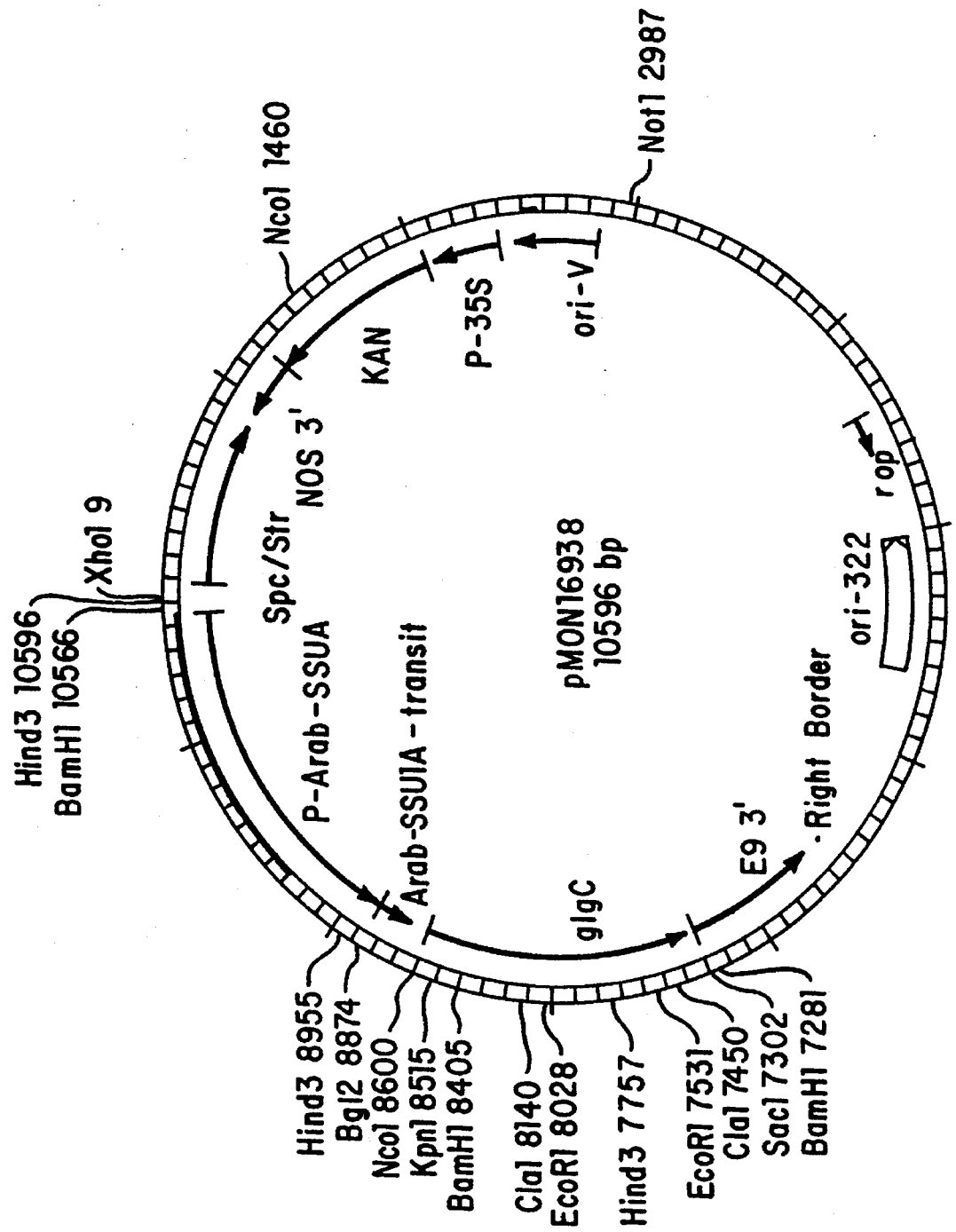
FIG. 8 shows a plasmid map for plant transformation vector pMON16938.
Figure 9:
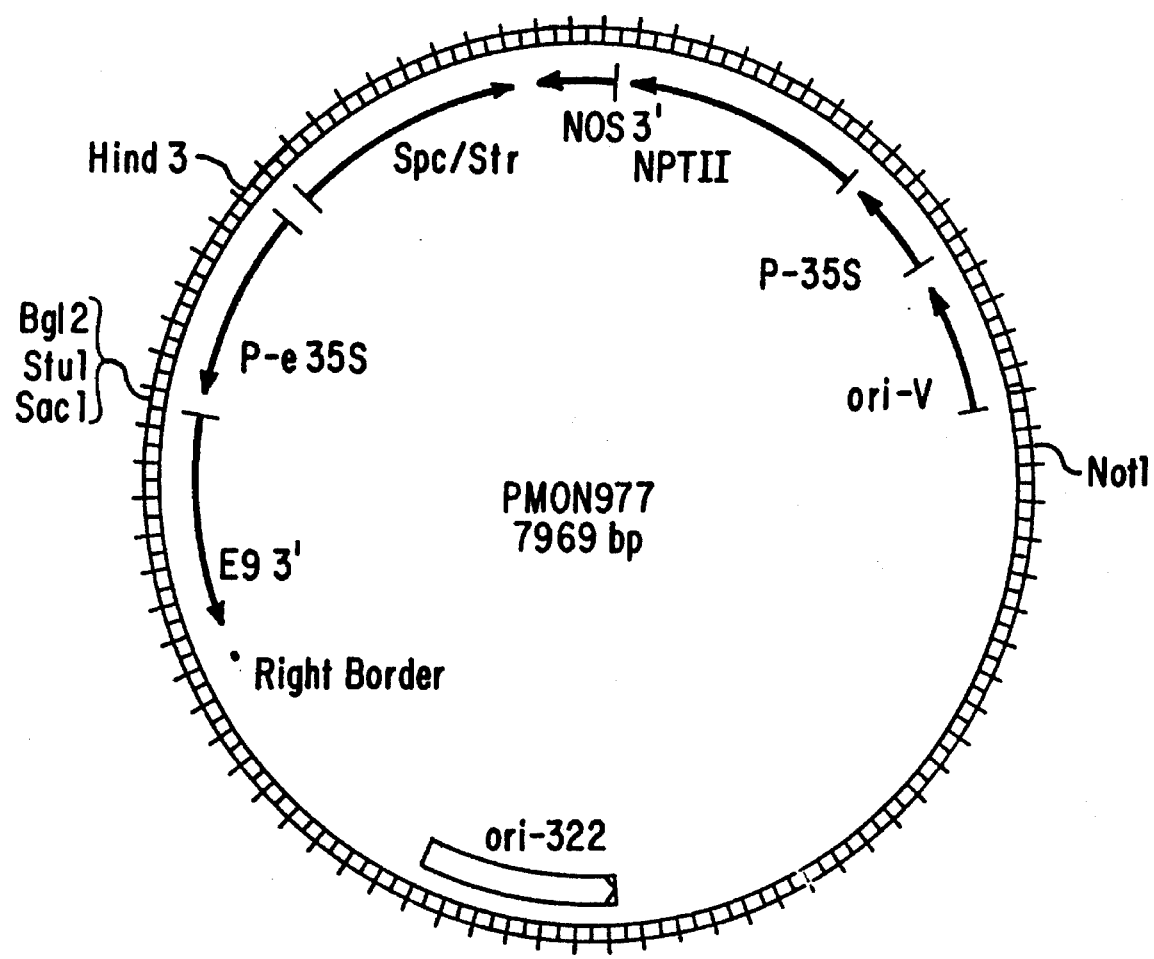
FIG. 9 shows a plasmid map for plant transformation vector pMON977.

Expression of the wild type glgC gene also leads to increased starch content. The wild type glgC gene, contained on an *E. coli* genomic clone designated pOP12 (Okita et al., 1981) was isolated in a manner similar to that described for the isolation of the glgC16 gene described in Example 1. Briefly, an NcoI site was introduced at the 5' translational start site and a SacI site was introduced just 3' of the termination codon by the PCR reaction using the QSP3 and QSM10 primers described in Example 1. The resultant NcoI-SacI fragment was ligated into the vector pMON20102 (described in Example 1) previously digested with NcoI and SacI, giving the plasmid pMON16937. The PSsu-glgC chimeric gene was constructed by ligating an XhoI-BglII restriction fragment containing the Ssu1A promoter (Timko et al., 1985), the BglII-SacI fragment from pMON16937 comprising the CTP1-glgC gene, and the plant transformation vector pMON977 digested with XhoI and SacI, to form pMON16938 (FIG. 8). The pMON977 plasmid contains the following well characterized DNA segments (FIG. 9). First, the 0.93 Kb fragment isolated from transposon Tn7 which encodes bacterial spectinomycin/streptomycin resistance (Spc/Str), and is a determinant for selection in *E. coli* and *Agrobacterium tumefaciens* (Fling et al., 1985). This is joined to the chimeric kanamycin resistance gene engineered for plant expression to allow selection of the transformed tissue. The chimeric gene consists of the 0.35 Kb cauliflower mosaic virus 35S promoter (P-35S)(Odell et al., 1985), the 0.83 Kb NPTII gene, and the 0.26 Kb 3'-nontranslated region of the nopaline synthase gene (NOS 3') (Fraley et al., 1983). The next segment is the 0.75 Kb origin of replication rom the RK2 plasmid (off-V) (Stalker et al., 1981). This is joined to the 33.1 Kb SalI to PvuI fragment from pBR322 which provides the origin of replication for maintenance in *E. coli* (ori-322), and the bom site for the conjugational transfer into the *Agrobacterium tumefaciens* cells. Next is the 0.36 Kb PvuI to BclI fragment from the pTiT37 plasmid, which contains the nopaline-type T-DNA right border region (Fraley et al., 1985). The last segment is the expression cassette consisting of the 0.65 Kb cauliflower mosaic virus (CaMV) 35S promoter enhanced by duplication of the promoter sequence (P-E35S) (Kay et al., 1987), a synthetic multilinker with several unique cloning sites, and the 0.7 Kb 3' nontranslated region of the pea rbcS-E9 gene (E9 3') (Coruzzi et al., 1984; Morelli et al., 1985). The plasmid was mated into *Agrobacterium tumefaciens* strain ABI, using the triparental mating system, and used to transform *Lycopersicon esculentum* cv. UC82B.

Tomato plant cells are transformed utilizing the Agrobacterium strains described above generally by the method as described in McCormick et al. (1986). In particular, cotyledons are obtained from 7–8 day old seedlings. The seeds are surface sterilized for 20 minutes in 30% Clorox bleach and are germinated in Plantcons boxes on Davis germination media. Davis germination media is comprised of 4.3 g/l MS salts, 20 g/l sucrose and 10 ml/l Nitsch vitamins, pH 5.8. The Nitsch vitamin solution is comprised of 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds are allowed to germinate for 7–8 days in the growth chamber at 25° C., 40% humidity under cool white lights with an intensity of 80 einsteins $m^{-2}s^{-1}$. The photoperiod is 16 hours of light and 8 hours of dark.

Once germination has occurred, the cotyledons are explanted using a #15 feather blade by cutting away the apical meristem and the hypocotyl to create a rectangular explant. These cuts at the short ends of the germinating cotyledon increase the surface area for infection. The explants are bathed in sterile Davis regeneration liquid to prevent desiccation. Davis regeneration media is composed of 1× MS salts, 3% sucrose, 1× Nitsch vitamins, 2.0 mg/l zeatin, pH 5.8. This solution is autoclaved with 0.8% Noble Agar.

The cotyledons are pre-cultured on "feeder plates" composed of Calgene media containing no antibiotics. Calgene media is composed of 4.3 g/l MS salts, 30 g/l sucrose, 0.1 g/l myo-inositol, 0.2 g/l $KH_2PO_4$, 1.45 ml/l of a 0.9 mg/ml solution of thiamine HCl, 0.2 ml of a 0.5 mg/ml solution of kinetin and 0.1 ml of a 0.2 mg/ml solution of 2,4 D, this solution is adjusted to pH 6.0 with KOH. These plates are overlaid with 1.5–2.0 ml of tobacco suspension cells (TXD's) and a sterile Whatman filter which is soaked in 2COO5K media. 2COO5K media is composed of 4.3 g/l Gibco MS salt mixture, 1 ml B5 vitamins (1000× stock), 30 g/l sucrose, 2 ml/l PCPA from 2 mg/ml stock, and 10 µl/l kinetin from 0.5 mg/ml stock. The cotyledons are cultured for 1 day in a growth chamber at 25° C. under cool white lights with a light intensity of 40–50 einsteins $m^{-2}s^{-1}$ with a continuous light photoperiod.

Cotyledons are then inoculated with a log phase solution of Agrobacterium containing the plasmid pMON 16938. The concentration of the Agrobacterium is approximately $5×10^8$ cells/mi. The cotyledons are allowed to soak in the bacterial solution for six minutes and are then blotted to remove excess solution on sterile Whatman filter disks and are subsequently replaced to the original feeder plate where they are allowed to co-culture for 2 days. After the two days, cotyledons are transferred to selection plates containing Davis regeneration media with 2 mg/l zeatin riboside, 500 µg/ml carbenicillin, and 100 µg/ml kanamycin. After 2–3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds will continue to regenerate. Shoots develop within 3–4 months.

Once shoots develop, they are excised cleanly from callus tissue and are planted on rooting selection plates. These plates contain 0.5× MSO containing 50 μg/ml kanamycin and 500 μg/ml carbenicillin. These shoots form roots on the selection media within two weeks. If no shoots appear after 2 weeks, shoots are trimmed and replanted on the selection media. Shoot cultures are incubated in percivals at a temperature of 22° C. Shoots with roots are then potted when roots are about 2 cm in length. The plants are hardened off in a growth chamber at 21° C. with a photoperiod of 18 hours light and 6 hours dark for 2–3 weeks prior to transfer to a greenhouse. In the greenhouse, the plants are grown at a temperature of 26° C. during the day and 21° C. during the night. The photoperiod is 13 hours light and 11 hours dark and allowed to mature.

Transgenic tomato plants transformed with pMON16938 were generated and screened by Western blot analysis for the glgC gene product. For Western blot analysis, proteins were extracted from leaf or stem tissue by grinding 1:1 in 100 mM Tris pH 7.5, 35 mM KCl, 5 mM dithiothreitol, 5 mM ascorbate, 1 mM EDTA, 1 mM benzamidine, and 20% glycerol. The protein concentration of the extract was determined using the Pierce BCA method, and proteins were separated on 3–17% SDS polyacrylamide gels. $E.\ coli$ ADPGPP was detected using goat antibodies raised against purified $E.\ coli$ ADPGPP and alkaline phosphatase conjugated rabbit anti-goat antibodies (Promega, Madison, Wis.). In most plants expressing wild type $E.\ coli$ ADPGPP, levels of $E.\ coli$ ADPGPP were on 0.1% of the total extractable protein. For starch analysis, single leaf punches were harvested during late afternoon from 3–4 different, young, fully-expanded leaves per greenhouse grown plant. The leaf punches from each plant were combined and fresh weights were determined using a Mettler analytical balance. Total fresh weight per sample ranged from 60–80 mg. Soluble sugars were first removed by extracting three times with 1 ml of 80% ethanol at 70° C. for 20 minutes per treatment. After the final incubation, all remaining ethanol was removed by desiccation in a Speed Vac Concentrator. The solid material was resuspended in 400 μl 0.2M potassium hydroxide, ground, and then incubated for 30 minutes at 100° C. to solubilize the starch. The solutions were cooled and then neutralized by addition of 80 μl 1N acetic acid. Starch was degraded to glucose by treatment with 14.8 units of pancreatic alpha-amylase (Sigma Chemical, St. Louis) for 30 minutes at 37° C., followed by 10 units of amyloglucosidase (Sigma Chemical, St. Louis) for 60 minutes at 55° C. Glucose released by the enzymatic digestions was measured using the Sigma Chemical (St. Louis) hexokinase kit, and these values were used to calculate starch content.

Leaves from tomato plants expressing the glgC gene from the Ssu promoter contain higher levels of starch than controls, with the best line showing a 107% increase (Table 3).

TABLE 3

|  |  | Average % Starch | Standard Deviation |
|---|---|---|---|
| $E.\ coli$ ADPGPP+ | (14) | 9.3 | 1.8 |
| Controls | (10) | 8.4 | 2.7 |

The number of lines screened are in parentheses.
Thus, other ADPGPP's with different kinetic properties are also effective in increasing starch content in transgenic plants. It should be noted that high level expression of unregulated ADPGPP mutants in leaf tissue is undesirable since it will cause adverse effects on growth and development of the plants. In fact, use of the glgC16 gene in place of glgC in the above experiments did not result in regeneration of transformants expressing high levels of the glgC16 gene product.

Figure 10:
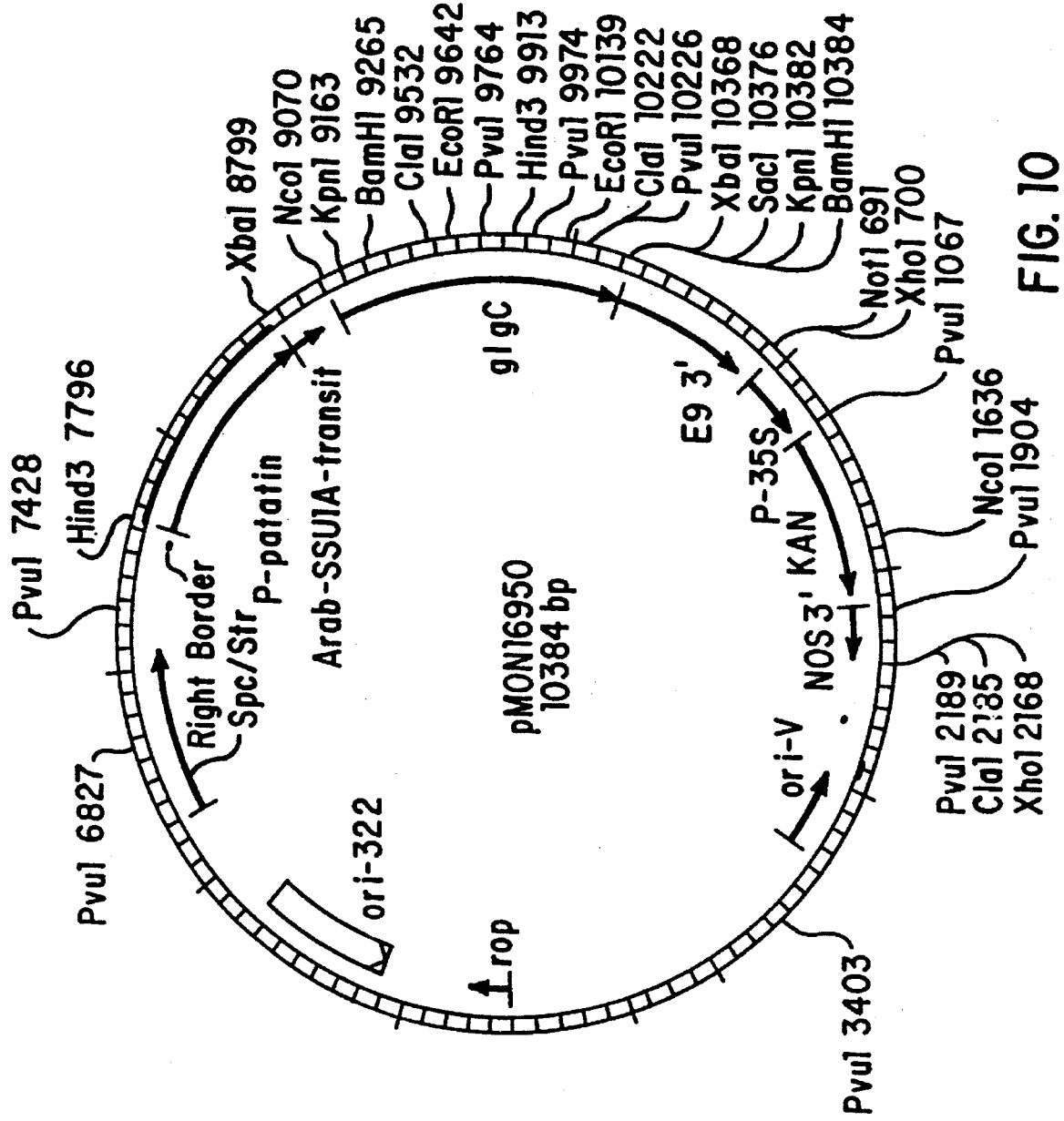
FIG. 10 shows a plasmid map for plant transformation vector pMON16950.
Figure 11:
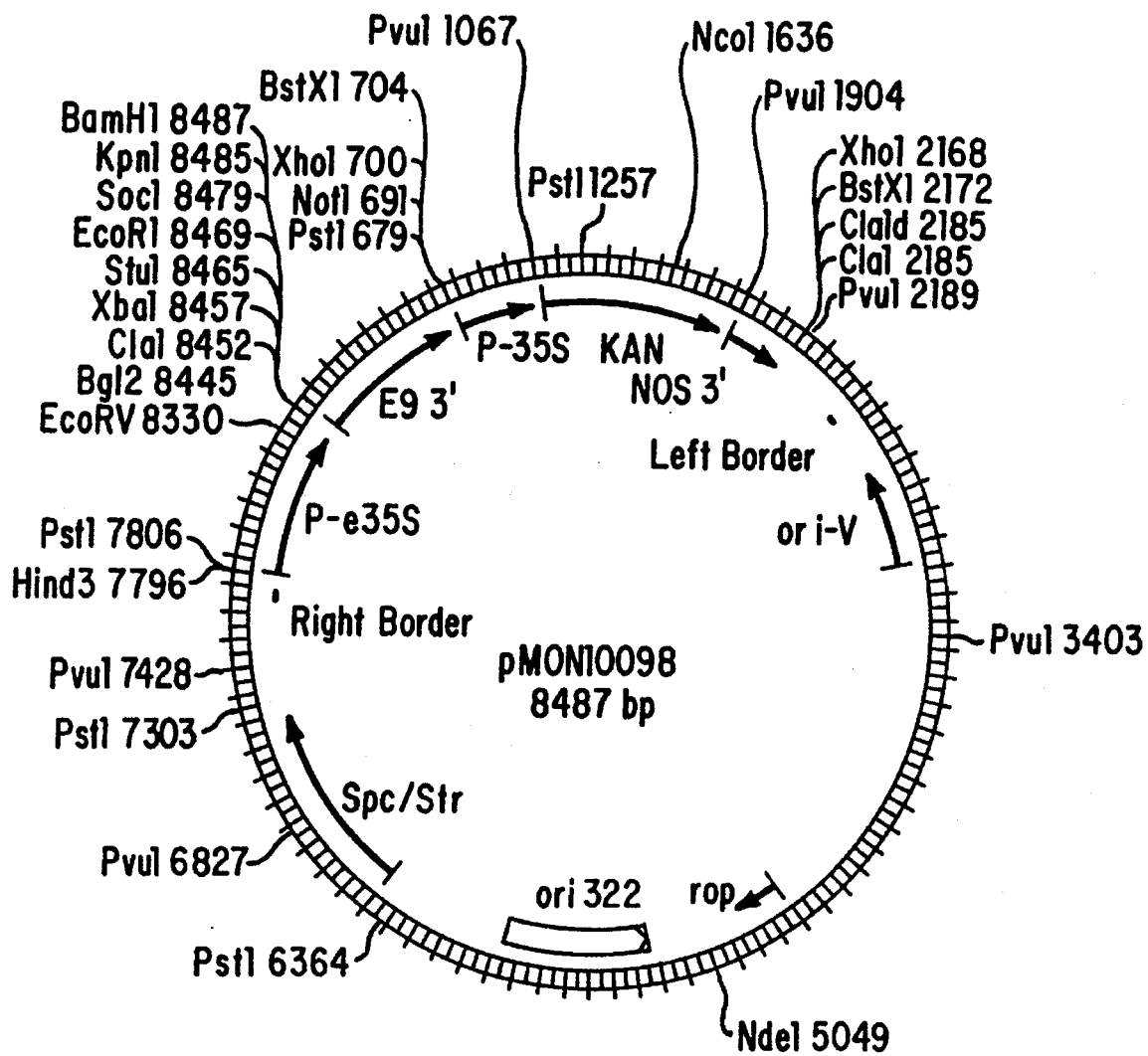
FIG. 11 shows a plasmid map for plant transformation vector pMON10098.

To express glgC from the patatin promoter, the same BglII-SacI CTP1-glgC fragment from pMON16937 and a HindIII-BamHI fragment containing the patatin promoter from the plasmid pBI241.3 were ligated into the binary vector pMON10098 (FIG. 11), digested with HindIII and SacI, to give the plasmid pMON16950 (FIG. 10) The pBI241.3 plasmid contains the patatin-1 promoter segment comprising from the AccI site at 1323 to the DraI site at 22389 [positions refer to the sequence in Bevan et al., 1986] with a HindIII linker added at the latter position. The pMON10098 plasmid contains the following DNA regions, moving clockwise around FIG. 11. 1) The chimeric kanamycin resistance gene engineered for plant expression to allow selection of the transformed tissue. The chimeric gene consists of the 0.35 Kb cauliflower mosaic virus 35S promoter (P-35S) (Odell et al., 1985), the 0.83 Kb NPTII gene, and the 0.26 Kb 3'-nontranslated region of the NOS 3'; 2) The 0.45 Kb ClaI to the DraI fragment from the pTi15955 octopine Ti plasmid, which contains the T-DNA left border region (Barker et al., 1983); 3) The 0.75 Kb segment containing the origin of replication from the RK2 plasmid (off-V) (Stalker et al., 1981); 4) The 3.0 Kb SalI to PstI segment of pBR322 which provides the origin of replication for maintenance in $E.\ coli$ (ori-322), and the bom site for the conjugational transfer into the $Agrobacterium\ tumefaciens$ cells; 5) The 0.93 Kb fragment isolated from transposon Tn7 which encodes bacterial spectinomycin/streptomycin resistance (Spc/Str) (Fling et al., 1985), and is a determinant for selection in $E.\ coli$ and $Agrobacterium\ tumefaciens$; 6) The 0.36 Kb PvuI to BclI fragment from the pTiT37 plasmid, which contains the nopaline-type T-DNA right border region (Fraley et al., 1985); and 7) The last segment is the expression cassette consisting of the 0.65 Kb cauliflower mosaic virus (CaMV) 35S promoter enhanced by duplication of the promoter sequence (P-E35S) (Kay et al., 1987), a synthetic multilinker with several unique cloning sites, and the 0.7 Kb 3' nontranslated region of the pea rbcS-E9 gene (E9 3') (Coruzzi et al., 1984; Morelli et al., 1985). The plasmid was mated into $Agrobacterium\ tumefaciens$ strain ABI, using the triparental mating system, and used to transform Russet Burbank line Williams 82. Expression of glgC from the patatin promoter (pMON16950) in potato also results in enhanced starch content in tubers.

In a manner similar to that described for the wild type glgC gene and for the glgC16 mutant gene, the mutant glgC-SG5 was also, expressed in plants and results in an enhancement of starch content.

Example 5

Additional promoters have been used to test the expression pattern of the glgC16 gene in potato tubers. These are a 3.5 kb patatin promoter (which includes the 1.0 kb promoter region used in Example 3), a small subunit ADPGPP promoter, two different large subunit ADPGPP promoters from Russet Burbank and Desiree varieties), and the promoter for the granule-bound starch synthesis gene of potato (GBSS).

Figure 14:
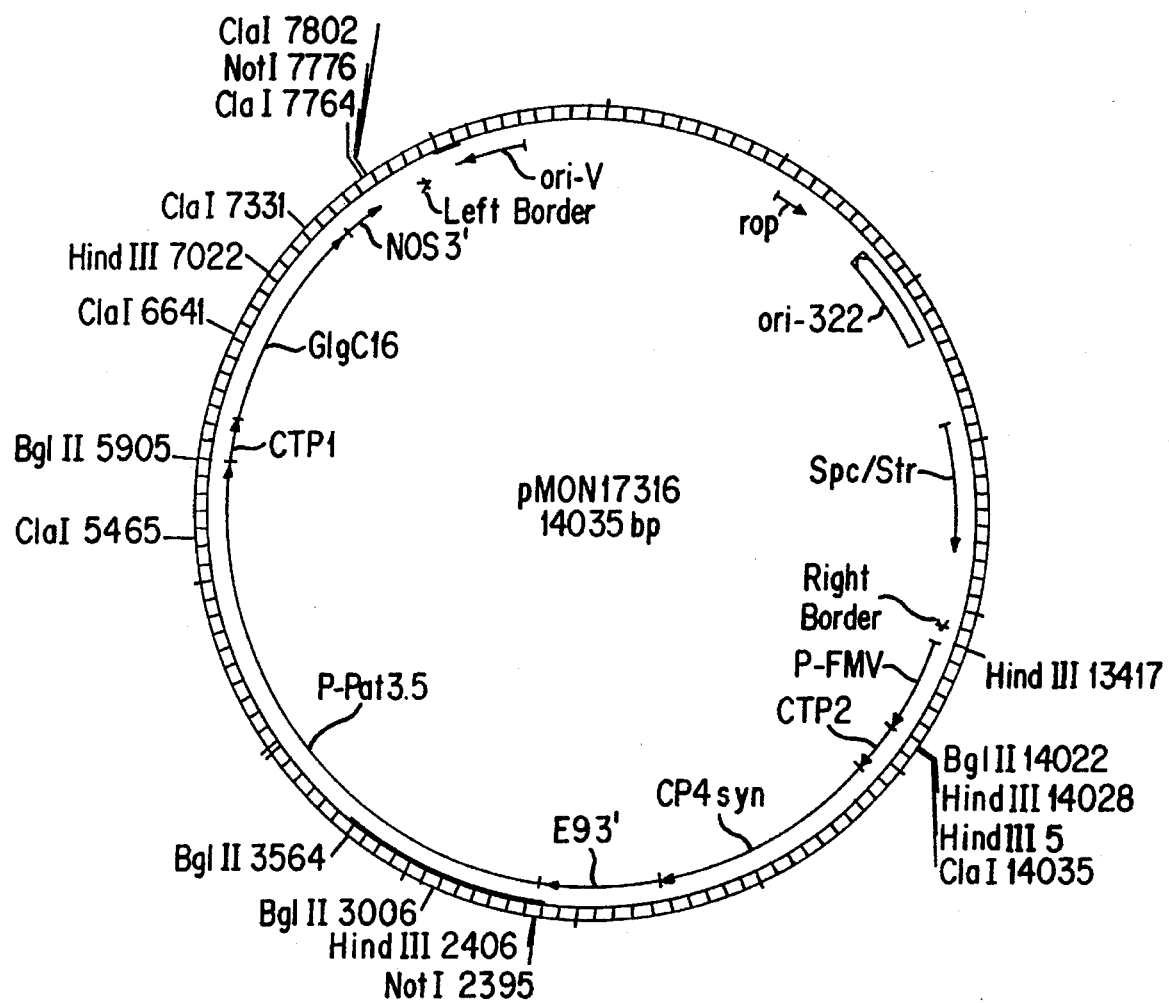
FIG. 14 shows a plasmid map for plant transformation vector pMON 17316.

The patatin 3.5 promoter was obtained from the plasmid pPBI240.7 (Bevan, 1986). The majority of the 3.5 promoter was excised from pPBI240.7, from the HindIII site (−3500) to the XbaI site at −337, and combined with the remainder of the promoter, from the XbaI site to a BglII site at +22 (formerly a DraI site), in a triple ligation into a vector which provided a BglII site to form pMON17280. This latter plasmid then served as the vector for the triple ligation of the complete 3.5 promoter and the plastid target peptide-GlgC16 fusion from pMON20102, described above to form the tuber expression cassette (in pMON17282). This cassette, consisting of the patatin 3.5 promoter, the plastid target peptide-GlgC16 fusion, and the NOS 3' sequences, was introduced into the plant transformation vector pMON17227, a Ti plasmid vector disclosed and described by Barry et al. in WO 92/04449 (1991), incorporated herein by reference, on a NotI fragment to form pMON17316. See FIG. 14.

Figure 12:
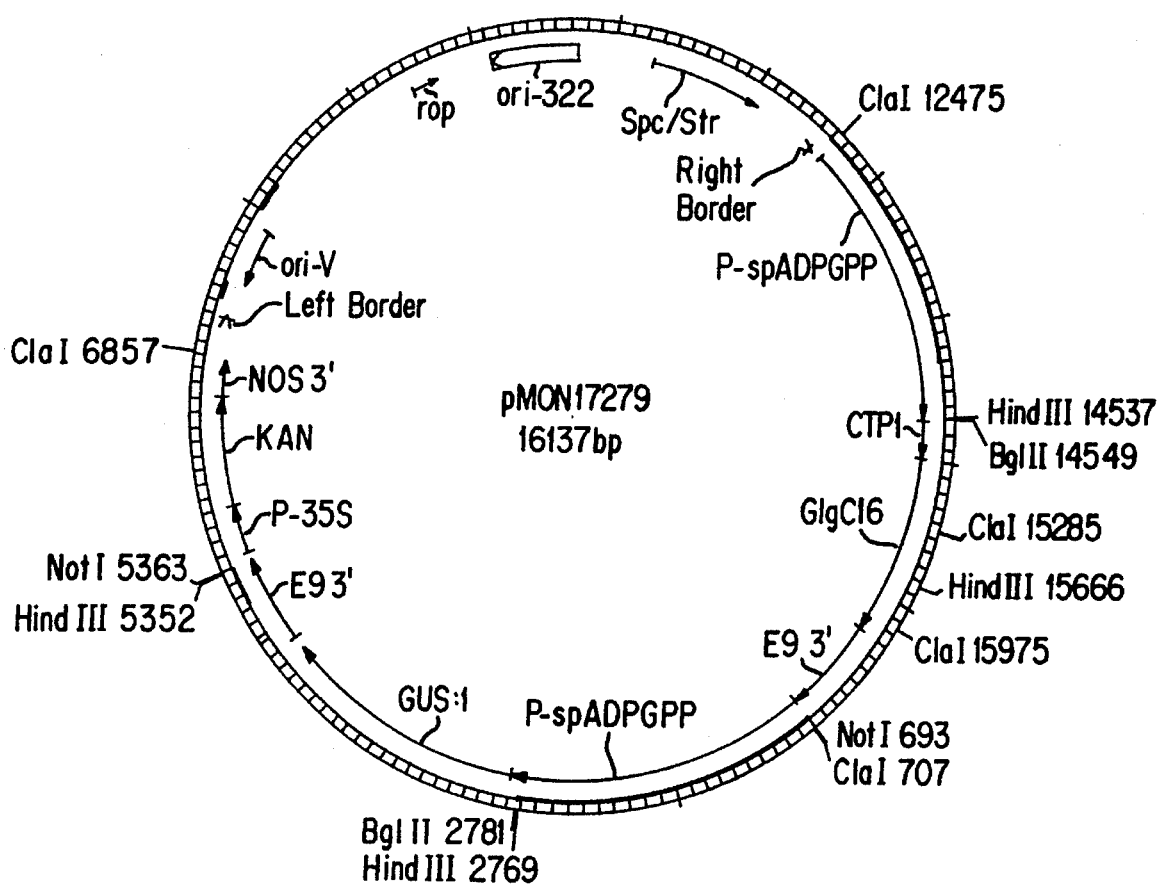
FIG. 12 shows a plasmid map for plant transformation vector pMON17279.
Figure 13:
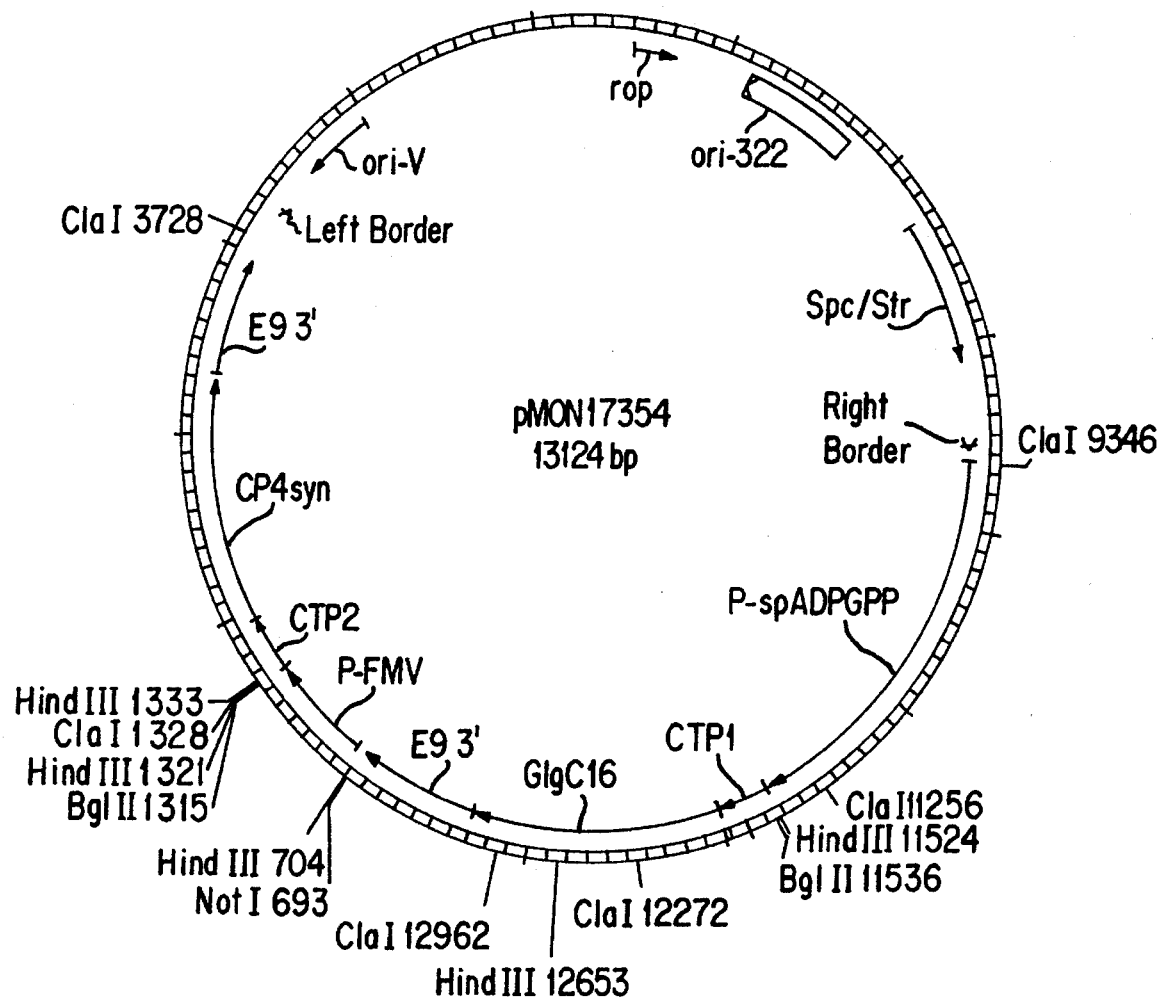
FIG. 13 shows a plasmid map for plant transformation vector pMON 17354.

The promoter for the potato tuber ADPGPP small subunit gene, SEQ ID NO:29, (Nakata et al., 1992) was obtained as a XbaI-BglII fragment of the genomic clone 1–2 and inserted into the XbaI and BamHI site of Bluescript II KS-. The promoter fragment used consists of the portion from the ClaI site about 2.0 kb extending from the putative initiating methionine to the HindIII site located 12 bp before this ATG. A BglII site was placed adjacent to this HindIII site by subcloning through another pUC vector, and was linked through this latter site to the fusion of the CTP targeting and the glgC16 coding sequences. This cassette, with a NOS 3' sequence, was introduced into two vectors to provide differing transformation selection markers. pMON17279 contains both GUS and the NPTII (kanamycin) selection cassettes and pMON17354 contains the glyphosate selection cassette as in pMON17227, described above. See FIGS. 12 and 13.

The promoter for the potato granule bound starch synthase (GBSS) gene (SEQ ID NO:26) was isolated from Russet Burbank DNA by PCR based on the sequence published by Rohde et al. (1990). PCR primers were designed to introduce a HindIII cloning site at the 5' end of the promoter, and a BglII site downstream of the transcription start site. The resultant 1.2 Kb promoter fragment was ligated into pMON10098 in place of the E35S promoter, and fused with a BglII-SacI fragment containing the CTP1-glgC16 chimeric gene of pMON20102. The E35S-NPT II-Nos cassette was removed from this plasmid and replaced with a NotI-SalI fragment of pMON17227, containing the FMV-CTP2-CP4-E9 cassette which confers glyphosate tolerance in plants, resulting in the plasmid pMON16996.

Promoters for the large subunit of potato tuber ADPGPP were isolated from two varieties of potato, Russet Burbank (SEQ ID NO:24) and Desiree (SEQ ID NO:25). The clones were identified using plaque hybridization with a probe from the 5' end of a cDNA from the large subunit of ADPglucose pyrophosphorylase. The translational start sites (ATG) of these clones were identified by plant consensus (Lutcke et al., 1987). PCR primers were used to introduce an BAMHI site at the 3' end downstream of the ATG and a HINDIII site at the 5' end of both promoters. The resulting 600 bp Russet Burbank promoter and 1600 bp Desiree promoters were ligated independently into pMON10098 in place of the E35S promoter, and fused with a BglII-SacI fragment from pMON20102 containing CTP-glgC16 chimeric gene. The E35S-NPTII-Nos cassette was removed from these plasmids and replaced with a NotI- SalI fragment containing the FMV-CTP-CP4-E9 cassette of pMON17227, discussed above, resulting in pMON21522 (Russet Burbank) and pMON21523 (Desiree).

Figure 18:
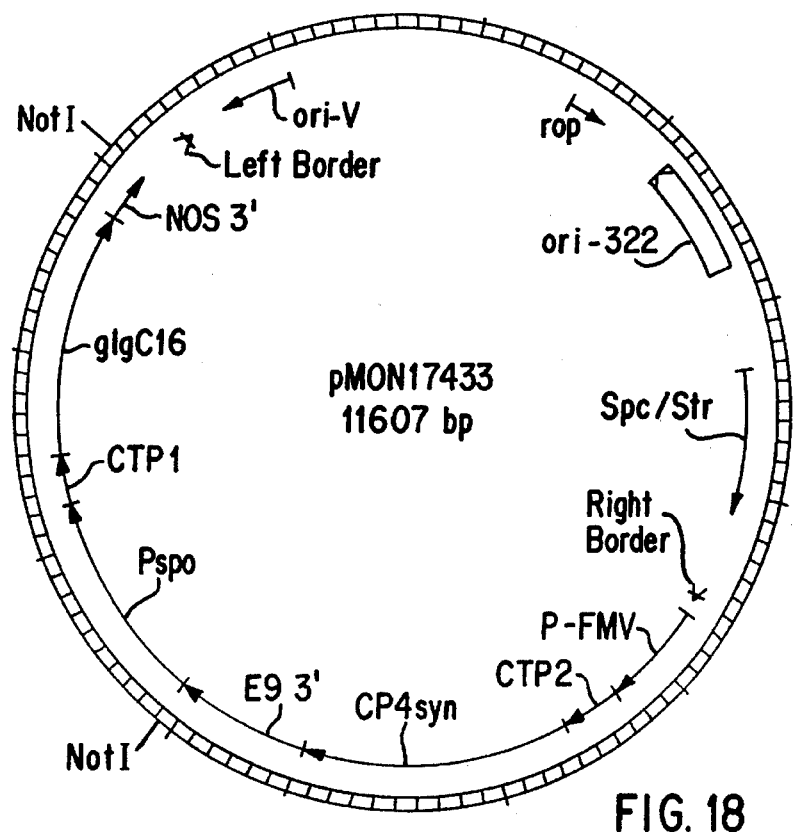
FIG. 18 shows a plasmid map for plant transformation vector pMON 17433.

The promoter for the sporamin gene was isolated from sweet potato DNA by PCR based on the gSPO-A1 sequence published by Hattori and Nakamura (1988). A HindIII cloning site was engineered at the 5' end of the promoter, and a BglII site was engineered at the 3' end. Approximately 12 pmoles of the primers were added to an amplification using Taq DNA polymerase (Perkin Elmer Cetus) and the manufacturers recommended conditions. The following temperature profile was used for the amplification: 5 cycles of 94° C. 0.5 min, 65° C. 1 min, 72° C. 1.5 min; 5 cycles of 94° C. 0.5 min, 60° C. 1 min, 72° C. 1.5 min; 10 cycles of 94° C. 0.5 min, 55° C. 1 min, 72° C. 1.5 min; and 10 cycles of 94° C. 0.5 min, 50° C. 1 min, 72° C. 1.5 min. The template for the reaction was 130 ng of sweet potato DNA. The amplification yielded a band of the correct size which was cloned as a HindIII/ BglII fragment into pMON999 in place of the E35S promoter, and fused with a BglII / SacI fragment containing the CTP1-GlgC16 chimeric gene. The resultant NotI fragment containing the Pspo-CTP1-GlgC16-Nos cassette was cloned into the NotI site of pMON17227 resulting in the plasmid pMON17433. See FIG. 18.

Figure 19:
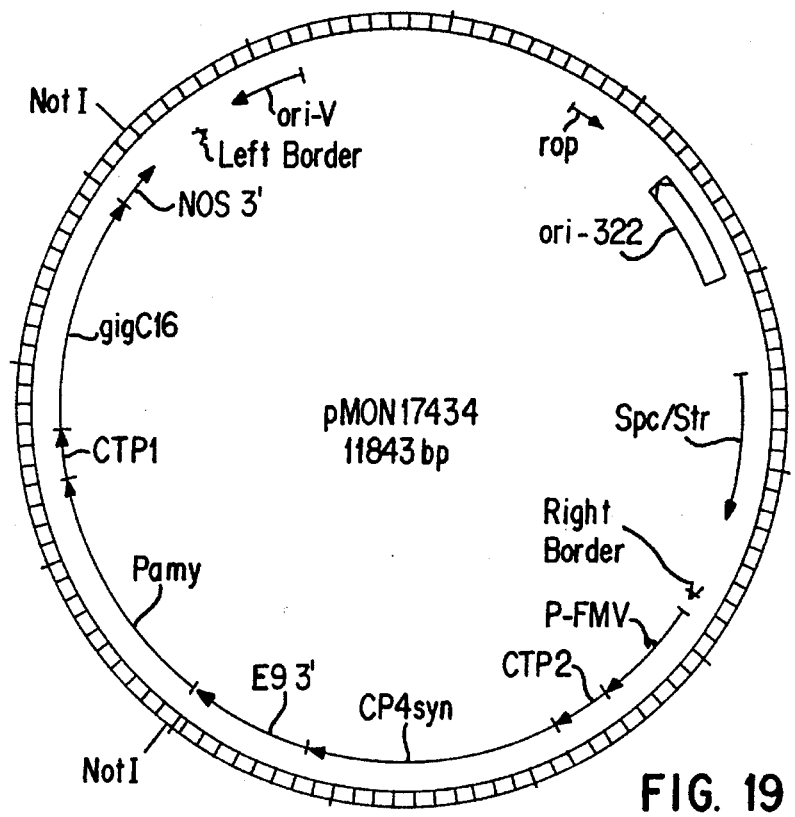
FIG. 19 shows a plasmid map for plant transformation vector pMON 17434.

The promoter for the β-amylase gene from sweet potato was isolated from plasmid pBA5 (Nakamura, Nagoya Univ.) by PCR based on the sequence supplied by Nakamura. A HindIII cloning site was engineered at the 5' end of the promoter, and a BglII site was engineered at the 3' end. Approximately 100 pmoles of primers were used in an amplification using Taq DNA polymerase (Perkin Elmer Cetus) and the manufacturers recommended conditions. The following temperature profile was used for the amplification: 5 cycles of 94° C. 3 min, 55° C. 2 min, 72° C. 2 min, followed by 30 cycles of 94° C. 1 min, 55° C. 2 min, 72° C. 1 min. The template for the reaction was 8 ng of pBA5 plasmid DNA. The amplification yielded a band of the correct size which was cloned as a HindIII/ BglII fragment into pMON999 replacing the E35S promoter, and fused with a BglII / SacI fragment containing the CTP1-GlgC16 chimeric gene. The resultant NotI fragment containing the Pamy-CTP1-GlgC16-Nos cassette was cloned into the NotI site of pMON17227 resulting in the plasmid pMON17434. See FIG. 19.

Transformation and selection of potato plants using plasmids carrying the glyphosate selection marker (i.e., those derived from pMON17227) were carried out by the following process: To transform potatoes using glyphosate as a selectable agent, the appropriate Agrobacterium was grown overnight in 2 ml of LBSCK. The following day, the bacteria was diluted 1:10 with MSO or until an optical density reading of 0.2–0.33 was established. Leaves from the stems of potato plants that had been grown under sterile conditions for three weeks on PM media supplemented with 25 mg/ml ascorbic acid were removed, stems were cut into 3–5 mm segments and inoculated with diluted bacteria as described previously. Explants were placed onto prepared co-culture plates. The co-culture plates contained 1/10 MSO with 1.5 mL of TxD cells overlain with wetted filter paper. About 50 explants were placed per plate. After 2 days co-culture period, explants were placed onto callus induction media which contains 5.0 mg/l Zeatin Riboside, 10 mg/l AgNO3 and 0.1 mg/l NAA for 2 days. Explants were subsequently transferred onto callus induction media which contained 0.025 mM glyphosate for selection. After 4 weeks, explants were placed onto shoot induction media which contained 5.0 mg/l Zeatin Riboside+10 mg/l AgNO3 and 0.3 mg/l GA3, with 0.025 mM glyphosate for selection. Shoots began to appear at 8 weeks. Explants were transferred to fresh shoot induction media every 4 weeks for 12 weeks. Shoots were excised and placed on PM media for about 2 weeks or until they were large enough to be placed into soil.

Each of the vectors described above was inserted into potato plant cells and the regenerated plant lines were tested for expression of the ADPGPP enzyme and solids content. Results from the lines containing the patatin 3.5 promoter, the GBSS promoter or the small subunit ADPGPP promoter indicated that these transformations produced lines which expressed the enzyme in the tuber and resulted in higher solids than control lines. See Table 4 for results of field tests of the patatin 1.0, 3.5, and small potato ADPGPP promoters. Results from the other transformations are inconclusive at this time.

TABLE 4

| Tuber Type/ (Promoter) | Total # Lines | High Solids |
| --- | --- | --- |
| Control | 10 | 0 |
| Patatin 1.0 | 199 | 26 |
| Patatin 3.5 | 59 | 21 |
| P-ADPGPP | 38 | 6 |

Example 6

Figure 15:
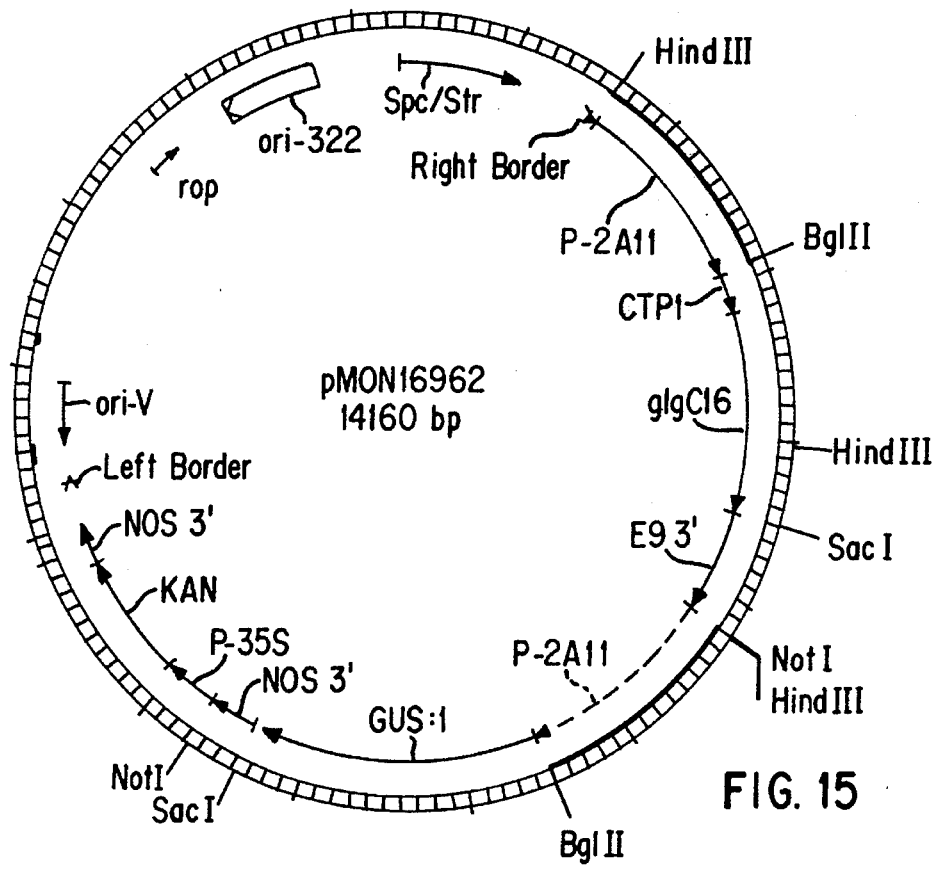
FIG. 15 shows a plasmid map for plant transformation vector pMON 16962.

The 2A11 promoter of tomato, described above was isolated from a *Lycopersicon esculentum* cv. UC82B genomic library by PCR using oligonucleotides based on the sequence published by Pear et al., 1989. Oligonucleotides were designed to add a Hind III restriction site at the 5' end of the promoter, and a Bgl II site at the 3' end for ease of cloning. The 2A11 promoter fragment was fused with the CTP1-glgC16 chimeric gene by ligating the Hind III-Bgl II 2A11 promoter fragment with the Bgl II-Sac I fragment containing CTP1-glgC16 from pMON20102, into the binary vector pMON10098 digested with Hind III and Sac I, resulting in the plasmid pMON16959. A 2A11 promoter-GUS fusion was made by ligating the 2A11 promoter fragment with the Bgl II-Sac I fragment containing the GUS gene from pMON10018, into Hind III-Sac I digested pMON999, resulting in the plasmid pMON16960. pMON16962 was made by adding the 2A11-GUS cassette from pMON16960 as a Not I fragment into pMON16959. See FIG. 15. This plasmid was used to transform tomato variety UC204C. (See transformation method below.) The fruits of regenerated plants were tested for total and soluble solids (Brix) and paste viscosity. The viscosity test showed that the 2A11-glgC16 plants produced fruit which when processed had a paste viscosity of 3.27 as compared to 5.12 for the control. (The scale was the Bostwick test reported in cm.) The solids of fruits from nine lines of transformed plants and three control lines are shown in Table 5. Data is shown from a representative subsampling of over 50 lines. The last control value (*) represents the highest value obtained for the controls in this experiment, with the other control values more representative from this population.

TABLE 5

| Line | % Total Solids | % Brix |
| --- | --- | --- |
| 2A11 | 8.68 | 6 |
| 2A11 | 8.22 | 6.3 |
| 2A11 | 7.99 | 6.3 |
| 2A11 | 7.22 | 6 |
| 2A11 | 7.28 | 5.8 |
| 2A11 | 8.02 | 5.9 |
| 2A11 | 7.52 | 6 |
| 2A11 | 6.86 | 5.05 |
| 2A11 | 6.83 | 5.3 |
| control | 6.74 | 4.8 |
| control | 6.14 | 5 |
| control* | 7.2 | 5.6 |

Two of the green fruit promoters, described above and designated TFM7 and TFM9, were isolated and character- ized from a *Lycopersicon esculentum* cv. VF36 genomic library. For each of these a partial sequence of the 5' terminus, untranslated and promoter regions from which the promoter was derived is herein provided. SEQ ID NO:27 is for TFM7. The 2.3 kb promoter fragment has as a 5' end the internal XbaI site and extends to the putative translation initiation point (modified by placing a BglII recognition site at this latter point). Following fusion to the chimeric CTP-GlgC16 gene (and suitable 3' sequences), the expression cassette was moved into a plant transformation vector, as discussed below. SEQ ID NO:28 is for TFM9. The ~900 bp TFM9 promoter fragment extends from the internal SalI site to the putative translation initiation point (modified by placing a BglII recognition site at this latter point). Following fusion to the chimeric CTP-GlgC16 gene (and suitable 3' sequences), the expression cassette was moved into a plant transformation vector, as discussed below.

Figure 17:
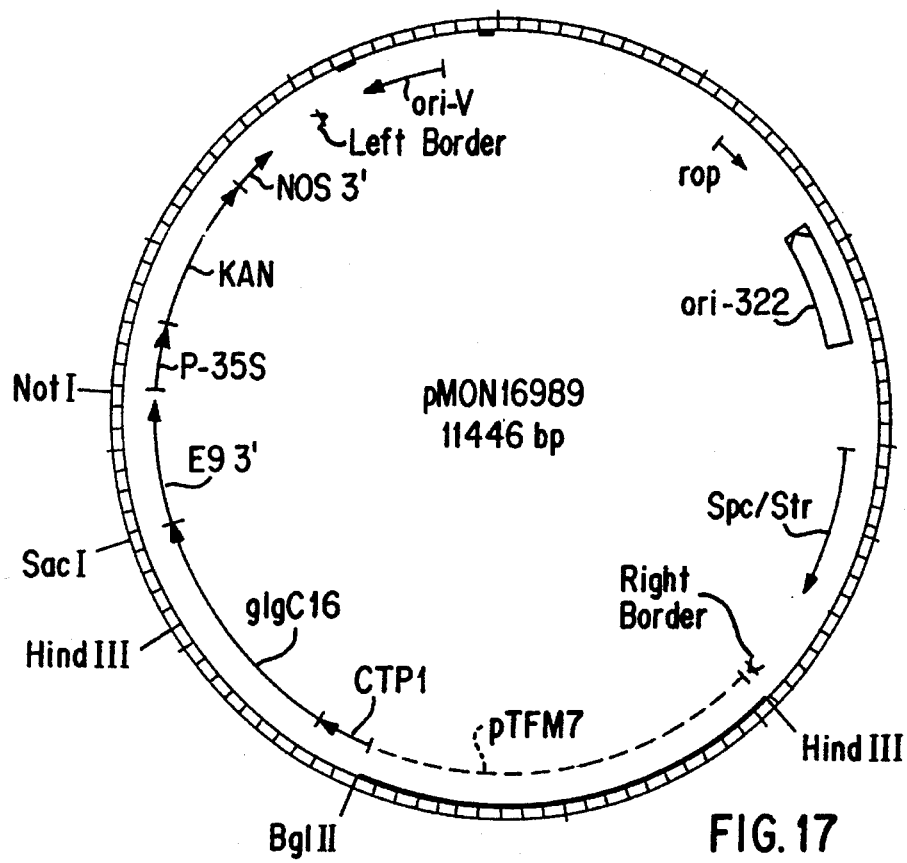
FIG. 17 shows a plasmid map for plant transformation vector pMON 16989.

The TFM7 promoter was ligated into the vector pMON999 for ease of manipulation, resulting in the plasmid pMON16987. Fusion with the CTP-glgC16 chimeric gene was achieved through a triple ligation of the. Hind III-Bgl II TFM7 promoter fragment from pMON16987, with a Bgl II-Sac I fragment from pMON20102 (contains the chimeric gene), and placing this into the binary plant transformation vector pMON10098 digested with Hind III and Sac I. This plasmid, pMON16989, was subsequently used to transform tomato variety UC204C. See FIG. 17.

Figure 16:
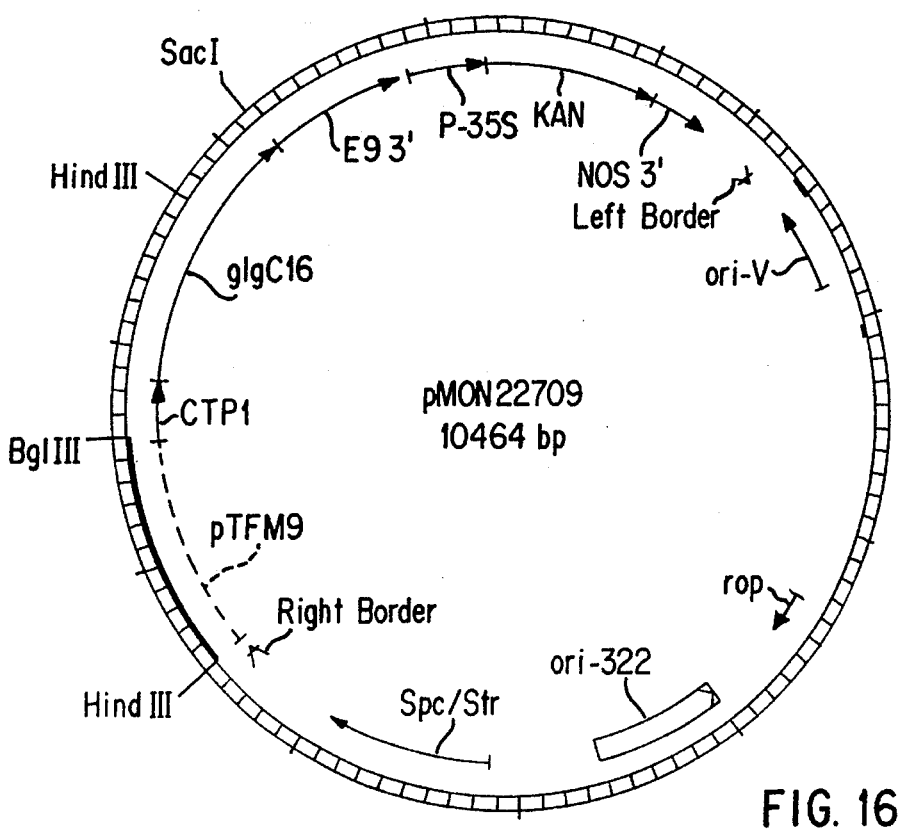
FIG. 16 shows a plasmid map for plant transformation vector pMON 22709.

The TFM9 promoter was fused to CTP1-glgC16 essentially as described above. The SalI-BamHI TFM9 promoter fragment plus GUS from pMON18316 was ligated into pEMBL18+ cut with the same enzymes to give pMON22701. The TFM9 promoter could then be removed as a Hind III-Bgl II fragment (from pMON22701) and ligated with the CTP1-glgC16 Bgl II-Sac I fragment from pMON20102 into Hind III-Sac I digested pMON10098, resulting in pMON22709. See FIG. 16. This plasmid was used to transform tomato variety UC204C.

Tomato plant cells were transformed utilizing the Agrobacterium strains described above generally by the method as described in McCormick et al. (1986). In particular, cotyledons are obtained from 7–8 day old seedlings. The seeds are surface sterilized by the following procedure: 1) soak seeds in water for 15 minutes; 2) soak in 70% EtOH for 1 minute, then rinse with sterile water; 3) soak in 1N NaOH for 20 minutes; 4) rinse 2 times in sterile water; 5) soak in 25% Chlorox with Tween 20 for 25 minutes; 6) rinse in sterile, deionized water 3 times. The seeds are germinated in phyta trays (Sigma) on Davis germination media, as described above, with the addition of 25 mg/L ascorbic acid. The seeds are incubated for 2–3 days at 28° C. in the dark, and then grown in the growth chamber at 25° C., 40% humidity under cool white lights with an intensity of 80 einsteins $m^{-2}s^{-1}$. The photoperiod is 16 hours of light and 8 hours of dark.

Seven to eight days after initiating germination, the cotyledons are explanted as described above. The cotyledons are pre-cultured on "feeder plates" composed of Calgene media, plus acetosyringone and 1 mM galacturonic acid, containing no antibiotics, using the conditions described above.

Cotyledons are then inoculated with a log phase solution of Agrobacterium containing the plasmids described above. The concentration of the Agrobacterium is approximately $5 \times 10^8$ cells/ml. The cotyledons are allowed to soak in the bacterial solution for eight minutes and are then blotted to remove excess solution on sterile Whatman filter disks and are subsequently replaced to the original feeder plate where they are allowed to co-culture for 2–3 days.

Selection for transformed plants is made by kanamycin or glyphosate, depending on the construction of the plasmid used to transform the cells. The kanamycin (NPTII) method is given above. The glyphosate method follows.

Cotyledons are transferred to selection plates containing Davis regeneration media with 2 mg/l zeatin riboside, 500 μg/ml carbenicillin, and 100 μg/ml cefotaxime. After 8 days, tissue is moved to fresh regeneration medium containing 0.03 mM glyphosate, 500 μg/ml carbenicillin, and 100 μg/ml cefotaxime. After 2–3 weeks, cotyledons with callus and/or shoot formation are transferred to fresh Davis regeneration plates containing glyphosate (0.05 mM), carbenicillin and cefotaxime. The experiment is scored for transformants at this time. The callus tissue is subcultured at regular 3 week intervals and any abnormal structures are trimmed so that the developing shoot buds will continue to regenerate. Shoots develop within 3–4 months.

Once shoots develop, they are excised cleanly/rom callus tissue and are planted on rooting selection plates containing the same level of glyphosate, carbenicillin, and cefotaxime, but with a reduced level of zeatin (1 mg/L). Benlate is also incorporated into the medium. These shoots form roots on the selection media within three weeks. Whole plants are then obtained as described above.

Fruit from plants transformed with pMON16989 (TFM7 promoter) have been obtained and tested. TFM7 causes high expression of GlgC16 in the green fruit (>0.1% extracted protein), but GlgC16 is very weak or undetectable in the ripe fruit. TFM7 results in starch in the ripe fruit in some lines, while controls always have an iodine score of '0', indicating no starch. Juice from these fruits is very viscous, and soluble solids are increased in many of the lines. Comparison data is shown in Table 6. Soluble solids and starch rating were measured in serum from hot break tomato juice. Starch was measured by adding one drop of an iodine solution to filtered serum, and measuring color intensity on a 0–4 scale where yellow=0 (no starch) to dark blue=4 (high starch).

TABLE 6

| LINE | % BRIX | IODINE STAIN |
| --- | --- | --- |
| 16989-10712 | 5.7 | 0 |
| 16989-10714 | 6 | 2 |
| 16989-10223 | 5.6 | 4 |
| 16989-10381 | 6.7 | 4 |
| UC204C | 5.8 | 0 |
| UC204C | 6.3 | 0 |
| UC204C | 5.4 | 0 |
| UC204C | 5.4 | 0 |
| UC204C | 5.4 | 0 |
| UC204C | 6.7 | 0 |
| UC204C | 5.2 | 0 |
| UC204C | 6 | 0 |
| UC204C | 6 | 0 |

Example 7

Figure 20:
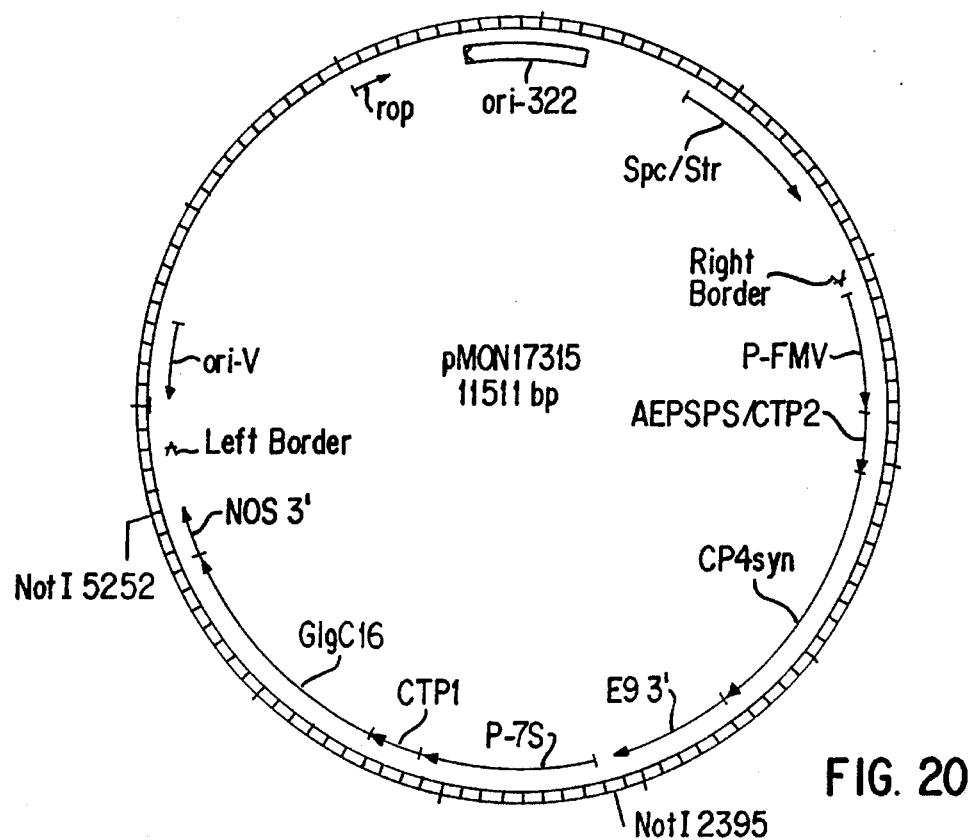
FIG. 20 shows a plasmid map for plant transformation vector pMON 17315.

Decreasing the lipid content in the seeds of certain plants is desirable due to health concerns or for improved processing qualities. For example, a low calorie peanut butter, having a higher starch content and lower oil content would be beneficial. Also, soybeans having lower oil content would be better for producing certain products, such as tofu, soy sauce, soy meat extenders, and soy milk. Such fat reduction and starch increase is accomplished by expression of an ADPglucose pyrophosphorylase, such as glgC16, in the seed, preferably by use of a seed specific promoter as discussed above. This has been accomplished in canola by the following method:

The CTP-glgC16 gene fusion was placed behind the soybean β-conglycinin 7S storage promoter described above. This cassette was cloned into pMON 17227 to form the vector pMON 17315 (FIG. 20). This vector was used to transform canola by Agrobacterium transformation followed by glyphosate selection. Regenerated plants were analyzed and the presence of the enzyme in most transformants was confirmed by Western blot analysis. Seeds from four transformed lines have been obtained and analyzed for oil, starch, and protein content and moisture. The starch content was found to have increased to 8.2–18.2 percent (based on fresh weight) as compared to 0.9–1.6 percent in control lines (transformed with pMON 17227 only). The oil content was found to have been decreased from 26.7–31.6 percent in the controls to 13.0–15.5 percent in the transformed lines. Protein content and moisture were not significantly changed. In some lines seed weight was increased which may indicate that total yield may also be increased.

Example 8

Figure 21:
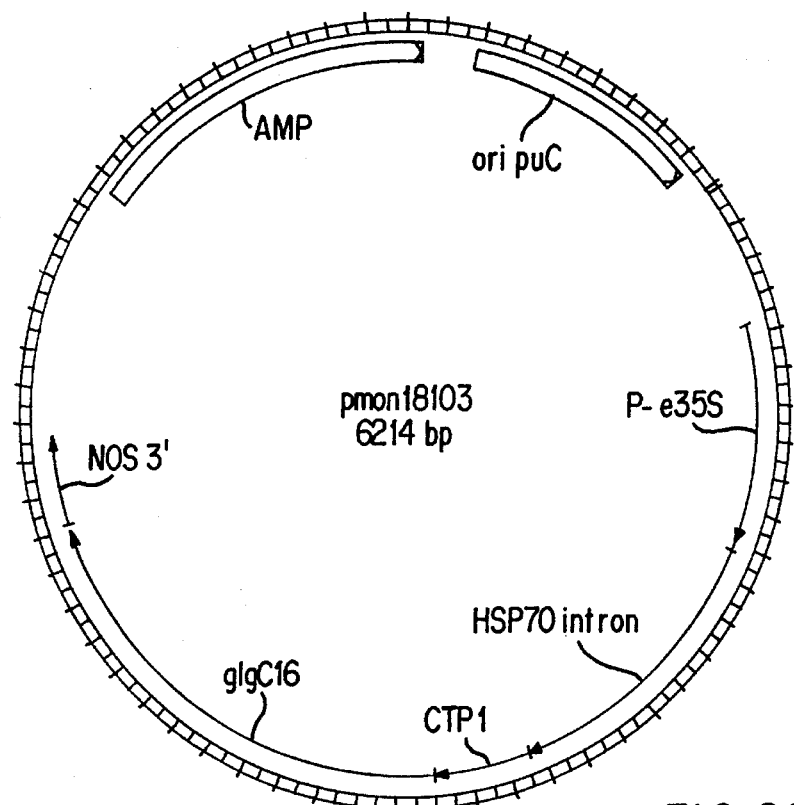
FIG. 21 shows a plasmid map for plant transformation vector pMON 18103.
Figure 22:
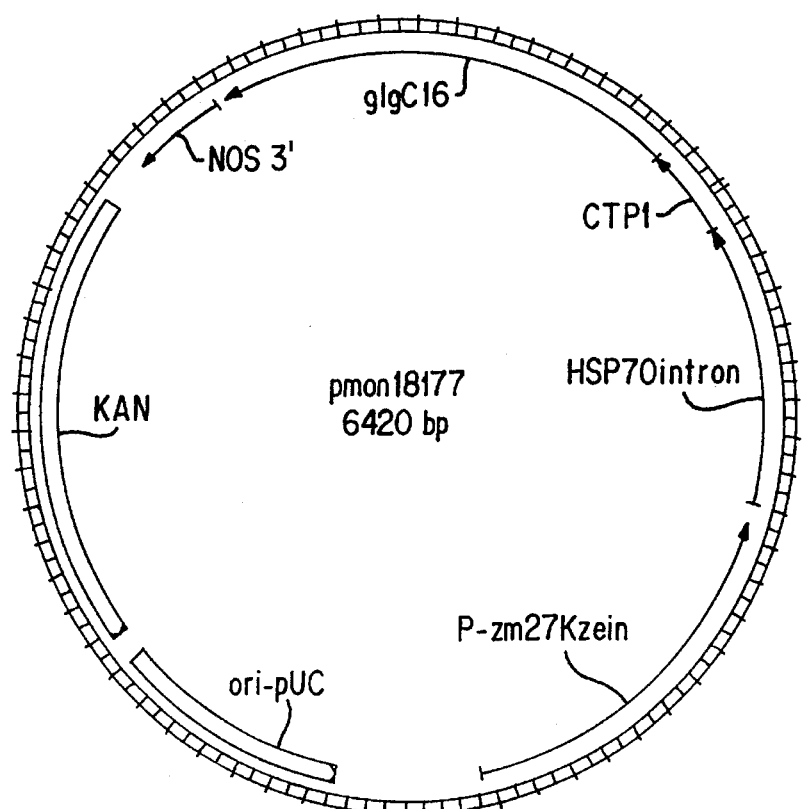
FIG. 22 shows a plasmid map for plant transformation vector pMON 18177.

The CTP-GlgC 16 fusion has also been expressed in maize. When expressed in maize Black Mexican Sweet callus, following introduction by particle gun (Klein et al., 1989; Fromm et al., 1990) of plasmid DNA (pMON18103, FIG. 21) in which the CTP-GlgC16 is expressed from the 35S promoter (Russell et al.), the CTP-GlgC16 fusion led to increased starch content in the callus and the correct processing of the fusion was demonstrated. The starch levels were 2–3 times higher in the transformed lines as in control lines. The CTP-GlgC16 fusion has also been introduced in stable, regenerable corn transformation under the control of endosperm promoters, including those for the waxy/GBSS, for zein, and for Shrunken 2/ADPGPP. pMON18177, FIG. 22, illustrates a vector for such a transformation.

BIBLIOGRAPHY

Ammirato, P. V., et al. *Handbook of Plant Cell Culture—Crop Species.* Macmillan Publ. Co. (1984).

Anderson, Joseph M., James Hnilo, Raymond Larson, Thomas W. Okita, Matthew Morell, and Jack Preiss. (1989a) *J. Biol. Chem.* 264 (21):12238–12242.

Anderson, Joseph M., Thomas W. Okita, Woo Taek Kim, James Hnilo, Joseph Sowokinos, Matthew Morell, and Jack Preiss. (1989b) First International Symposium on the Molecular Biology of the Potato, Bar Harbor, Me.

Arnon, D. I. (1949) *Plant Physiol.* 24,1–15

Baecker, Preston A., Clement E. Furlong, and Jack Preiss. (1983) *J. Biol. Chem.* 258 (8):5084–5087.

Bartlett, S. G., A. R. Grossman, & N. H. Chua. (1982) In *Methods in Chloroplast Molecular Biology.* Elsevier Biomedical Press, New York, pp 1081–1091.

Beck, Erwin, and Paul Ziegler. (1989) *Biosynthesis and Degradation of Starch in Higher Plants.* In *Annual Review of Plant Physiology and Plant Molecular Biology.* 95–117.

Benfey, P., Ren, L., and Chua, N. H. (1989) The EMBO Journal, Vol.5, no.8, pp 2195–2202.

Bevan, M. (1984) *Nucleic Acids Res.* 12 (22): 8711–8721.

Bevan, M., R. Barker, A. Goldsbrough, M. Jarvis, T. Kavanagh, and G. Iturriaga. (1986) *Nucleic Acids Res.* 14 (11):4625–4638.

Bhave, M. R., S. Lawrence, C. Barton, and L. C. Hannah. (1990) Plant Cell 2: 581–588.

Birnboim, H. C., and J. Doly. (1979) *Nucleic Acids Res.* 7:1513–1523.

Blennow, A. and Johansson, G. (1991) *Phytochemistry* 30:437–444.

Bray, Elizabeth A., Satoshi Naito, Nai-Sui Pan, Edwin Anderson, Philip Dube, and Roger N. Beachy. (1987) *Planta* 172 364–370.

Callas, J., Fromm, M. and Walbot, V. (1987) Genes and Development 1:1183–1200.

Carlson, Curtis A., Thomas F. Parsons, and Jack Preiss. (1976) *J. Biol. Chem.* 251 (24):7886–7892.

Catley, M. A., C. W. Bowman, M. W. Bayless and M. D. Gale. (1987) *Planta* 171:416–421.

Cattaneo, J., M. Damotte, N. Sigal, F. Sanchez-Medina, and J. Puig. (1969) *Biochem. Biophys. Res. Commun.* 34 (5):694–701.

Chang, A. C. Y. and S. N. Cohen. (1978) J. Bacteriol. 134; 1141–1156.

Copeland, L. and J. Preiss (1981) Plant Physiol. 68: 996–1001.

Creuzet-Sigal, N., M. Latil-Damotte, J. Cattaneo, and J. Puig. (1972) *Genetic Analysis and Biochemical Characterization of Mutants Impairing Glycogen Metabolism in Escherichia coli K12*. In *Biochemistry of the Glycosidic Linkage: An Integrated View*. Edited by R. Piras and H. G. Pontis. 647–680. New York: Academic Press Inc.

Datta, S. W., Pererhans, A., Datta, K., Potrykus, I. (1990) *Biotechnology* 8:736–740.

Deikman, J. and R. L. Fischer. (1988) *The EMBO Journal* 7, 11, 3315–3320.

Dickinson, D. B. and J. Preiss (1969) Plant Physiol. 44:1058–1062.

Ditta, G., Stanfield, S., Corbin, D., and Helinski, D. R. (1980). Broad host range DNA cloning system for Gram-Negative bacteria: construction of a gene bank of *Rhizobium meliloti*. Proc Natl Acad Sci USA 77, 7347–7351.

Ebbelaar, M., Chene, S., van Marle, N., Gouveia, M., and Recourt, K. (1993) Int. Symp. on Gen. Manip. of Plant Metabolism and Growth, 29–31 March, Norwich UK Abstract #9.

Ehrlich, H. A. (1989) Ed. *PCR Technology—Principles and Applications for DNA Amplification*. Stockton Press, New York.

Fling, M. E., Kopf, J., and Richards, C. (1985). Nucleotide sequence of the transposon Tn7 gene encoding an aminoglycoside-modifying enzyme, 3"(9)-O-nucleotidyltrans-ferase. Nucleic Acids Research 13 no.19, 7095–7106.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L., and Woo, S. C. (1983). Expression of bacterial genes in plant cells. Proc Natl Acad Sci USA 80, 4803–4807.

Fraley, R. T., Rogers, S. G., Horsch, R. B., Eichholtz, D. A., Flick, J. S., Fink, C. L., Hoffmann, N. L., and Sanders, P. R. (1985). The SEV system: a new disarmed Ti plasmid vector system for plant transformation. Bio/Technology 3, 629–635.

Fraley, R., Rogers, S., and Horsch, R. (1986). Genetic transformation in higher plants. Critical Reviews in Plant Sciences 4, No.1, 1–46.

Frohman, M. A., M. K. Rush, and G. R. Martin. (1988) Proc. Natl. Acad. Sci. USA 85: 8998–9002.

Fromm et al. (1990) *Bio/Technology* 8: 833–839.

Fromm, M., (1990 UCLA Symposium on Molecular Strategies for Crop Improvement, April 16–22, 1990. Keystone, Colo.

Gentner, Norman, and Jack Preiss. (1967) *Bioch. Biophys. Res. Commun.* 27 (3): 417–423.

Gentner, Norman, and Jack Preiss. (1968) *J. Biol. Chem.* 243 (22):5882–5891.

Ghosh, Hara Prasad, and Jack Preiss. (1966) *J. Biol. Chem.* 241 (19):4491–4504.

Govons, Sydney, Norman Gentner, Elaine Greenberg, and Jack Preiss. (1973) *J. Biol. Chem.* 248 (5):1731–1740.

Govons, Sydney, Robert Vinopal, John Ingraham, and Jack Preiss. (1969) *J. Bact.* 97 (2):970–972.

Hannapel, D. J. (1990) Differential expression of potato tuber protein genes. Plant Physiol. 94: 919–925.

Haugen, T. H., A. Ishaque and J. Preiss (1976) *J. Biol, Chem.* 251. (24) 7880–7885.

Hayashimoto, A., Z. Li, Murai, N. (1990) *Plant Physiol.* 93:857–863.

Heldt, H. W., C. J. Chon, D. Maronde, A. Herold, Z. S. Stankovic, D. Walker, A. Kraminer, M. R. Kirk, and U. Heber. (1977) *Plant Physiol.* 59: 1146–1155.

Herrera-Estrella, L., et al. (1983) *Nature* 303:209

Horsch, R. B. and H. Klee. (1986) *Proc. Natl. Acad, Sci. U.S.A.* 83:4428–32.

Iglesias, et al., (1993) 268:1081–1086.

Jarret, R. L., Hasegawa, P. M., and Erickson, H. T. (1980a) Physiol. Plant. 49: 177–184.

Jarret, R. L., Hasegawa, P. M., and Erickson, H. T. (1980b) J. Amer. Soc. Hort. Sci. 105: 238–242.

Jarret, R. L., Hasegawa, P. M., and Bressan, R. A. (1981) In Vitro 17: 825–830.

Kahefuda, et al. (1992) Plant Physiol. 99:359–361.

Kaiser, W. M. and J. A. Bassham (1979) Plant Physiol. 63: 109–113.

Kappel, William K., and Jack Preiss. (1981) *Arch. Biochem. Biophys.* 209 (1):15–28.

Katagiri, F., E. Lam and N. Chua. (1989) *Nature* 340:727–730.

Kay, R., A. Chan, M. Daly and J. McPherson. (1987) *Science* 236:1299–1302.

Kim, Woo Taek, Vincent R. Franceschi, Thomas W. Okita, Nina L. Robinson, Matthew Morell, and Jack Preiss. (1989) Plant Physiol. 91:217–220.

Klee, H. J., et al. (1985) *Bio/Technology* 3:637–42.

Klee, H. J., and Rogers, S. G. (1989). Plant gene vectors and genetic transformation: plant transformation systems based on the use of *Agrobacterium tumefaciens*. Cell Culture and Somatic Cell, Genetics of Plants 6, 1–23.

Klein et al. (1989) *Bio/Technology* 6: 559–563.

Kleinkopf, G. E., Westermann, D. T., Wille, M. J., and Kleinschmidt, G. D. (1987) Specific gravity of Russet burbank potatoes. Am. Potato J. 64: 579–587.

Klösgen, R. B., H. Sandler and J. H. Weil. (1989) *Mol. Gen Genet* 217:155–166.

Kossmann et al. (1991) *Mol. Gen. Genet,* 230:39–44.

Krishnan, H. B., C. D. Reeves, and T. W. Okita (1986) Plant Physiol. 81: 642–645.

Kumar, A., P. Ghosh, M. Young, M. Hill and J. Preiss. (1989) *J. Biol. Chem.* 264, 18, 10464–10471.

Latil-Damotte, M., and C. Lares. (1977) *Mol. Gen. Genet.* 150:325–329.

Lee, Young Moo, Anil Kumar, and Jack Preiss. (1987) *Nucleic Acids Res.* 15 (24):10603.

Leung, Patrick, Young-Moo Lee, Elaine Greenberg, Keith Esch, Sharon Boylan, and Jack Preiss. (1986) *J. Bact.* 167 (1):82–88.

Leung, Patrick S. C., and Jack Preiss. (1987a) Biosynthesis of Bacterial Glycogen: Primary Structure of *Salmonella typhimurium* ADPglucose Synthetase as Deduced from the Nucleotide Sequence of the glgC Gene. *J. Bact.* 169 (9): 4355–4360.

Leung, Patrick S. C., and Jack Preiss. (1987b). Cloning of the ADPglucose Pyrophosphorylase (glgC) and Glycogen Synthase (glgA) Structural Genes from *Salmonella typhimurium* LT2. *J. Bact.* 169 (9): 4349–4354.

Levi, Carolyn, and Jack Preiss. (1978) *Plant Physiol.* 61:218–220.

Lin, Tsan-Piao, Timothy Caspar, Chris Somerville, and Jack Preiss. (1988a) *Plant Physiol.* 86:1131–1135.

Lin, Tsan-Piao, Timothy Caspar, Chris R. Somerville, and Jack Preiss. (1988b) *Plant Physiol.* 88:1175–1181.

Loh, E. Y., J. F. Elliott, S. Cwirla, L. L. Lanier, and M. M. Davis. (1989) Science 243:217–220.

Lowry, O. H., N. J. Rosebrough, A. L. Farr, and R. J. Randall. (1951) *J. Biol. Chem.* 193:265.

Lutcke et al. (1987), *EMBO J.* 6(1):43–48.

Macherel, D., H. Kobayashi and T. Akazawa. (1985) *Biochem., Biophys. Res. Commun.* 133:140–146.

Mares, D. J., J. S. Hawker, and J. V. Possingham. (1978) *J. of Experimental Botany* 29 (111):829–835.

McCormick, S., J. Niedermeyer, J. Fry, A. Barnason, R. Hosrch, and R. Fraley (1986) *Plant Cell Reports* 5:80–84.

Meyer et al. (1993) Arch. Biochemistry & Biophys. 302:64–71.

Mignery, Gregory A., Craig S. Pikaard, and William D. Park. (1988) Gene 62:27–44.

Miller, J. H. (1972) Experiments in Molecular Genetics. Cold Spring Harbor Laboratory, Cold Spring Harbor, N.Y.

Morell, M. K., M. Bloom, and J. Preiss. (1988) J. Biol. Chem. 263:633–637.

Morell, Matthew K., Mark Bloom, Vicki Knowles, and Jack Preiss. (1987) *Plant Physiol.* 85:182–187.

Mori et al. (1991) *J. Biol. Chem.* 266: 18446–18453.

Muller, B. T., J. Koschmann, L. C. Hannah, L. Willmitzer, and U. Sonnewald (1990) Mol. Gen. Genet. 224:136–146.

Nakamura, Yasunori, Kazuhiro Yuki, Shin-Young Park, and Toshihide Ohya. (1989) *Plant Cell Physiol* 30 (6): 833–839.

Nakano et al. (1989) *J. Biochem.* 106: 691–695.

Nakata, P. A., Anderson. J. M., Okita, T. W., and Preiss, J (1992) *J. Cell. Biochem.* Suppl. 16F, Abstract Y311, p. 266.

Odell, J. T., Nagy, F., and Chua, N. H. (1985). Identification of DNA sequences required for activity of the cauliflower mosaic virus 35S promoter. Nature 313, 810–812.

Ohta etal. (1991) *Mol. Gen. Genet,* 225: 369–378.

Okita, Thomas W., Elaine Greenberg, David N. Kuhn, and Jack Preiss. (1979) *Plant Physiol.* 64:187–192.

Okita, Thomas W., Raymond L. Rodriguez, and Jack Preiss. (1981) *J. Biol. Chem.* 256 (13):6944–6952.

Okita, T. W., P. A. Nakata, J. M. Anderson, J. Sowokinos, M. Morell, and J. Preiss. (1990) 93: 785–790.

Olive, Mark R., R. John Ellis, and Wolfgang Schuch W. (1989) *Plant Mol. Biol,* 12: 525–538.

Pear, Julie R., Neal Ridge, Rik Rasmussen, Ronald E. Rose, and Catherine M. Houch. (1989) *Plant Mol. Biol.* 13:639–651.

Pedersen, Karl, John Devereux, Deborah R. Wilson, Edward Sheldon, and Brian A. Larkins. (1982) Cell 29: 1015–1026.

Pikaard, Craig S., John S. Brusca, David J. Hannapel, and William D. Park. (1987) *Nucleic Acids Res.* 15 (5):1979–1994.

Plaxton, William C., and Jack Preiss. (1987) *Plant Physiol.* 83: 105–112.

Preiss, Jack. (1973) *Adenosine Diphosphoryl Glucose Pyrophosphorylase.* In *Group Transfer.* Edited by P. D. Boyer. 73–119. New York: Academic Press.

Preiss, J. (1984) Bacterial glycogen synthesis and its regulation. Annu. Rev. Microbiol. 38:419–458.

Preiss, Jack. (1988) *Biosynthesis of Starch and Its Regulation.* In *The Biochemistry of Plants.* Edited by J. Preiss. 184–249. Orlando, Fla.: Academic Press.

Preiss, Jack, Laura Shen, Elaine Greenberg, and Norman Gentner. (1966) *Biochem.* 5 (6):1833–1845.

Preiss, J., A. Sabraw, and E, Greeberg. (1971) Biochem. Biophys. Res. Commun. 42: 180–186.

Recondo, Eduardo, and Luis F. Leloir. (1961) *Bioch. Biophys. Res. Commun.* 6 (2):85–88.

Rocha-Sosa, Maria, Uwe Sonnewald, Wolf Frommer, Marina Stratmann, Jeff Schell, and Lothar Willmitzer. (1989) *EMBO J.* 8 (1):23–29.

Rogers, S. G., H. J. Klee, R. B. Horsch, and R. T. Fraley. (1987) *Improved Vectors for Plant Transformation; Expression Cassette Vectors and new Selectable Markers.* In *Methods in Enzymology.* Edited by R. Wu and L. Grossman. 253–277. San Diego: Academic Press.

Rogers, S., et al. (1987) In 153 *Methods in Enzymology.* Edited by H. Weissbach and A. Weissbach. 253: Academic Press.

Rogers, S., and Klee, H. (1987). Pathways to genetic manipulation employing Agrobacterium. Plant Gene Research, Plant DNA Infectious Agents, Vol IV. Hohn, T. and J. Schell, eds. Springer-Verlag, Vienna, 179–203.

Rohde et al. (1990) J. Genet. & Breed. 44:311–315.

Romeo, T. and Preiss, J. (1989) Advances in Microbial Physiology, Vol. 30, p. 210.

Rosahl, Sabine, Renate Schmidt, Jeff Schell, and Lothar Willmitzer. (1986) *Mol. Gen. Genet.* 203:214–220.

Russell et al., Abstracts from 1992 American Society of Plant Physiologists Annual Meeting and from the 1993 Maize Genetics Conference.

Samac, D. A., C. M. Hironaka, P. E. Yallaly and D. M. Shah (1990) Plant Physiol. 93:907–914.

Santarius, K. A. and U. Heber (1965) Biochim. Biophys. Acta 102:39–54.

Schmidhauser, T. J. and D. R. Helinski. (1985) *J. Bacteriol.*]64–155.

Scott, N. S., M. J. Tymms and J. V. Possingham (1984) *Planta* 161:12–19.

Senser, M., F. Schotz and E. Beck. (1975) *Planta* 126:1–10.

Shahar et al. (1992) Plant Cell 4:135–147.

Sheerman, S., and M. W. Bevan. (1988) *Plant Cell Reports* 7:13–16.

Shimamoto, K. et al. (1989) *Nature* 338:274–276.

Smith-White, B. and J. Preiss (1992) J. Mol. Evol. 34:449–464.

Solanoubat, M. and G. Belliard (1987) Gene 60:47–56.

Solanoubat, M. and G. Belliard (1989) Gene 84:181–185.

Sonnewald, Uwe, Daniel Studer, Mario Rocha-Sosa, and Lothar Willmitzer. (1989) *Planta* 178:76–83.

Sowokinos, Joseph R., and Jack Preiss. (1982) *Plant Physiol.* 69:1459–1466.

Stalker, D. M., Thomas, C. M., and Helinski, D. R. (1981). Nucleotide sequence of the region of the origin of replication of the broad host range plasmid RK2. Mol Gen Genet 181, 8–12.

Stiekema et al. (1988) *Plant Mol. Biol.* 11: 255–269.

Stukerlj et al. (1990) *Nucl. Acids Res.* 18:46050.

Takaha et al., (1993) *J. Biol. Chem.* 26 8:1391–1396.

Tierney, Mary L., Elizabeth Bray A., Randy D. Allen, Yu Ma, Roger F. Drong, Jerry Slightom, and Roger N. Beachy. (1987) *Planta* 172:356–363.

Timko, M. P., L. herdies. E. DeAlmeida, A. R. Cashmore, J. Leemans and E. Krebbers. (1988) *Genetic Engineering of Nuclear Encoded Components of the Photosynthetic Apparatus in Arabidopsis.* In *Impact of Chemistry on Biotechnology—A Multidisciplinary Discussion.* Edited by M. Phillips, S. Shoemaker, R. M. Ottenbrite, R. D. Middlekauff. 279–295. Washington DC: ACS Books.

Timko, M. P., Kausch, A. P., Castresana, C., Fassler, J., Herrera-Estrella, L., Van den Broeck, G., Van Montagu, M., Schell, J., and Cashmore, A. R. (1985) Light regulation of plant gene expression by an upstream enhancer-like element. Nature (London) 318: 579–582.

Tsai, C. Y. and O. E. Nelson. (1966) Science 151: 341–343.

Vasil, V., F. Redway and I. Vasil. (1990) *Bio/Technology* 8:429–434.

Van der Leij, et al. (1991) *Mol. Gen. Genet.* 228, 240–248.

Von Scheele, C. (1937) Die Bestimmung des Starkghelts und der Trockensubstanz der Kartoffel mit hilfe des Specifischen gewichte. Landw Ver Stn 127: 67–96.

Wong, E. Y., Seetharam, R., Kotts, C. E., Heeren, R. A., Klein, B. K., Braford, S. R., Mathis, K. J., Bishop, B. F., Siegel, N. R., Smith, C. E. and Tacon, W. C. (1988) Gene 68: 193–203.

Yoshida et al. (1992) *Gene* 10: 255–259.

---

We claim:

1. A method of producing genetically transformed tomato plants which have elevated starch content, comprising the steps of:
   (a) inserting into the genome of a tomato plant cell a recombinant, double-stranded DNA molecule comprising
      (i) a promoter selected from the group consisting of green fruit promoters,
      (ii) a structural DNA sequence that causes the production of an RNA sequence which encodes a fusion polypeptide comprising an amino-terminal plastid transit peptide and a foreign ADPglucose pyrophosphorylase enzyme,
      (iii) a 3' non-translated DNA sequence which functions in plant cells to cause transcriptional termination and the addition of polyadenylated nucleotides to the 3' end of the RNA sequence;
   (b) obtaining transformed tomato plant cells; and
   (c) regenerating from the transformed tomato plant cells genetically transformed tomato plants which have an elevated starch content.

2. The method of claim 1 wherein the DNA sequence encoding ADPglucose pyrophosphorylase enzyme is from *E. coli*.

3. The method of claim 1 wherein said enzyme is deregulated.

4. The method of claim 2 wherein said enzyme is glgC16.

5. A recombinant, double-stranded DNA molecule comprising in sequence:
   (a) a promoter selected from the group consisting of green fruit promoters;
   (b) a structural DNA sequence that causes the production of an RNA sequence which encodes a fusion polypeptide comprising an amino-terminal plastid transit peptide and a foreign ADPglucose pyrophosphorylase enzyme; and
   (c) a 3' non-translated region which functions in plant cells to cause transcriptional termination and the addition of polyadenylated nucleotides to the 3' end of the RNA sequence, said promoter is heterologous with respect to said structural DNA.

6. The DNA molecule of claim 5 wherein the DNA sequence encoding ADPglucose pyrophosphorylase enzyme is from *E. coli*.

7. The DNA molecule of claim 5 wherein said enzyme is deregulated.

8. The DNA molecule of claim 6 wherein said enzyme is glgC16.

9. A tomato plant cell comprising a recombinant, double-stranded DNA molecule comprising in sequence:
   (a) a promoter selected from the group consisting of green fruit promoters;
   (b) a structural DNA sequence that causes the production of an RNA sequence which encodes a fusion polypeptide comprising an amino-terminal plastid transit peptide and a foreign ADPglucose pyrophosphorylase enzyme; and
   (c) a 3' non-translated region which functions in plant cells to cause transcriptional termination and the addition of polyadenylated nucleotides to the 3' end of the RNA sequence in which the DNA molecule is foreign to said plant cell.

10. The tomato plant cell of claim 9 wherein the DNA sequence encoding ADPglucose pyrophosphorylase enzyme is from *E. coli*.

11. The tomato plant cell of claim 9 wherein said enzyme is deregulated.

12. The tomato plant cell of claim 10 wherein said enzyme is glgC16.

13. A tomato plant consisting of plant cells of claim 9.

14. The tomato plant of claim 13 wherein the DNA sequence encoding ADPglucose pyrophosphorylase enzyme is from *E. coli*.

15. The tomato plant of claim 13 wherein said enzyme is deregulated.

16. The tomato plant of claim 14 wherein said enzyme is glgC16.

* * * * *

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 1296 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1293

( x i ) SEQUENCE DESCRIPTION: SEQ ID NO:1:

```
ATG GTT AGT TTA GAG AAG AAC GAT CAC TTA ATG TTG GCG CGC CAG CTG        48
Met Val Ser Leu Glu Lys Asn Asp His Leu Met Leu Ala Arg Gln Leu
 1               5                  10                  15

CCA TTG AAA TCT GTT GCC CTG ATA CTG GCG GGA GGA CGT GGT ACC CGC        96
Pro Leu Lys Ser Val Ala Leu Ile Leu Ala Gly Gly Arg Gly Thr Arg
             20                  25                  30

CTG AAG GAT TTA ACC AAT AAG CGA GCA AAA CCG GCC GTA CAC TTC GGC       144
Leu Lys Asp Leu Thr Asn Lys Arg Ala Lys Pro Ala Val His Phe Gly
         35                  40                  45

GGT AAG TTC CGC ATT ATC GAC TTT GCG CTG TCT AAC TGC ATC AAC TCC       192
Gly Lys Phe Arg Ile Ile Asp Phe Ala Leu Ser Asn Cys Ile Asn Ser
 50                  55                  60

GGG ATC CGT CGT ATG GGC GTG ATC ACC CAG TAC CAG TCC CAC ACT CTG       240
Gly Ile Arg Arg Met Gly Val Ile Thr Gln Tyr Gln Ser His Thr Leu
 65                  70                  75                  80
```

| | | | | | | | | | | | | | | | | |
|---|---|---|---|---|---|---|---|---|---|---|---|---|---|---|---|---|
| GTG | CAG | CAC | ATT | CAG | CGC | GGC | TGG | TCA | TTC | TTC | AAT | GAA | GAA | ATG | AAC | 288 |
| Val | Gln | His | Ile | Gln | Arg | Gly | Trp | Ser | Phe | Phe | Asn | Glu | Glu | Met | Asn | |
| | | | | 85 | | | | 90 | | | | | | 95 | | |
| GAG | TTT | GTC | GAT | CTG | CTG | CCA | GCA | CAG | CAG | AGA | ATG | AAA | GGG | GAA | AAC | 336 |
| Glu | Phe | Val | Asp | Leu | Leu | Pro | Ala | Gln | Gln | Arg | Met | Lys | Gly | Glu | Asn | |
| | | | | 100 | | | | | 105 | | | | 110 | | | |
| TGG | TAT | CGC | GGC | ACC | GCA | GAT | GCG | GTC | ACC | CAA | AAC | CTC | GAC | ATT | ATC | 384 |
| Trp | Tyr | Arg | Gly | Thr | Ala | Asp | Ala | Val | Thr | Gln | Asn | Leu | Asp | Ile | Ile | |
| | | 115 | | | | | 120 | | | | | 125 | | | | |
| CGT | CGT | TAT | AAA | GCG | GAA | TAC | GTG | GTG | ATC | CTG | GCG | GGC | GAC | CAT | ATC | 432 |
| Arg | Arg | Tyr | Lys | Ala | Glu | Tyr | Val | Val | Ile | Leu | Ala | Gly | Asp | His | Ile | |
| | 130 | | | | | 135 | | | | | 140 | | | | | |
| TAC | AAG | CAA | GAC | TAC | TCG | CGT | ATG | CTT | ATC | GAT | CAC | GTC | GAA | AAA | GGT | 480 |
| Tyr | Lys | Gln | Asp | Tyr | Ser | Arg | Met | Leu | Ile | Asp | His | Val | Glu | Lys | Gly | |
| 145 | | | | | 150 | | | | | 155 | | | | | 160 | |
| GTA | CGT | TGT | ACC | GTT | GTT | TGT | ATG | CCA | GTA | CCG | ATT | GAA | GAA | GCC | TCC | 528 |
| Val | Arg | Cys | Thr | Val | Val | Cys | Met | Pro | Val | Pro | Ile | Glu | Glu | Ala | Ser | |
| | | | | 165 | | | | | 170 | | | | | 175 | | |
| GCA | TTT | GGC | GTT | ATG | GCG | GTT | GAT | GAG | AAC | GAT | AAA | ACT | ATC | GAA | TTC | 576 |
| Ala | Phe | Gly | Val | Met | Ala | Val | Asp | Glu | Asn | Asp | Lys | Thr | Ile | Glu | Phe | |
| | | | 180 | | | | | 185 | | | | | 190 | | | |
| GTG | GAA | AAA | CCT | GCT | AAC | CCG | CCG | TCA | ATG | CCG | AAC | GAT | CCG | AGC | AAA | 624 |
| Val | Glu | Lys | Pro | Ala | Asn | Pro | Pro | Ser | Met | Pro | Asn | Asp | Pro | Ser | Lys | |
| | | 195 | | | | | 200 | | | | | 205 | | | | |
| TCT | CTG | GCG | AGT | ATG | GGT | ATC | TAC | GTC | TTT | GAC | GCC | GAC | TAT | CTG | TAT | 672 |
| Ser | Leu | Ala | Ser | Met | Gly | Ile | Tyr | Val | Phe | Asp | Ala | Asp | Tyr | Leu | Tyr | |
| | 210 | | | | | 215 | | | | | 220 | | | | | |
| GAA | CTG | CTG | GAA | GAA | GAC | GAT | CGC | GAT | GAG | AAC | TCC | AGC | CAC | GAC | TTT | 720 |
| Glu | Leu | Leu | Glu | Glu | Asp | Asp | Arg | Asp | Glu | Asn | Ser | Ser | His | Asp | Phe | |
| 225 | | | | | 230 | | | | | 235 | | | | | 240 | |
| GGC | AAA | GAT | TTG | ATT | CCC | AAG | ATC | ACC | GAA | GCC | GGT | CTG | GCC | TAT | GCG | 768 |
| Gly | Lys | Asp | Leu | Ile | Pro | Lys | Ile | Thr | Glu | Ala | Gly | Leu | Ala | Tyr | Ala | |
| | | | | 245 | | | | | 250 | | | | | 255 | | |
| CAC | CCG | TTC | CCG | CTC | TCT | TGC | GTA | CAA | TCC | GAC | CCG | GAT | GCC | GAG | CCG | 816 |
| His | Pro | Phe | Pro | Leu | Ser | Cys | Val | Gln | Ser | Asp | Pro | Asp | Ala | Glu | Pro | |
| | | | 260 | | | | | 265 | | | | | 270 | | | |
| TAC | TGG | CGC | GAT | GTG | GGT | ACG | CTG | GAA | GCT | TAC | TGG | AAA | GCG | AAC | CTC | 864 |
| Tyr | Trp | Arg | Asp | Val | Gly | Thr | Leu | Glu | Ala | Tyr | Trp | Lys | Ala | Asn | Leu | |
| | | 275 | | | | | 280 | | | | | 285 | | | | |
| GAT | CTG | GCC | TCT | GTG | GTG | CCG | GAG | CTG | GAT | ATG | TAC | GAT | CGC | AAT | TGG | 912 |
| Asp | Leu | Ala | Ser | Val | Val | Pro | Glu | Leu | Asp | Met | Tyr | Asp | Arg | Asn | Trp | |
| | 290 | | | | | 295 | | | | | 300 | | | | | |
| CCA | ATT | CGC | ACC | TAC | AAT | GAA | TCA | TTA | CCG | CCA | GCG | AAA | TTC | GTG | CAG | 960 |
| Pro | Ile | Arg | Thr | Tyr | Asn | Glu | Ser | Leu | Pro | Pro | Ala | Lys | Phe | Val | Gln | |
| 305 | | | | | 310 | | | | | 315 | | | | | 320 | |
| GAT | CGC | TCC | GGT | AGC | CAC | GGG | ATG | ACC | CTT | AAC | TCA | CTG | GTT | TCC | GGC | 1008 |
| Asp | Arg | Ser | Gly | Ser | His | Gly | Met | Thr | Leu | Asn | Ser | Leu | Val | Ser | Gly | |
| | | | | 325 | | | | | 330 | | | | | 335 | | |
| GGT | TGT | GTG | ATC | TCC | GGT | TCG | GTG | GTG | GTG | CAG | TCC | GTT | CTG | TTC | TCG | 1056 |
| Gly | Cys | Val | Ile | Ser | Gly | Ser | Val | Val | Val | Gln | Ser | Val | Leu | Phe | Ser | |
| | | | 340 | | | | | 345 | | | | | 350 | | | |
| CGC | GTT | CGC | GTG | AAT | TCA | TTC | TGC | AAC | ATT | GAT | TCC | GCC | GTA | TTG | TTA | 1104 |
| Arg | Val | Arg | Val | Asn | Ser | Phe | Cys | Asn | Ile | Asp | Ser | Ala | Val | Leu | Leu | |
| | | 355 | | | | | 360 | | | | | 365 | | | | |
| CCG | GAA | GTA | TGG | GTA | GGT | CGC | TCG | TGC | CGT | CTG | CGC | CGC | TGC | GTC | ATC | 1152 |
| Pro | Glu | Val | Trp | Val | Gly | Arg | Ser | Cys | Arg | Leu | Arg | Arg | Cys | Val | Ile | |
| | 370 | | | | | 375 | | | | | 380 | | | | | |
| GAT | CGT | GCT | TGT | GTT | ATT | CCG | GAA | GGC | ATG | GTG | ATT | GGT | GAA | AAC | GCA | 1200 |
| Asp | Arg | Ala | Cys | Val | Ile | Pro | Glu | Gly | Met | Val | Ile | Gly | Glu | Asn | Ala | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| GAG | GAA | GAT | GCA | CGT | CGT | TTC | TAT | CGT | TCA | GAA | GAA | GGC | ATC | GTG | CTG | 1248 |
| Glu | Glu | Asp | Ala | Arg | Arg | Phe | Tyr | Arg | Ser | Glu | Glu | Gly | Ile | Val | Leu | |
| | | | | 405 | | | | | 410 | | | | | 415 | | |
| GTA | ACG | CGC | GAA | ATG | CTA | CGG | AAG | TTA | GGG | CAT | AAA | CAG | GAG | CGA | TAA | 1296 |
| Val | Thr | Arg | Glu | Met | Leu | Arg | Lys | Leu | Gly | His | Lys | Gln | Glu | Arg | | |
| | | | 420 | | | | | 425 | | | | | 430 | | | |

( 2 ) INFORMATION FOR SEQ ID NO:2:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Val | Ser | Leu | Glu | Lys | Asn | Asp | His | Leu | Met | Leu | Ala | Arg | Gln | Leu |
| 1 | | | | 5 | | | | | 10 | | | | | 15 | |
| Pro | Leu | Lys | Ser | Val | Ala | Leu | Ile | Leu | Ala | Gly | Gly | Arg | Gly | Thr | Arg |
| | | | 20 | | | | | 25 | | | | | 30 | | |
| Leu | Lys | Asp | Leu | Thr | Asn | Lys | Arg | Ala | Lys | Pro | Ala | Val | His | Phe | Gly |
| | | 35 | | | | | 40 | | | | | 45 | | | |
| Gly | Lys | Phe | Arg | Ile | Ile | Asp | Phe | Ala | Leu | Ser | Asn | Cys | Ile | Asn | Ser |
| | 50 | | | | | 55 | | | | | 60 | | | | |
| Gly | Ile | Arg | Arg | Met | Gly | Val | Ile | Thr | Gln | Tyr | Gln | Ser | His | Thr | Leu |
| 65 | | | | | 70 | | | | | 75 | | | | | 80 |
| Val | Gln | His | Ile | Gln | Arg | Gly | Trp | Ser | Phe | Phe | Asn | Glu | Glu | Met | Asn |
| | | | | 85 | | | | | 90 | | | | | 95 | |
| Glu | Phe | Val | Asp | Leu | Leu | Pro | Ala | Gln | Gln | Arg | Met | Lys | Gly | Glu | Asn |
| | | | 100 | | | | | 105 | | | | | 110 | | |
| Trp | Tyr | Arg | Gly | Thr | Ala | Asp | Ala | Val | Thr | Gln | Asn | Leu | Asp | Ile | Ile |
| | | 115 | | | | | 120 | | | | | 125 | | | |
| Arg | Arg | Tyr | Lys | Ala | Glu | Tyr | Val | Val | Ile | Leu | Ala | Gly | Asp | His | Ile |
| | 130 | | | | | 135 | | | | | 140 | | | | |
| Tyr | Lys | Gln | Asp | Tyr | Ser | Arg | Met | Leu | Ile | Asp | His | Val | Glu | Lys | Gly |
| 145 | | | | | 150 | | | | | 155 | | | | | 160 |
| Val | Arg | Cys | Thr | Val | Val | Cys | Met | Pro | Val | Pro | Ile | Glu | Glu | Ala | Ser |
| | | | | 165 | | | | | 170 | | | | | 175 | |
| Ala | Phe | Gly | Val | Met | Ala | Val | Asp | Glu | Asn | Asp | Lys | Thr | Ile | Glu | Phe |
| | | | 180 | | | | | 185 | | | | | 190 | | |
| Val | Glu | Lys | Pro | Ala | Asn | Pro | Pro | Ser | Met | Pro | Asn | Asp | Pro | Ser | Lys |
| | | 195 | | | | | 200 | | | | | 205 | | | |
| Ser | Leu | Ala | Ser | Met | Gly | Ile | Tyr | Val | Phe | Asp | Ala | Asp | Tyr | Leu | Tyr |
| | 210 | | | | | 215 | | | | | 220 | | | | |
| Glu | Leu | Leu | Glu | Glu | Asp | Asp | Arg | Asp | Glu | Asn | Ser | Ser | His | Asp | Phe |
| 225 | | | | | 230 | | | | | 235 | | | | | 240 |
| Gly | Lys | Asp | Leu | Ile | Pro | Lys | Ile | Thr | Glu | Ala | Gly | Leu | Ala | Tyr | Ala |
| | | | | 245 | | | | | 250 | | | | | 255 | |
| His | Pro | Phe | Pro | Leu | Ser | Cys | Val | Gln | Ser | Asp | Pro | Asp | Ala | Glu | Pro |
| | | | 260 | | | | | 265 | | | | | 270 | | |
| Tyr | Trp | Arg | Asp | Val | Gly | Thr | Leu | Glu | Ala | Tyr | Trp | Lys | Ala | Asn | Leu |
| | | 275 | | | | | 280 | | | | | 285 | | | |
| Asp | Leu | Ala | Ser | Val | Val | Pro | Glu | Leu | Asp | Met | Tyr | Asp | Arg | Asn | Trp |
| | 290 | | | | | 295 | | | | | 300 | | | | |
| Pro | Ile | Arg | Thr | Tyr | Asn | Glu | Ser | Leu | Pro | Pro | Ala | Lys | Phe | Val | Gln |
| 305 | | | | | 310 | | | | | 315 | | | | | 320 |

| | | | | | | | | | | | | | | | |
|---|---|---|---|---|---|---|---|---|---|---|---|---|---|---|---|
|Asp|Arg|Ser|Gly|Ser|His|Gly|Met|Thr|Leu|Asn|Ser|Leu|Val|Ser|Gly|
| | | | |325| | |  |330| | | |  |  |335| |
|Gly|Cys|Val|Ile|Ser|Gly|Ser|Val|Val|Gln|Ser|Val|Leu|Phe|Ser| |
| | | |340| | | |  |345| | | |  |350|  | |
|Arg|Val|Arg|Val|Asn|Ser|Phe|Cys|Asn|Ile|Asp|Ser|Ala|Val|Leu|Leu|
| | |355| | | |  |360| | | |  |365|  |  | |
|Pro|Glu|Val|Trp|Val|Gly|Arg|Ser|Cys|Arg|Leu|Arg|Arg|Cys|Val|Ile|
| |370| | | | |375| | | |  |380|  |  |  | |
|Asp|Arg|Ala|Cys|Val|Ile|Pro|Glu|Gly|Met|Val|Ile|Gly|Glu|Asn|Ala|
|385| | | | |390| | | |  |395|  |  |  |  |400|
|Glu|Glu|Asp|Ala|Arg|Arg|Phe|Tyr|Arg|Ser|Glu|Glu|Gly|Ile|Val|Leu|
| | | | |405| | | |  |410|  |  |  |415|  | |
|Val|Thr|Arg|Glu|Met|Leu|Arg|Lys|Leu|Gly|His|Lys|Gln|Glu|Arg| |
| | | |420| | | |  |425| | |  |430|  |  | |

(2) INFORMATION FOR SEQ ID NO:3:

(i) SEQUENCE CHARACTERISTICS:
        (A) LENGTH: 1296 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1293

(xi) SEQUENCE DESCRIPTION: SEQ ID NO:3:

| | | | | | | | | | | | | | | | | |
|---|---|---|---|---|---|---|---|---|---|---|---|---|---|---|---|---|
|ATG|GTT|AGT|TTA|GAG|AAG|AAC|GAT|CAC|TTA|ATG|TTG|GCG|CGC|CAG|CTG|48|
|Met|Val|Ser|Leu|Glu|Lys|Asn|Asp|His|Leu|Met|Leu|Ala|Arg|Gln|Leu| |
|1| | | |5| | | | 10| | | | |15| | |
|CCA|TTG|AAA|TCT|GTT|GCC|CTG|ATA|CTG|GCG|GGA|GGA|CGT|GGT|ACC|CGC|96|
|Pro|Leu|Lys|Ser|Val|Ala|Leu|Ile|Leu|Ala|Gly|Gly|Arg|Gly|Thr|Arg| |
| | | |20| | | |25| | | | |30| | | | |
|CTG|AAG|GAT|TTA|ACC|AAT|AAG|CGA|GCA|AAA|CCG|GCC|GTA|CAC|TTC|GGC|144|
|Leu|Lys|Asp|Leu|Thr|Asn|Lys|Arg|Ala|Lys|Pro|Ala|Val|His|Phe|Gly| |
| | |35| | | |40| | | |45| | | | | | |
|GGT|AAG|TTC|CGC|ATT|ATC|GAC|TTT|GCG|CTG|TCT|AAC|TGC|ATC|AAC|TCC|192|
|Gly|Lys|Phe|Arg|Ile|Ile|Asp|Phe|Ala|Leu|Ser|Asn|Cys|Ile|Asn|Ser| |
| |50| | | |55| | | |60| | | | | | | |
|GGG|ATC|CGT|CGT|ATG|GGC|GTG|ATC|ACC|CAG|TAC|CAG|TCC|CAC|ACT|CTG|240|
|Gly|Ile|Arg|Arg|Met|Gly|Val|Ile|Thr|Gln|Tyr|Gln|Ser|His|Thr|Leu| |
|65| | | |70| | | |75| | | | | |80| | |
|GTG|CAG|CAC|ATT|CAG|CGC|GGC|TGG|TCA|TTC|TTC|AAT|GAA|GAA|ATG|AAC|288|
|Val|Gln|His|Ile|Gln|Arg|Gly|Trp|Ser|Phe|Phe|Asn|Glu|Glu|Met|Asn| |
| | | | |85| | | | |90| | | | |95| | |
|GAG|TTT|GTC|GAT|CTG|CTG|CCA|GCA|CAG|CAG|AGA|ATG|AAA|GGG|GAA|AAC|336|
|Glu|Phe|Val|Asp|Leu|Leu|Pro|Ala|Gln|Gln|Arg|Met|Lys|Gly|Glu|Asn| |
| | | |100| | | |105| | | | |110| | | | |
|TGG|TAT|CGC|GGC|ACC|GCA|GAT|GCG|GTC|ACC|CAA|AAC|CTC|GAC|ATT|ATC|384|
|Trp|Tyr|Arg|Gly|Thr|Ala|Asp|Ala|Val|Thr|Gln|Asn|Leu|Asp|Ile|Ile| |
| | |115| | | |120| | | |  |125| | | | | |
|CGT|CGT|TAT|AAA|GCG|GAA|TAC|GTG|GTG|ATC|CTG|GCG|GGC|GAC|CAT|ATC|432|
|Arg|Arg|Tyr|Lys|Ala|Glu|Tyr|Val|Val|Ile|Leu|Ala|Gly|Asp|His|Ile| |
| |130| | | |135| | | | |140| | | | | | |
|TAC|AAG|CAA|GAC|TAC|TCG|CGT|ATG|CTT|ATC|GAT|CAC|GTC|GAA|AAA|GGT|480|
|Tyr|Lys|Gln|Asp|Tyr|Ser|Arg|Met|Leu|Ile|Asp|His|Val|Glu|Lys|Gly| |
|145| | | |150| | | | |155| | | | | |160| |
|GTA|CGT|TGT|ACC|GTT|GTT|TGT|ATG|CCA|GTA|CCG|ATT|GAA|GAA|GCC|TCC|528|
|Val|Arg|Cys|Thr|Val|Val|Cys|Met|Pro|Val|Pro|Ile|Glu|Glu|Ala|Ser| |

|  |  |  |  |  |  |  |  |  |  |  |  |  |  |  |  |
|---|---|---|---|---|---|---|---|---|---|---|---|---|---|---|---|
|  |  |  |  | 165 |  |  |  |  | 170 |  |  |  |  | 175 |  |
| GCA | TTT | GGC | GTT | ATG | GCG | GTT | GAT | GAG | AAC | GAT | AAA | ACT | ATC | GAA | TTC | 576
| Ala | Phe | Gly | Val | Met | Ala | Val | Asp | Glu | Asn | Asp | Lys | Thr | Ile | Glu | Phe |
|  |  |  | 180 |  |  |  |  | 185 |  |  |  |  | 190 |  |  |
| GTG | GAA | AAA | CCT | GCT | AAC | CCG | CCG | TCA | ATG | CCG | AAC | GAT | CCG | AGC | AAA | 624
| Val | Glu | Lys | Pro | Ala | Asn | Pro | Pro | Ser | Met | Pro | Asn | Asp | Pro | Ser | Lys |
|  |  | 195 |  |  |  |  | 200 |  |  |  |  | 205 |  |  |  |
| TCT | CTG | GCG | AGT | ATG | GGT | ATC | TAC | GTC | TTT | GAC | GCC | GAC | TAT | CTG | TAT | 672
| Ser | Leu | Ala | Ser | Met | Gly | Ile | Tyr | Val | Phe | Asp | Ala | Asp | Tyr | Leu | Tyr |
|  | 210 |  |  |  |  | 215 |  |  |  |  | 220 |  |  |  |  |
| GAA | CTG | CTG | GAA | GAA | GAC | GAT | CGC | GAT | GAG | AAC | TCC | AGC | CAC | GAC | TTT | 720
| Glu | Leu | Leu | Glu | Glu | Asp | Asp | Arg | Asp | Glu | Asn | Ser | Ser | His | Asp | Phe |
| 225 |  |  |  |  | 230 |  |  |  |  | 235 |  |  |  |  | 240 |
| GGC | AAA | GAT | TTG | ATT | CCC | AAG | ATC | ACC | GAA | GCC | GGT | CTG | GCC | TAT | GCG | 768
| Gly | Lys | Asp | Leu | Ile | Pro | Lys | Ile | Thr | Glu | Ala | Gly | Leu | Ala | Tyr | Ala |
|  |  |  |  | 245 |  |  |  |  | 250 |  |  |  |  | 255 |  |
| CAC | CCG | TTC | CCG | CTC | TCT | TGC | GTA | CAA | TCC | GAC | CCG | GAT | GCC | GAG | CCG | 816
| His | Pro | Phe | Pro | Leu | Ser | Cys | Val | Gln | Ser | Asp | Pro | Asp | Ala | Glu | Pro |
|  |  |  | 260 |  |  |  |  | 265 |  |  |  |  | 270 |  |  |
| TAC | TGG | CGC | GAT | GTG | GGT | ACG | CTG | GAA | GCT | TAC | TGG | AAA | GCG | AAC | CTC | 864
| Tyr | Trp | Arg | Asp | Val | Gly | Thr | Leu | Glu | Ala | Tyr | Trp | Lys | Ala | Asn | Leu |
|  |  | 275 |  |  |  |  | 280 |  |  |  |  | 285 |  |  |  |
| GAT | CTG | GCC | TCT | GTG | GTG | CCG | GAG | CTG | GAT | ATG | TAC | GAT | CGC | AAT | TGG | 912
| Asp | Leu | Ala | Ser | Val | Val | Pro | Glu | Leu | Asp | Met | Tyr | Asp | Arg | Asn | Trp |
|  | 290 |  |  |  |  | 295 |  |  |  |  | 300 |  |  |  |  |
| CCA | ATT | CGC | ACC | TAC | AAT | GAA | TCA | TTA | CCG | CCA | GCG | AAA | TTC | GTG | CAG | 960
| Pro | Ile | Arg | Thr | Tyr | Asn | Glu | Ser | Leu | Pro | Pro | Ala | Lys | Phe | Val | Gln |
| 305 |  |  |  |  | 310 |  |  |  |  | 315 |  |  |  |  | 320 |
| GAT | CGC | TCC | GGT | AGC | CAC | GGG | ATG | ACC | CTT | AAC | TCA | CTG | GTT | TCC | GAC | 1008
| Asp | Arg | Ser | Gly | Ser | His | Gly | Met | Thr | Leu | Asn | Ser | Leu | Val | Ser | Asp |
|  |  |  |  | 325 |  |  |  |  | 330 |  |  |  |  | 335 |  |
| GGT | TGT | GTG | ATC | TCC | GGT | TCG | GTG | GTG | GTG | CAG | TCC | GTT | CTG | TTC | TCG | 1056
| Gly | Cys | Val | Ile | Ser | Gly | Ser | Val | Val | Val | Gln | Ser | Val | Leu | Phe | Ser |
|  |  |  | 340 |  |  |  |  | 345 |  |  |  |  | 350 |  |  |
| CGC | GTT | CGC | GTG | AAT | TCA | TTC | TGC | AAC | ATT | GAT | TCC | GCC | GTA | TTG | TTA | 1104
| Arg | Val | Arg | Val | Asn | Ser | Phe | Cys | Asn | Ile | Asp | Ser | Ala | Val | Leu | Leu |
|  |  | 355 |  |  |  |  | 360 |  |  |  |  | 365 |  |  |  |
| CCG | GAA | GTA | TGG | GTA | GGT | CGC | TCG | TGC | CGT | CTG | CGC | CGC | TGC | GTC | ATC | 1152
| Pro | Glu | Val | Trp | Val | Gly | Arg | Ser | Cys | Arg | Leu | Arg | Arg | Cys | Val | Ile |
|  | 370 |  |  |  |  | 375 |  |  |  |  | 380 |  |  |  |  |
| GAT | CGT | GCT | TGT | GTT | ATT | CCG | GAA | GGC | ATG | GTG | ATT | GGT | GAA | AAC | GCA | 1200
| Asp | Arg | Ala | Cys | Val | Ile | Pro | Glu | Gly | Met | Val | Ile | Gly | Glu | Asn | Ala |
| 385 |  |  |  |  | 390 |  |  |  |  | 395 |  |  |  |  | 400 |
| GAG | GAA | GAT | GCA | CGT | CGT | TTC | TAT | CGT | TCA | GAA | GAA | GGC | ATC | GTG | CTG | 1248
| Glu | Glu | Asp | Ala | Arg | Arg | Phe | Tyr | Arg | Ser | Glu | Glu | Gly | Ile | Val | Leu |
|  |  |  |  | 405 |  |  |  |  | 410 |  |  |  |  | 415 |  |
| GTA | ACG | CGC | GAA | ATG | CTA | CGG | AAG | TTA | GGG | CAT | AAA | CAG | GAG | CGA | TAA | 1296
| Val | Thr | Arg | Glu | Met | Leu | Arg | Lys | Leu | Gly | His | Lys | Gln | Glu | Arg |  |
|  |  |  | 420 |  |  |  |  | 425 |  |  |  |  | 430 |  |  |

( 2 ) INFORMATION FOR SEQ ID NO:4:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Val | Ser | Leu | Glu | Lys | Asn | Asp | His | Leu | Met | Leu | Ala | Arg | Gln | Leu |
|---|---|---|---|---|---|---|---|---|---|---|---|---|---|---|---|
| 1 |  |  |  | 5 |  |  |  |  | 10 |  |  |  |  | 15 |  |

```
Pro Leu Lys Ser Val Ala Leu Ile Leu Ala Gly Gly Arg Gly Thr Arg
            20                  25                  30

Leu Lys Asp Leu Thr Asn Lys Arg Ala Lys Pro Ala Val His Phe Gly
            35                  40                  45

Gly Lys Phe Arg Ile Ile Asp Phe Ala Leu Ser Asn Cys Ile Asn Ser
            50                  55                  60

Gly Ile Arg Arg Met Gly Val Ile Thr Gln Tyr Gln Ser His Thr Leu
 65                  70                  75                   80

Val Gln His Ile Gln Arg Gly Trp Ser Phe Phe Asn Glu Glu Met Asn
                 85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Val Ile Leu Ala Gly Asp His Ile
    130                 135                 140

Tyr Lys Gln Asp Tyr Ser Arg Met Leu Ile Asp His Val Glu Lys Gly
145                 150                 155                 160

Val Arg Cys Thr Val Val Cys Met Pro Val Pro Ile Glu Glu Ala Ser
                165                 170                 175

Ala Phe Gly Val Met Ala Val Asp Glu Asn Asp Lys Thr Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
    210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Pro Glu Leu Asp Met Tyr Asp Arg Asn Trp
290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Asp
                325                 330                 335

Gly Cys Val Ile Ser Gly Ser Val Val Val Gln Ser Val Leu Phe Ser
            340                 345                 350

Arg Val Arg Val Asn Ser Phe Cys Asn Ile Asp Ser Ala Val Leu Leu
        355                 360                 365

Pro Glu Val Trp Val Gly Arg Ser Cys Arg Leu Arg Arg Cys Val Ile
    370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Glu Gly Ile Val Leu
                405                 410                 415

Val Thr Arg Glu Met Leu Arg Lys Leu Gly His Lys Gln Glu Arg
            420                 425                 430
```

( 2 ) INFORMATION FOR SEQ ID NO:5:

( i ) SEQUENCE CHARACTERISTICS:
        ( A ) LENGTH: 355 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 88..354

( x i ) SEQUENCE DESCRIPTION: SEQ ID NO:5:

```
AAGCTTGTTC TCATTGTTGT TATCATTATA TATAGATGAC CAAAGCACTA GACCAAACCT        60

CAGTCACACA AAGAGTAAAG AAGAACA ATG GCT TCC TCT ATG CTC TCT TCC           111
                             Met Ala Ser Ser Met Leu Ser Ser
                              1               5

GCT ACT ATG GTT GCC TCT CCG GCT CAG GCC ACT ATG GTC GCT CCT TTC         159
Ala Thr Met Val Ala Ser Pro Ala Gln Ala Thr Met Val Ala Pro Phe
         10              15                  20

AAC GGA CTT AAG TCC TCC GCT GCC TTC CCA GCC ACC CGC AAG GCT AAC         207
Asn Gly Leu Lys Ser Ser Ala Ala Phe Pro Ala Thr Arg Lys Ala Asn
 25              30                  35                  40

AAC GAC ATT ACT TCC ATC ACA AGC AAC GGC GGA AGA GTT AAC TGC ATG         255
Asn Asp Ile Thr Ser Ile Thr Ser Asn Gly Gly Arg Val Asn Cys Met
                 45                  50                  55

CAG GTG TGG CCT CCG ATT GGA AAG AAG AAG TTT GAG ACT CTC TCT TAC         303
Gln Val Trp Pro Pro Ile Gly Lys Lys Lys Phe Glu Thr Leu Ser Tyr
                 60                  65                  70

CTT CCT GAC CTT ACC GAT TCC GGT GGT CGC GTC AAC TGC ATG CAG GCC         351
Leu Pro Asp Leu Thr Asp Ser Gly Gly Arg Val Asn Cys Met Gln Ala
                 75                  80                  85

ATG G                                                                   355
Met
```

( 2 ) INFORMATION FOR SEQ ID NO:6:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Ser Ser Met Leu Ser Ser Ala Thr Met Val Ala Ser Pro Ala
 1               5                  10                  15

Gln Ala Thr Met Val Ala Pro Phe Asn Gly Leu Lys Ser Ser Ala Ala
                 20                  25                  30

Phe Pro Ala Thr Arg Lys Ala Asn Asn Asp Ile Thr Ser Ile Thr Ser
                 35                  40                  45

Asn Gly Gly Arg Val Asn Cys Met Gln Val Trp Pro Pro Ile Gly Lys
                 50                  55                  60

Lys Lys Phe Glu Thr Leu Ser Tyr Leu Pro Asp Leu Thr Asp Ser Gly
 65                  70                  75                  80

Gly Arg Val Asn Cys Met Gln Ala Met
                 85
```

( 2 ) INFORMATION FOR SEQ ID NO:7:

( i ) SEQUENCE CHARACTERISTICS:
        ( A ) LENGTH: 1575 base pairs (B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 3..1565

(xi) SEQUENCE DESCRIPTION: SEQ ID NO:7:

| | | | | | | | | | | | | | | | | |
|---|---|---|---|---|---|---|---|---|---|---|---|---|---|---|---|---|
| CC | ATG | GCG | GCT | TCC | ATT | GGA | GCC | TTA | AAA | TCT | TCA | CCT | TCT | TCT | AAC | 47 |
| | Met | Ala | Ala | Ser | Ile | Gly | Ala | Leu | Lys | Ser | Ser | Pro | Ser | Ser | Asn | |
| | 1 | | | | 5 | | | | | 10 | | | | | 15 | |
| AAT | TGC | ATC | AAT | GAG | AGA | AGA | AAT | GAT | TCT | ACA | CGT | GCT | GTA | TCC | AGC | 95 |
| Asn | Cys | Ile | Asn | Glu | Arg | Arg | Asn | Asp | Ser | Thr | Arg | Ala | Val | Ser | Ser | |
| | | | | 20 | | | | | 25 | | | | | 30 | | |
| AGA | AAT | CTC | TCA | TTT | TCG | TCT | TCT | CAT | CTC | GCC | GGA | GAC | AAG | TTG | ATG | 143 |
| Arg | Asn | Leu | Ser | Phe | Ser | Ser | Ser | His | Leu | Ala | Gly | Asp | Lys | Leu | Met | |
| | | | 35 | | | | | 40 | | | | | 45 | | | |
| CCT | GTA | TCG | TCC | TTA | CGT | TCC | CAA | GGA | GTC | CGA | TTC | AAT | GTG | AGA | AGA | 191 |
| Pro | Val | Ser | Ser | Leu | Arg | Ser | Gln | Gly | Val | Arg | Phe | Asn | Val | Arg | Arg | |
| | | 50 | | | | | 55 | | | | | 60 | | | | |
| AGT | CCA | ATG | ATT | GTG | TCG | CCA | AAG | GCT | GTT | TCT | GAT | TCG | CAG | AAT | TCA | 239 |
| Ser | Pro | Met | Ile | Val | Ser | Pro | Lys | Ala | Val | Ser | Asp | Ser | Gln | Asn | Ser | |
| | 65 | | | | | 70 | | | | | 75 | | | | | |
| CAG | ACA | TGT | CTA | GAC | CCA | GAT | GCT | AGC | CGG | AGT | GTT | TTG | GGA | ATT | ATT | 287 |
| Gln | Thr | Cys | Leu | Asp | Pro | Asp | Ala | Ser | Arg | Ser | Val | Leu | Gly | Ile | Ile | |
| 80 | | | | | 85 | | | | | 90 | | | | | 95 | |
| CTT | GGA | GGT | GGA | GCT | GGG | ACC | CGA | CTT | TAT | CCT | CTA | ACT | AAA | AAA | AGA | 335 |
| Leu | Gly | Gly | Gly | Ala | Gly | Thr | Arg | Leu | Tyr | Pro | Leu | Thr | Lys | Lys | Arg | |
| | | | | 100 | | | | | 105 | | | | | 110 | | |
| GCA | AAG | CCA | GCT | GTT | CCA | CTT | GGA | GCA | AAT | TAT | CGT | CTG | ATT | GAC | ATT | 383 |
| Ala | Lys | Pro | Ala | Val | Pro | Leu | Gly | Ala | Asn | Tyr | Arg | Leu | Ile | Asp | Ile | |
| | | | 115 | | | | | 120 | | | | | 125 | | | |
| CCT | GTA | AGC | AAC | TGC | TTG | AAC | AGT | AAT | ATA | TCC | AAG | ATT | TAT | GTT | CTC | 431 |
| Pro | Val | Ser | Asn | Cys | Leu | Asn | Ser | Asn | Ile | Ser | Lys | Ile | Tyr | Val | Leu | |
| | | 130 | | | | | 135 | | | | | 140 | | | | |
| ACA | CAA | TTC | AAC | TCT | GCC | TCT | CTG | AAT | CGC | CAC | CTT | TCA | CGA | GCA | TAT | 479 |
| Thr | Gln | Phe | Asn | Ser | Ala | Ser | Leu | Asn | Arg | His | Leu | Ser | Arg | Ala | Tyr | |
| | 145 | | | | | 150 | | | | | 155 | | | | | |
| GCT | AGC | AAC | ATG | GGA | GGA | TAC | AAA | AAC | GAG | GGC | TTT | GTG | GAA | GTT | CTT | 527 |
| Ala | Ser | Asn | Met | Gly | Gly | Tyr | Lys | Asn | Glu | Gly | Phe | Val | Glu | Val | Leu | |
| 160 | | | | | 165 | | | | | 170 | | | | | 175 | |
| GCT | GCT | CAA | CAA | AGT | CCA | GAG | AAC | CCC | GAT | TGG | TTC | CAG | GGC | ACG | GCT | 575 |
| Ala | Ala | Gln | Gln | Ser | Pro | Glu | Asn | Pro | Asp | Trp | Phe | Gln | Gly | Thr | Ala | |
| | | | | 180 | | | | | 185 | | | | | 190 | | |
| GAT | GCT | GTC | AGA | CAA | TAT | CTG | TGG | TTG | TTT | GAG | GAG | CAT | ACT | GTT | CTT | 623 |
| Asp | Ala | Val | Arg | Gln | Tyr | Leu | Trp | Leu | Phe | Glu | Glu | His | Thr | Val | Leu | |
| | | | 195 | | | | | 200 | | | | | 205 | | | |
| GAA | TAC | CTT | ATA | CTT | GCT | GGA | GAT | CAT | CTG | TAT | CGA | ATG | GAT | TAT | GAA | 671 |
| Glu | Tyr | Leu | Ile | Leu | Ala | Gly | Asp | His | Leu | Tyr | Arg | Met | Asp | Tyr | Glu | |
| | | 210 | | | | | 215 | | | | | 220 | | | | |
| AAG | TTT | ATT | CAA | GCC | CAC | AGA | GAA | ACA | GAT | GCT | GAT | ATT | ACC | GTT | GCC | 719 |
| Lys | Phe | Ile | Gln | Ala | His | Arg | Glu | Thr | Asp | Ala | Asp | Ile | Thr | Val | Ala | |
| | 225 | | | | | 230 | | | | | 235 | | | | | |
| GCA | CTG | CCA | ATG | GAC | GAG | AAG | CGT | GCC | ACT | GCA | TTC | GGT | CTC | ATG | AAG | 767 |
| Ala | Leu | Pro | Met | Asp | Glu | Lys | Arg | Ala | Thr | Ala | Phe | Gly | Leu | Met | Lys | |
| 240 | | | | | 245 | | | | | 250 | | | | | 255 | |
| ATT | GAC | GAA | GAA | GGA | CGC | ATT | ATT | GAA | TTT | GCA | GAG | AAA | CCG | CAA | GGA | 815 |
| Ile | Asp | Glu | Glu | Gly | Arg | Ile | Ile | Glu | Phe | Ala | Glu | Lys | Pro | Gln | Gly | |
| | | | | 260 | | | | | 265 | | | | | 270 | | |

| | | | | | | | | | | | | | | | | |
|---|---|---|---|---|---|---|---|---|---|---|---|---|---|---|---|---|
| GAG | CAA | TTG | CAA | GCA | ATG | AAA | GTG | GAT | ACT | ACC | ATT | TTA | GGT | CTT | GAT | 863 |
| Glu | Gln | Leu | Gln 275 | Ala | Met | Lys | Val | Asp 280 | Thr | Thr | Ile | Leu | Gly 285 | Leu | Asp | |
| GAC | AAG | AGA | GCT | AAA | GAA | ATG | CCT | TTC | ATT | GCC | AGT | ATG | GGT | ATA | TAT | 911 |
| Asp | Lys | Arg 290 | Ala | Lys | Glu | Met | Pro 295 | Phe | Ile | Ala | Ser | Met 300 | Gly | Ile | Tyr | |
| GTC | ATT | AGC | AAA | GAC | GTG | ATG | TTA | AAC | CTA | CTT | CGT | GAC | AAG | TTC | CCT | 959 |
| Val | Ile 305 | Ser | Lys | Asp | Val | Met 310 | Leu | Asn | Leu | Leu | Arg 315 | Asp | Lys | Phe | Pro | |
| GGG | GCC | AAT | GAT | TTT | GGT | AGT | GAA | GTT | ATT | CCT | GGT | GCA | ACT | TCA | CTT | 1007 |
| Gly 320 | Ala | Asn | Asp | Phe | Gly 325 | Ser | Glu | Val | Ile | Pro 330 | Gly | Ala | Thr | Ser | Leu 335 | |
| GGG | ATG | AGA | GTG | CAA | GCT | TAT | TTA | TAT | GAT | GGG | TAC | TGG | GAA | GAT | ATT | 1055 |
| Gly | Met | Arg | Val | Gln 340 | Ala | Tyr | Leu | Tyr | Asp 345 | Gly | Tyr | Trp | Glu | Asp 350 | Ile | |
| GGT | ACC | ATT | GAA | GCT | TTC | TAC | AAT | GCC | AAT | TTG | GGC | ATT | ACA | AAA | AAG | 1103 |
| Gly | Thr | Ile | Glu 355 | Ala | Phe | Tyr | Asn | Ala 360 | Asn | Leu | Gly | Ile | Thr 365 | Lys | Lys | |
| CCG | GTG | CCA | GAT | TTT | AGC | TTT | TAC | GAC | CGA | TCA | GCC | CCA | ATC | TAC | ACC | 1151 |
| Pro | Val | Pro 370 | Asp | Phe | Ser | Phe | Tyr 375 | Asp | Arg | Ser | Ala | Pro 380 | Ile | Tyr | Thr | |
| CAA | CCT | CGA | TAT | CTA | CCA | CCA | TCA | AAA | ATG | CTT | GAT | GCT | GAT | GTC | ACA | 1199 |
| Gln | Pro 385 | Arg | Tyr | Leu | Pro | Pro 390 | Ser | Lys | Met | Leu | Asp 395 | Ala | Asp | Val | Thr | |
| GAT | AGT | GTC | ATT | GGT | GAA | GGT | TGT | GTG | ATC | AAG | AAC | TGT | AAG | ATT | CAT | 1247 |
| Asp 400 | Ser | Val | Ile | Gly | Glu 405 | Gly | Cys | Val | Ile | Lys 410 | Asn | Cys | Lys | Ile | His 415 | |
| CAT | TCC | GTG | GTT | GGA | CTC | AGA | TCA | TGC | ATA | TCA | GAG | GGA | GCA | ATT | ATA | 1295 |
| His | Ser | Val | Val | Gly 420 | Leu | Arg | Ser | Cys | Ile 425 | Ser | Glu | Gly | Ala | Ile 430 | Ile | |
| GAA | GAC | TCA | CTT | TTG | ATG | GGG | GCA | GAT | TAC | TAT | GAG | ACT | GAT | GCT | GAC | 1343 |
| Glu | Asp | Ser | Leu 435 | Leu | Met | Gly | Ala | Asp 440 | Tyr | Tyr | Glu | Thr | Asp 445 | Ala | Asp | |
| AGG | AAG | TTG | CTG | GCT | GCA | AAG | GGC | AGT | GTC | CCA | ATT | GGC | ATC | GGC | AAG | 1391 |
| Arg | Lys | Leu 450 | Leu | Ala | Ala | Lys | Gly 455 | Ser | Val | Pro | Ile | Gly 460 | Ile | Gly | Lys | |
| AAT | TGT | CAC | ATT | AAA | AGA | GCC | ATT | ATC | GAC | AAG | AAT | GCC | CGT | ATA | GGG | 1439 |
| Asn | Cys 465 | His | Ile | Lys | Arg | Ala 470 | Ile | Ile | Asp | Lys | Asn 475 | Ala | Arg | Ile | Gly | |
| GAC | AAT | GTG | AAG | ATT | ATT | AAC | AAA | GAC | AAC | GTT | CAA | GAA | GCG | GCT | AGG | 1487 |
| Asp | Asn | Val | Lys 480 | Ile | Ile | Asn | Lys | Asp 485 | Asn | Val | Gln | Glu | Ala 490 | Ala | Arg 495 | |
| GAA | ACA | GAT | GGA | TAC | TTC | ATC | AAG | AGT | GGG | ATT | GTC | ACC | GTC | ATC | AAG | 1535 |
| Glu | Thr | Asp | Gly | Tyr 500 | Phe | Ile | Lys | Ser | Gly 505 | Ile | Val | Thr | Val | Ile 510 | Lys | |
| GAT | GCT | TTG | ATT | CCA | AGT | GGA | ATC | ATC | ATC | TGATGAGCTC | | | | | | 1575 |
| Asp | Ala | Leu | Ile 515 | Pro | Ser | Gly | Ile | Ile 520 | Ile | | | | | | | |

( 2 ) INFORMATION FOR SEQ ID NO:8:

( i ) SEQUENCE CHARACTERISTICS:
        ( A ) LENGTH: 521 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Met Ala Ala Ser Ile Gly Ala Leu Lys Ser Ser Pro Ser Ser Asn Asn
1               5                   10                  15

Cys Ile Asn Glu Arg Arg Asn Asp Ser Thr Arg Ala Val Ser Ser Arg

|   |     |     |     |     |  20 |     |     |     |     |  25 |     |     |     |     |  30 |     |     |
|---|-----|-----|-----|-----|-----|-----|-----|-----|-----|-----|-----|-----|-----|-----|-----|-----|-----|

Asn Leu Ser Phe Ser Ser Ser His Leu Ala Gly Asp Lys Leu Met Pro
         35                  40              45

Val Ser Ser Leu Arg Ser Gln Gly Val Arg Phe Asn Val Arg Arg Ser
     50                  55                  60

Pro Met Ile Val Ser Pro Lys Ala Val Ser Asp Ser Gln Asn Ser Gln
65                   70                  75                   80

Thr Cys Leu Asp Pro Asp Ala Ser Arg Ser Val Leu Gly Ile Ile Leu
                 85                  90                   95

Gly Gly Gly Ala Gly Thr Arg Leu Tyr Pro Leu Thr Lys Lys Arg Ala
             100             105             110

Lys Pro Ala Val Pro Leu Gly Ala Asn Tyr Arg Leu Ile Asp Ile Pro
         115             120             125

Val Ser Asn Cys Leu Asn Ser Asn Ile Ser Lys Ile Tyr Val Leu Thr
    130             135             140

Gln Phe Asn Ser Ala Ser Leu Asn Arg His Leu Ser Arg Ala Tyr Ala
145             150             155             160

Ser Asn Met Gly Gly Tyr Lys Asn Glu Gly Phe Val Glu Val Leu Ala
             165             170             175

Ala Gln Gln Ser Pro Glu Asn Pro Asp Trp Phe Gln Gly Thr Ala Asp
             180             185             190

Ala Val Arg Gln Tyr Leu Trp Leu Phe Glu Glu His Thr Val Leu Glu
         195             200             205

Tyr Leu Ile Leu Ala Gly Asp His Leu Tyr Arg Met Asp Tyr Glu Lys
    210             215             220

Phe Ile Gln Ala His Arg Glu Thr Asp Ala Asp Ile Thr Val Ala Ala
225             230             235             240

Leu Pro Met Asp Glu Lys Arg Ala Thr Ala Phe Gly Leu Met Lys Ile
             245             250             255

Asp Glu Glu Gly Arg Ile Ile Glu Phe Ala Glu Lys Pro Gln Gly Glu
             260             265             270

Gln Leu Gln Ala Met Lys Val Asp Thr Thr Ile Leu Gly Leu Asp Asp
    275             280             285

Lys Arg Ala Lys Glu Met Pro Phe Ile Ala Ser Met Gly Ile Tyr Val
    290             295             300

Ile Ser Lys Asp Val Met Leu Asn Leu Leu Arg Asp Lys Phe Pro Gly
305             310             315             320

Ala Asn Asp Phe Gly Ser Glu Val Ile Pro Gly Ala Thr Ser Leu Gly
             325             330             335

Met Arg Val Gln Ala Tyr Leu Tyr Asp Gly Tyr Trp Glu Asp Ile Gly
             340             345             350

Thr Ile Glu Ala Phe Tyr Asn Ala Asn Leu Gly Ile Thr Lys Lys Pro
         355             360             365

Val Pro Asp Phe Ser Phe Tyr Asp Arg Ser Ala Pro Ile Tyr Thr Gln
    370             375             380

Pro Arg Tyr Leu Pro Pro Ser Lys Met Leu Asp Ala Asp Val Thr Asp
385             390             395             400

Ser Val Ile Gly Glu Gly Cys Val Ile Lys Asn Cys Lys Ile His His
             405             410             415

Ser Val Val Gly Leu Arg Ser Cys Ile Ser Glu Gly Ala Ile Ile Glu
             420             425             430

Asp Ser Leu Leu Met Gly Ala Asp Tyr Tyr Glu Thr Asp Ala Asp Arg
         435             440             445

-continued

| | | | | | | | | | | | | | | |
|---|---|---|---|---|---|---|---|---|---|---|---|---|---|---|
| Lys | Leu | Leu | Ala | Ala | Lys | Gly | Ser | Val | Pro | Ile | Gly | Ile | Gly | Lys | Asn |
| | 450 | | | | 455 | | | | | 460 | | | | | |
| Cys | His | Ile | Lys | Arg | Ala | Ile | Ile | Asp | Lys | Asn | Ala | Arg | Ile | Gly | Asp |
| 465 | | | | 470 | | | | | 475 | | | | | 480 | |
| Asn | Val | Lys | Ile | Ile | Asn | Lys | Asp | Asn | Val | Gln | Glu | Ala | Ala | Arg | Glu |
| | | | | 485 | | | | | 490 | | | | | 495 | |
| Thr | Asp | Gly | Tyr | Phe | Ile | Lys | Ser | Gly | Ile | Val | Thr | Val | Ile | Lys | Asp |
| | | | 500 | | | | | 505 | | | | | 510 | | |
| Ala | Leu | Ile | Pro | Ser | Gly | Ile | Ile | Ile | | | | | | | |
| | | 515 | | | | | 520 | | | | | | | | |

( 2 ) INFORMATION FOR SEQ ID NO:9:

( i ) SEQUENCE CHARACTERISTICS:
( A ) LENGTH: 1519 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..1410

( x i ) SEQUENCE DESCRIPTION: SEQ ID NO:9:

| | | | | | | | | | | | | | | | | |
|---|---|---|---|---|---|---|---|---|---|---|---|---|---|---|---|---|
| AAC | AAG | ATC | AAA | CCT | GGG | GTT | GCT | TAC | TCT | GTG | ATC | ACT | ACT | GAA | AAT | 48 |
| Asn | Lys | Ile | Lys | Pro | Gly | Val | Ala | Tyr | Ser | Val | Ile | Thr | Thr | Glu | Asn | |
| 1 | | | | 5 | | | | | 10 | | | | | 15 | | |
| GAC | ACA | CAG | ACT | GTG | TTC | GTA | GAT | ATG | CCA | CGT | CTT | GAG | AGA | CGC | CGG | 96 |
| Asp | Thr | Gln | Thr | Val | Phe | Val | Asp | Met | Pro | Arg | Leu | Glu | Arg | Arg | Arg | |
| | | | 20 | | | | | 25 | | | | | 30 | | | |
| GCA | AAT | CCA | AAG | GAT | GTG | GCT | GCA | GTC | ATA | CTG | GGA | GGA | GGA | GAA | GGG | 144 |
| Ala | Asn | Pro | Lys | Asp | Val | Ala | Ala | Val | Ile | Leu | Gly | Gly | Gly | Glu | Gly | |
| | | 35 | | | | | 40 | | | | | 45 | | | | |
| ACC | AAG | TTA | TTC | CCA | CTT | ACA | AGT | AGA | ACT | GCA | ACC | CCT | GCT | GTT | CCG | 192 |
| Thr | Lys | Leu | Phe | Pro | Leu | Thr | Ser | Arg | Thr | Ala | Thr | Pro | Ala | Val | Pro | |
| | 50 | | | | | 55 | | | | | 60 | | | | | |
| GTT | GGA | GGA | TGC | TAC | AGG | CTA | ATA | GAC | ATC | CCA | ATG | AGC | AAC | TGT | ATC | 240 |
| Val | Gly | Gly | Cys | Tyr | Arg | Leu | Ile | Asp | Ile | Pro | Met | Ser | Asn | Cys | Ile | |
| 65 | | | | | 70 | | | | | 75 | | | | | 80 | |
| AAC | AGT | GCT | ATT | AAC | AAG | ATT | TTT | GTG | CTG | ACA | CAG | TAC | AAT | TCT | GCT | 288 |
| Asn | Ser | Ala | Ile | Asn | Lys | Ile | Phe | Val | Leu | Thr | Gln | Tyr | Asn | Ser | Ala | |
| | | | | 85 | | | | | 90 | | | | | 95 | | |
| CCC | CTG | AAT | CGT | CAC | ATT | GCT | CGA | ACA | TAT | TTT | GGC | AAT | GGT | GTG | AGC | 336 |
| Pro | Leu | Asn | Arg | His | Ile | Ala | Arg | Thr | Tyr | Phe | Gly | Asn | Gly | Val | Ser | |
| | | | 100 | | | | | 105 | | | | | 110 | | | |
| TTT | GGA | GAT | GGA | TTT | GTC | GAG | GTA | CTA | GCT | GCA | ACT | CAG | ACA | CCC | GGG | 384 |
| Phe | Gly | Asp | Gly | Phe | Val | Glu | Val | Leu | Ala | Ala | Thr | Gln | Thr | Pro | Gly | |
| | | | 115 | | | | | 120 | | | | | 125 | | | |
| GAA | GCA | GGA | AAA | AAA | TGG | TTT | CAA | GGA | ACA | GCA | GAT | GCT | GTT | AGA | AAA | 432 |
| Glu | Ala | Gly | Lys | Lys | Trp | Phe | Gln | Gly | Thr | Ala | Asp | Ala | Val | Arg | Lys | |
| | | 130 | | | | | 135 | | | | | 140 | | | | |
| TTT | ATA | TGG | GTT | TTT | GAG | GAC | GCT | AAG | AAC | AAG | AAT | ATT | GAA | AAT | ATC | 480 |
| Phe | Ile | Trp | Val | Phe | Glu | Asp | Ala | Lys | Asn | Lys | Asn | Ile | Glu | Asn | Ile | |
| 145 | | | | | 150 | | | | | 155 | | | | | 160 | |
| GTT | GTA | CTA | TCT | GGG | GAT | CAT | CTT | TAT | AGG | ATG | GAT | TAT | ATG | GAG | TTG | 528 |
| Val | Val | Leu | Ser | Gly | Asp | His | Leu | Tyr | Arg | Met | Asp | Tyr | Met | Glu | Leu | |
| | | | | 165 | | | | | 170 | | | | | 175 | | |
| GTG | CAG | AAC | CAT | ATT | GAC | AGG | AAT | GCT | GAT | ATT | ACT | CTT | TCA | TGT | GCA | 576 |
| Val | Gln | Asn | His | Ile | Asp | Arg | Asn | Ala | Asp | Ile | Thr | Leu | Ser | Cys | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| CCA | GCT | GAG | GAC | AGC | CGA | GCA | TCA | GAT | TTT | GGG | CTG | GTC | AAG | ATT | GAC | 624 |
| Pro | Ala | Glu | Asp | Ser | Arg | Ala | Ser | Asp | Phe | Gly | Leu | Val | Lys | Ile | Asp | |
| | | 195 | | | | | 200 | | | | 205 | | | | | |
| AGC | AGA | GGC | AGA | GTA | GTC | CAG | TTT | GCT | GAA | AAA | CCA | AAA | GGT | TTT | GAT | 672 |
| Ser | Arg | Gly | Arg | Val | Val | Gln | Phe | Ala | Glu | Lys | Pro | Lys | Gly | Phe | Asp | |
| | 210 | | | | | 215 | | | | | 220 | | | | | |
| CTT | AAA | GCA | ATG | CAA | GTA | GAT | ACT | ACT | CTT | GTT | GGA | TTA | TCT | CCA | CAA | 720 |
| Leu | Lys | Ala | Met | Gln | Val | Asp | Thr | Thr | Leu | Val | Gly | Leu | Ser | Pro | Gln | |
| 225 | | | | | 230 | | | | | 235 | | | | | 240 | |
| GAT | GCG | AAG | AAA | TCC | CCC | TAT | ATT | GCT | TCA | ATG | GGA | GTT | TAT | GTA | TTC | 768 |
| Asp | Ala | Lys | Lys | Ser | Pro | Tyr | Ile | Ala | Ser | Met | Gly | Val | Tyr | Val | Phe | |
| | | | | 245 | | | | | 250 | | | | | 255 | | |
| AAG | ACA | GAT | GTA | TTG | TTG | AAG | CTC | TTG | AAA | TGG | AGC | TAT | CCC | ACT | TCT | 816 |
| Lys | Thr | Asp | Val | Leu | Leu | Lys | Leu | Leu | Lys | Trp | Ser | Tyr | Pro | Thr | Ser | |
| | | | 260 | | | | | 265 | | | | | 270 | | | |
| AAT | GAT | TTT | GGC | TCT | GAA | ATT | ATA | CCA | GCA | GCT | ATT | GAC | GAT | TAC | AAT | 864 |
| Asn | Asp | Phe | Gly | Ser | Glu | Ile | Ile | Pro | Ala | Ala | Ile | Asp | Asp | Tyr | Asn | |
| | | 275 | | | | | 280 | | | | | 285 | | | | |
| GTC | CAA | GCA | TAC | ATT | TTC | AAA | GAC | TAT | TGG | GAA | GAC | ATT | GGA | ACA | ATT | 912 |
| Val | Gln | Ala | Tyr | Ile | Phe | Lys | Asp | Tyr | Trp | Glu | Asp | Ile | Gly | Thr | Ile | |
| | 290 | | | | | 295 | | | | | 300 | | | | | |
| AAA | TCG | TTT | TAT | AAT | GCT | AGC | TTG | GCA | CTC | ACA | CAA | GAG | TTT | CCA | GAG | 960 |
| Lys | Ser | Phe | Tyr | Asn | Ala | Ser | Leu | Ala | Leu | Thr | Gln | Glu | Phe | Pro | Glu | |
| 305 | | | | | 310 | | | | | 315 | | | | | 320 | |
| TTC | CAA | TTT | TAC | GAT | CCA | AAA | ACA | CCT | TTT | TAC | ACA | TCT | CCT | AGG | TTC | 1008 |
| Phe | Gln | Phe | Tyr | Asp | Pro | Lys | Thr | Pro | Phe | Tyr | Thr | Ser | Pro | Arg | Phe | |
| | | | | 325 | | | | | 330 | | | | | 335 | | |
| CTT | CCA | CCA | ACC | AAG | ATA | GAC | AAT | TGC | AAG | ATT | AAG | GAT | GCC | ATA | ATC | 1056 |
| Leu | Pro | Pro | Thr | Lys | Ile | Asp | Asn | Cys | Lys | Ile | Lys | Asp | Ala | Ile | Ile | |
| | | | 340 | | | | | 345 | | | | | 350 | | | |
| TCT | CAT | GGA | TGT | TTC | TTG | CGA | GAT | TGT | TCT | GTG | GAA | CAC | TCC | ATA | GTG | 1104 |
| Ser | His | Gly | Cys | Phe | Leu | Arg | Asp | Cys | Ser | Val | Glu | His | Ser | Ile | Val | |
| | | 355 | | | | | 360 | | | | | 365 | | | | |
| GGT | GAA | AGA | TCG | CGC | TTA | GAT | TGT | GGT | GTT | GAA | CTG | AAG | GAT | ACT | TTC | 1152 |
| Gly | Glu | Arg | Ser | Arg | Leu | Asp | Cys | Gly | Val | Glu | Leu | Lys | Asp | Thr | Phe | |
| | 370 | | | | | 375 | | | | | 380 | | | | | |
| ATG | ATG | GGA | GCA | GAC | TAC | TAC | CAA | ACA | GAA | TCT | GAG | ATT | GCC | TCC | CTG | 1200 |
| Met | Met | Gly | Ala | Asp | Tyr | Tyr | Gln | Thr | Glu | Ser | Glu | Ile | Ala | Ser | Leu | |
| 385 | | | | | 390 | | | | | 395 | | | | | 400 | |
| TTA | GCA | GAG | GGG | AAA | GTA | CCG | ATT | GGA | ATT | GGG | GAA | AAT | ACA | AAA | ATA | 1248 |
| Leu | Ala | Glu | Gly | Lys | Val | Pro | Ile | Gly | Ile | Gly | Glu | Asn | Thr | Lys | Ile | |
| | | | | 405 | | | | | 410 | | | | | 415 | | |
| AGG | AAA | TGT | ATC | ATT | GAC | AAG | AAC | GCA | AAG | ATA | GGA | AAG | AAT | GTT | TCA | 1296 |
| Arg | Lys | Cys | Ile | Ile | Asp | Lys | Asn | Ala | Lys | Ile | Gly | Lys | Asn | Val | Ser | |
| | | | 420 | | | | | 425 | | | | | 430 | | | |
| ATC | ATA | AAT | AAA | GAC | GGT | GTT | CAA | GAG | GCA | GAC | CGA | CCA | GAG | GAA | GGA | 1344 |
| Ile | Ile | Asn | Lys | Asp | Gly | Val | Gln | Glu | Ala | Asp | Arg | Pro | Glu | Glu | Gly | |
| | | 435 | | | | | 440 | | | | | 445 | | | | |
| TTC | TAC | ATA | CGA | TCA | GGG | ATA | ATC | ATT | ATA | TTA | GAG | AAA | GCC | ACA | ATT | 1392 |
| Phe | Tyr | Ile | Arg | Ser | Gly | Ile | Ile | Ile | Ile | Leu | Glu | Lys | Ala | Thr | Ile | |
| | 450 | | | | | 455 | | | | | 460 | | | | | |
| AGA | GAT | GGA | ACA | GTC | ATC | TGAACTAGGG | AAGCACCTCT | TGTTAACTA | | | | | | | | 1440 |
| Arg | Asp | Gly | Thr | Val | Ile | | | | | | | | | | | |
| 465 | | | | | 470 | | | | | | | | | | | |

CTGGAGATCC AAATCTCAAC TTGAAGAAGG TCAAGGGTGA TCCTAGCACG TTCACCAGTT 1500

GACTCCCCGA AGGAAGCTT 1519

( 2 ) INFORMATION FOR SEQ ID NO:10:

( i ) SEQUENCE CHARACTERISTICS:

( A ) LENGTH: 470 amino acids
( B ) TYPE: amino acid
( D ) TOPOLOGY: linear ( i i ) MOLECULE TYPE: protein ( x i ) SEQUENCE DESCRIPTION: SEQ ID NO:10:

| Asn | Lys | Ile | Lys | Pro | Gly | Val | Ala | Tyr | Ser | Val | Ile | Thr | Thr | Glu | Asn |
|---|---|---|---|---|---|---|---|---|---|---|---|---|---|---|---|
| 1 | | | | 5 | | | | | 10 | | | | | 15 | |
| Asp | Thr | Gln | Thr | Val | Phe | Val | Asp | Met | Pro | Arg | Leu | Glu | Arg | Arg | Arg |
| | | | 20 | | | | 25 | | | | | 30 | | | |
| Ala | Asn | Pro | Lys | Asp | Val | Ala | Ala | Val | Ile | Leu | Gly | Gly | Gly | Glu | Gly |
| | | 35 | | | | 40 | | | | | | 45 | | | |
| Thr | Lys | Leu | Phe | Pro | Leu | Thr | Ser | Arg | Thr | Ala | Thr | Pro | Ala | Val | Pro |
| | 50 | | | | | 55 | | | | | 60 | | | | |
| Val | Gly | Gly | Cys | Tyr | Arg | Leu | Ile | Asp | Ile | Pro | Met | Ser | Asn | Cys | Ile |
| 65 | | | | | 70 | | | | | 75 | | | | | 80 |
| Asn | Ser | Ala | Ile | Asn | Lys | Ile | Phe | Val | Leu | Thr | Gln | Tyr | Asn | Ser | Ala |
| | | | | 85 | | | | | 90 | | | | | 95 | |
| Pro | Leu | Asn | Arg | His | Ile | Ala | Arg | Thr | Tyr | Phe | Gly | Asn | Gly | Val | Ser |
| | | | 100 | | | | | 105 | | | | | 110 | | |
| Phe | Gly | Asp | Gly | Phe | Val | Glu | Val | Leu | Ala | Ala | Thr | Gln | Thr | Pro | Gly |
| | | 115 | | | | | 120 | | | | | 125 | | | |
| Glu | Ala | Gly | Lys | Lys | Trp | Phe | Gln | Gly | Thr | Ala | Asp | Ala | Val | Arg | Lys |
| | 130 | | | | | 135 | | | | | 140 | | | | |
| Phe | Ile | Trp | Val | Phe | Glu | Asp | Ala | Lys | Asn | Lys | Asn | Ile | Glu | Asn | Ile |
| 145 | | | | | 150 | | | | | 155 | | | | | 160 |
| Val | Val | Leu | Ser | Gly | Asp | His | Leu | Tyr | Arg | Met | Asp | Tyr | Met | Glu | Leu |
| | | | | 165 | | | | | 170 | | | | | 175 | |
| Val | Gln | Asn | His | Ile | Asp | Arg | Asn | Ala | Asp | Ile | Thr | Leu | Ser | Cys | Ala |
| | | | 180 | | | | | 185 | | | | | 190 | | |
| Pro | Ala | Glu | Asp | Ser | Arg | Ala | Ser | Asp | Phe | Gly | Leu | Val | Lys | Ile | Asp |
| | | | 195 | | | | 200 | | | | | 205 | | | |
| Ser | Arg | Gly | Arg | Val | Val | Gln | Phe | Ala | Glu | Lys | Pro | Lys | Gly | Phe | Asp |
| | 210 | | | | | 215 | | | | | 220 | | | | |
| Leu | Lys | Ala | Met | Gln | Val | Asp | Thr | Thr | Leu | Val | Gly | Leu | Ser | Pro | Gln |
| 225 | | | | | 230 | | | | | 235 | | | | | 240 |
| Asp | Ala | Lys | Lys | Ser | Pro | Tyr | Ile | Ala | Ser | Met | Gly | Val | Tyr | Val | Phe |
| | | | | 245 | | | | | 250 | | | | | 255 | |
| Lys | Thr | Asp | Val | Leu | Leu | Lys | Leu | Leu | Lys | Trp | Ser | Tyr | Pro | Thr | Ser |
| | | | 260 | | | | | 265 | | | | | 270 | | |
| Asn | Asp | Phe | Gly | Ser | Glu | Ile | Ile | Pro | Ala | Ala | Ile | Asp | Asp | Tyr | Asn |
| | | 275 | | | | | 280 | | | | | 285 | | | |
| Val | Gln | Ala | Tyr | Ile | Phe | Lys | Asp | Tyr | Trp | Glu | Asp | Ile | Gly | Thr | Ile |
| | 290 | | | | | 295 | | | | | 300 | | | | |
| Lys | Ser | Phe | Tyr | Asn | Ala | Ser | Leu | Ala | Leu | Thr | Gln | Glu | Phe | Pro | Glu |
| 305 | | | | | 310 | | | | | 315 | | | | | 320 |
| Phe | Gln | Phe | Tyr | Asp | Pro | Lys | Thr | Pro | Phe | Tyr | Thr | Ser | Pro | Arg | Phe |
| | | | | 325 | | | | | 330 | | | | | 335 | |
| Leu | Pro | Pro | Thr | Lys | Ile | Asp | Asn | Cys | Lys | Ile | Lys | Asp | Ala | Ile | Ile |
| | | | 340 | | | | | 345 | | | | | 350 | | |
| Ser | His | Gly | Cys | Phe | Leu | Arg | Asp | Cys | Ser | Val | Glu | His | Ser | Ile | Val |
| | | 355 | | | | | 360 | | | | | 365 | | | |
| Gly | Glu | Arg | Ser | Arg | Leu | Asp | Cys | Gly | Val | Glu | Leu | Lys | Asp | Thr | Phe |
| | 370 | | | | | 375 | | | | | 380 | | | | |

```
Met Met Gly Ala Asp Tyr Tyr Gln Thr Glu Ser Glu Ile Ala Ser Leu
385                 390                 395                 400

Leu Ala Glu Gly Lys Val Pro Ile Gly Ile Gly Glu Asn Thr Lys Ile
                405                 410                 415

Arg Lys Cys Ile Ile Asp Lys Asn Ala Lys Ile Gly Lys Asn Val Ser
            420                 425                 430

Ile Ile Asn Lys Asp Gly Val Gln Glu Ala Asp Arg Pro Glu Glu Gly
        435                 440                 445

Phe Tyr Ile Arg Ser Gly Ile Ile Ile Ile Leu Glu Lys Ala Thr Ile
        450                 455                 460

Arg Asp Gly Thr Val Ile
465                 470
```

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:11:

GTTGATAACA AGATCTGTTA ACCATGGCGG CTTCC    35

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

CCAGTTAAAA CGGAGCTCAT CAGATGATGA TTC    33

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:13:

GTGTGAGAAC ATAAATCTTG GATATGTTAC    30

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:14:

GAATTCACAG GGCCATGGCT CTAGACCC    28

(2) INFORMATION FOR SEQ ID NO:15:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:15:

AAGATCAAAC CTGCCATGGC TTACTCTGTG ATCACTACTG    40

( 2 ) INFORMATION FOR SEQ ID NO:16:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:16:

GGGAATTCAA GCTTGGATCC CGGGCCCCCC CCCCCCCC    39

( 2 ) INFORMATION FOR SEQ ID NO:17:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:17:

GGGAATTCAA GCTTGGATCC CGGG    24

( 2 ) INFORMATION FOR SEQ ID NO:18:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:18:

CCTCTAGACA GTCGATCAGG AGCAGATGTA CG    32

( 2 ) INFORMATION FOR SEQ ID NO:19:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:19:

GGAGTTAGCC ATGGTTAGTT TAGAG    25

( 2 ) INFORMATION FOR SEQ ID NO:20:

( i ) SEQUENCE CHARACTERISTICS:
    ( A ) LENGTH: 34 base pairs
    ( B ) TYPE: nucleic acid
    ( C ) STRANDEDNESS: single ( D ) TOPOLOGY: linear ( i i ) MOLECULE TYPE: DNA (synthetic)

( x i ) SEQUENCE DESCRIPTION: SEQ ID NO:20:

GGCCGAGCTC GTCAACGCCG TCTGCGATTT GTGC  34

( 2 ) INFORMATION FOR SEQ ID NO:21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:21:

GATTTAGGTG ACACTATAG  19

( 2 ) INFORMATION FOR SEQ ID NO:22:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:22:

AGAGAGATCT AGAACAATGG CTTCCTCTAT GCTCTCTTCC GC  42

( 2 ) INFORMATION FOR SEQ ID NO:23:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:23:

GGCCGAGCTC TAGATTATCG CTCCTGTTTA TGCCCTAAC  39

( 2 ) INFORMATION FOR SEQ ID NO:24:

( i ) SEQUENCE CHARACTERISTICS:
        ( A ) LENGTH: 591 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:24:

```
AAGCTTGATA TCGAATTCCT GCAGCCCGGG GGATCTCCTT AAAACTTTTT CTGAATTACT   60
TTTCAAGATT CTTGATTCTG CACCACTAGC AATTTCCATT TTTCTTTCAG TGATTTTGGT  120
TACTTATTTG ACATTCTTGT TTTCAAGATC CAACATCATC ACTTTCCAGG TTCAAAATCT  180
TGTTTTTTTT CTTTTTTCTT TTAATGCTCT ATATTGTGGA AGTCCACAGG TGAATTTTTA  240
CGATATGGGT TTACCACTTA GCTTTCTTGT AATATTTTAT CAATTTTAGA AAATATATGT  300
GTGAAATACC TAATTTTACG TAGAGATCAT GGGTTCATAT GCGTAAAGAT TCATGTTTTT  360
GTGGTAATGC TATGAGGTAT TAGTACTGAG CATATAGCTA GCTTGGGTTT TGGGTTTACC  420
```

| | | | | | |
|---|---|---|---|---|---|
| GACCAAAAAA | AAAAATTAGT | GATATTTTCT | TTATGTAAAT | TATACTTTTC | TTGGTTGCTA | 480 |
| AAAGATAACA | TATACTTTAT | TGAGATTTGA | ATAAATCTAT | TTGATTTAGA | TCCATTGATA | 540 |
| AATCTTAATC | TTATGGGATT | ACTGATTTGT | TGATTGGCTG | CAGAAGGATC | C | 591 |

( 2 ) INFORMATION FOR SEQ ID NO:25:

( i ) SEQUENCE CHARACTERISTICS:
        ( A ) LENGTH: 1705 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

| | | | | | |
|---|---|---|---|---|---|
| AAGCTTGGGT | ACCGGGCCCC | CCCTGGAGGT | CGAGTGCCAT | CACATCCAGG | GTGTAGGCTC | 60 |
| GGGGCGTGAC | AAACTTGGTA | TCTGAGCTCA | GAGTTCAAGA | GTCTAAGGTG | TCTATAAAGT | 120 |
| CTGTGCCTTT | AGAGTCCTAG | TTATCGGTGT | GAAGCGCGCC | ACATCTATAA | CCAGGAGGCT | 180 |
| GCGACATTTA | AGAATTATCA | TACTTCTTTC | ATACTCTTTT | CGTGCAATAG | AGTTCAACTC | 240 |
| CATAAAGTCT | CTTTATAATT | CATGTTTACG | CATATCTTTG | AGATCATGCC | TCCATGTAGA | 300 |
| GTTGTCTGAG | GTCGTCCTGC | TAGAAGAAAT | ATTGATCCTC | AGGATCAAGG | GGTACCCAAT | 360 |
| GCACCAGAAG | TGCGACCCCA | AGGAAAGGTC | ACTAATGTTG | AGTTCCAGGA | TGTTATACGG | 420 |
| ATATTGAGTG | AAGTTGTGAC | CAACCAAGCT | GGACAACAAA | GAGGGAATCA | ACAAGATGTG | 480 |
| GTTGATACAT | CCAGAATCCG | TGAGTTCTTA | AGGATGAATC | CTTCAGACTT | CACCAATTCA | 540 |
| AGAGTCACTG | AGGATCTGGA | AAACTTTGTG | GAAGAGTTGT | AGAAGGTTTT | TGAGGTTATG | 600 |
| CATGTTGTTG | ATGCTGAGCG | AGTGGAACTA | ACTGCATACC | AACTGAATGG | TGTTGCTAGA | 660 |
| GTATGGTACG | ACCAATAGAA | AAAGAGTAGA | GTTGAGGGTG | CACAAATTGT | GAGTTGGGCA | 720 |
| GTGTTTGAAG | AGGCCTTCAT | GGGGCATTTC | TTTTCCCATG | AACTATATGG | CAAAGGTAAG | 780 |
| AGAATTTCCT | CACTCTTAAG | CAGGAATCCA | TGAGTGTGCA | TAAGTATAGC | CTCAAGTTCA | 840 |
| CTCAACTGTC | GCCTATGCTC | CAGAGATGGC | TGTTGATATG | AGGAGCAGGA | TGGGCTTGTT | 900 |
| TGTGTTTGGG | TTGTCTCATC | TGTCAATCAA | AGAAGGTAAG | GTTGTGATGT | GGATAAAGGA | 960 |
| CATGGACATC | GAAAGGGTAA | TGATCCTTGT | GCAACAGGTT | GAGGAAGATA | AGTTGAGGGA | 1020 |
| TAGAGAAGAG | TTCTGAAACA | AGAGGGCTAA | GAACACATGA | AATGAGTACG | TAAGCAGAAG | 1080 |
| AGTAATGCAA | ATCGGTTATC | TTTTCAATGA | AAGCCAAATA | AACCTGCTTG | ATTGTTTGCA | 1140 |
| AGTGCAACCT | GTACCAACGA | ACAAGGTGA | GTTCAAGAAT | CAGAATTCTT | AGAAATTCAG | 1200 |
| AGCTAGACCT | GCACAATCTC | AAGGTAGTGT | GGCACAAGGA | TGTAATGGGA | CTCCTGCATG | 1260 |
| TGTTAAGTAC | GGTAGGAACC | ACCCAGGAGC | GTGTCATGAT | GGCTCTGCTG | GTTGCTTCAA | 1320 |
| GTGTGGTCAG | AATGGTCACT | TCATGAGAGA | GTGCCTAAAG | AANAGGCAAG | GTAATAGCAA | 1380 |
| TGGGGGCAAT | ATATCACAAT | CTTCTTCAGT | GGCTCCACNA | GATAGAGCTG | CACCTTGAGG | 1440 |
| ATCATGGGTT | CATATGCGTA | AAGATTCATG | TTTTGTGGTA | ATGCTATGAG | GTATTAGTAC | 1500 |
| TGAGCATATA | GCTAGCTTGG | GTTTTGGGTT | TACCGACCAT | TTTTTTTAAT | TAGTGATATT | 1560 |
| TTCTTTATGT | ATTTTATACT | TTTCTTGGTT | GCTTAAAGAT | TACATATACT | TTATTGAGAT | 1620 |
| TTGAATAAAT | CTATTTGATT | TAGATCCATT | GATAAATCTT | AATCTTATGG | GATTACTGAT | 1680 |
| TTGTTGATTG | GCTGCAGAAG | GATCC | | | | 1705 |

( 2 ) INFORMATION FOR SEQ ID NO:26:

( i ) SEQUENCE CHARACTERISTICS:
    ( A ) LENGTH: 1226 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:26:

| | | | | | | |
|---|---|---|---|---|---|---|
| AAGCTTAAGC | GGTAACGAGA | TAGAAAATTA | TATTACTCCG | TTTTGTTCAT | TACTTAACAA | 60 |
| ATGCAACAGT | ATCTTGTACC | AAATCCTTTC | TCTCTTTTCA | AACTTTTCTA | TTTGGCTGTT | 120 |
| GACAGAGTAA | TCAGGATACA | AACCACAAGT | ATTTAATTGA | CTCCTCCGCC | AGATATTATG | 180 |
| ATTTATGAAT | CCTCGAAAAG | CCTATCCATT | AAGTCCTCAT | CTATGGATAT | ACTTGACAGT | 240 |
| TTCTTCCTAT | TTGGGTGTTT | TTTTCCTGTT | AAGTGGAACG | GAGACATGTT | ATGATGTATA | 300 |
| CGGGAAGCTC | GTTAAAAAAA | AAAAAACAAT | AGGAAGAAAT | GTAACAAACA | TTGAATGTTG | 360 |
| TTTTTAACCA | TCCTTCCTTT | TAGCAGTGTA | TCAATTTTGT | AATAGAACCA | TGCATCTCAA | 420 |
| TCTTAATACT | AAAAAATGCA | ACTTAAGATA | GGCTAAACCA | AGTAAAGTAA | TGTATTCAAC | 480 |
| CTTTAGAATT | GTGCATTCAT | AATTTGATCT | TGTTTGTCGT | AAAACATTAG | AAAATATATT | 540 |
| TACAGTAATT | TGGAATACAA | AGCTAAGGGG | GAAGTAACTA | CTAATATTCT | AGTGGAGGGA | 600 |
| GGGACCAGTA | CCAGTACCTA | GATATTATTT | TTAATTACTA | TAATAATAAT | TTAATTAACA | 660 |
| CGAGACATAG | GAACGTCAAG | TGGTAGCGGT | AGGAGGGAGT | TGGTTTAGTT | TTTTAGATAC | 720 |
| TAGGAGACAG | AACCGGACGG | GCCCATTGCA | AGGCCCAAGT | TGAAGTCCAG | CCGTGAATCA | 780 |
| ACAAAGAGAG | GGCCCATAAT | ACTGTCGATG | AGCATTTCCC | TATAATACAG | TTGCCTTCCA | 840 |
| CTAAGGGATA | GTTACCCGCA | ATTCTCTTGA | CACGTGTCAC | TGAAACCTGC | TACAAATAAG | 900 |
| GCAGGCACCT | CCTCATTGAC | ACTCACTCAC | TCACTCACTC | ACACAGCTCA | ACAAGTGGTA | 960 |
| ACTTTTACTC | ATCTCCTCCA | ATTATTTATG | ATTTCATGCA | TGTTTCCCTA | CATTCTATTA | 1020 |
| TGAATCGTGT | TATGGTGTAT | AAACGTTGTT | TCATATCTCA | TCTCATCTAT | TCTGATTTTG | 1080 |
| ATTCTCTTGC | CTACTGTAAT | CGGTAATAAA | TGTGAATGCT | TCCTCTTCTT | CTTCTTCTCA | 1140 |
| GAAATCAATT | TCTGTTTTGT | TTTTGTTCAT | CTGTAGCTTA | TTCTCTGGTA | GATTCCCCTT | 1200 |
| TTTGTAGACC | ACACATCACA | AGATCT | | | | 1226 |

( 2 ) INFORMATION FOR SEQ ID NO:27:

( i ) SEQUENCE CHARACTERISTICS:
    ( A ) LENGTH: 1478 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:27:

| | | | | | | |
|---|---|---|---|---|---|---|
| AGCCTTGTGT | TAGGGGGTAT | TCAAACCTTC | TTTGACTGAA | AATTTTATTA | TTTATACATG | 60 |
| TTTAAAATTA | CTTTTTAATC | TATATATAAT | AGATATCAAT | CCTTCATTTA | ATTGTATTTT | 120 |
| TGTATTAATT | CTATAAATAT | TAAATTACTT | TATTAAAAAT | TCTAATTCTG | TCACTCGTCA | 180 |
| TTTCATAATA | TTCTTGACGG | TGATGGTAGT | GATAATTACG | TTGATTGGAG | CCACATGGGC | 240 |
| CGCTACTTTT | TAAAAGGATG | AACCTTGGAA | TGTAGTGAAT | GTTGAGTCTC | ATAGCTCACT | 300 |
| CACGGACTCA | ACAGCAAAAT | CTGTCCTCTT | TTTCCCTTCT | CCAATTCACA | TACTGTCACT | 360 |
| TGGACAAATA | ATATTTGAAA | ATTTTGGCCT | AAAGTTAGGT | TTGGAGCCGT | ATGGTAATTT | 420 |
| GATACACAAA | TTATTATATA | ATTGATATAT | CAGGTATATA | TATCAAGTTG | TCGCTTCTTC | 480 |

| | | | | | |
|---|---|---|---|---|---|
| GTTCATTGTT | TCTCTCACTA | AAATTTTCAA | TTCACTTTTT | AAAAAATCGA | TAAATTTTTA | 540
| ATATAACTTT | ACATAACATA | TTCAAAATTA | CAAAATAAA | GGATATTTT | ATATGTTTAT | 600
| TTTTAATGTA | AGATTAAATA | TTTAGAATTC | TTTTTAAGAA | CGGTACAAGC | AAATTAAAAG | 660
| AGAGAAGGTA | TATTAGTGGG | CCTATGTATC | TTTGATATCA | TATGCCTCTC | AAAGAGCATC | 720
| CTGATGAGTC | TATATATCTT | TGTTGATAGT | GATTAACCA | TTTATGTATG | TACGTAGTAC | 780
| TAAGACATGT | TAAATAAGAT | CCTAGAGAAA | GATTTTGGA | AAAGTGAAAA | CAGCAATAAA | 840
| GAAAAGTCAT | TTAAACACTT | TCCAACAAAC | ATTTGGTAAT | CGATTTTAAT | TACCCACTTA | 900
| AACAAAACTA | TTTGTACGTA | AAATGTTTAA | GTAGAAAAGA | GATTTTTTA | AAAAAAAAA | 960
| GAAGGCAAGA | GGTCATATAT | CTGACCCTTC | CTTAAATCCC | CGCGTATAAC | ACTTCTTTT | 1020
| TTTTGTGTGT | GTATGTTCAG | GAACATTTGT | ATTTTCTATT | TGAAATTTCT | CATTAAGTCA | 1080
| AATTCGAAAT | CTTTTAAATA | ATGTAGAGAA | ATCTCATTAT | ATTAACAAT | CCCACTTGAT | 1140
| GAATTCCTAA | ACATTTTCTA | TAAAATAACA | CTAAATCTTT | AATTATACAT | ATTACATACC | 1200
| TAACTCAAGC | AATCTTGTCG | GAAAAATCAT | TAGAAAAGAA | TTGGAAATAG | GGAAATAAAT | 1260
| AGACATATTT | TGGTTAGTAT | CTTTGTCTAT | AAGAATGGGT | GTGTTAAAGA | GCTAGTGCCA | 1320
| TAGTGTACCA | TTCTATTGGT | AGCATTGGC | AAGAGTTATT | CCCTCTCTCC | ATACCAATGG | 1380
| AGAAGTTTAA | TCTTGCTAGA | GTCTTATTGT | TGCTTCTTCA | ACTTGGAACT | TTGTTCATTG | 1440
| CCCATGCATG | TCCTTATTGT | CCATATCCTC | CTTCCACC | | | 1478

(2) INFORMATION FOR SEQ ID NO:28:

( i ) SEQUENCE CHARACTERISTICS:
        ( A ) LENGTH: 450 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

| | | | | | |
|---|---|---|---|---|---|
| AAATAAATAT | TTCAAAGTAA | ATTGTTACTC | CCTCTATCCC | ATACTCTTTT | CTTTTTTAA | 60
| TCGATTTCTT | ACTCTAATTG | AACTATTGGA | GACAACTTAA | ATGTAAATTT | TTTTTTCTT | 120
| TATCAAAATG | ATTGGCTGCT | ATATAAATAT | CTAATGGTTA | TTATACATAA | ATTTTAATAT | 180
| TTTTTATAAA | AAAATATCGA | GCTAAATCAT | ATCGTTAAA | TATAGAGATG | TGTTATTTAT | 240
| TTAAAAATTA | ATTTTAAAAA | AGTGAATATT | GTAAATTAGG | ATGAAAGAGT | ATTATATTGG | 300
| TTGTCGCAGT | ATAAATACCC | TGCATGCCAT | TACATTGTT | CAATCATCTT | TGCAACGATT | 360
| TGTGTGCTTT | AGCTTCCTTA | CATAACATGG | CTTCTATAAC | TAAAGCCTCA | TTACTTATCC | 420
| TTTTCCTCTC | CTTGAATCTC | CTTTTCTTCG | | | | 450

(2) INFORMATION FOR SEQ ID NO:29:

( i ) SEQUENCE CHARACTERISTICS:
        ( A ) LENGTH: 2196 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

| | | | | | |
|---|---|---|---|---|---|
| ATCGATTATT | GGTTTATCGG | GTTTTGATCG | TTATCGGTTC | GGTTAACCG | TTAAAATTTG | 60
| ACACAAAAAT | AAAAATTGAA | AAGCACTTAG | AAACAAGGTG | ACAAACCTAA | TAAACCATGC | 120

```
ACATGAGTTC  ACAAGTTACA  TCTTGCTAAA  AAACAAACAC  TTTTACATTG  TAGAATAACC   180
AAGTGTCTGG  GACAACCAAA  AATGAAAGTA  GGAAACCAAA  CTCTAAGTCA  AGGACTTTAT   240
ATACAAAATG  GTATAACTAT  AATTATTTAA  TTTACTATTG  GGTTATCGGT  TAACCCGTTA   300
AGAACCGATA  ACCCGATAAC  AAAACAATC   AAAATCGTTA  TCAAAACCGC  TAAACTAATA   360
ACCCAATACT  GATAAACCAA  TAACTTTTTT  TTTATTCGGG  TTATCGGTTT  CAGTTCGGTT   420
TTGAACAATC  CTAGTGTCCT  AATTATTGTT  TTGAGAACCA  AGAAAACAAA  AACTGACGTC   480
GCAAATATTT  CAGTAAATAC  TTGTATATCT  CAGTGATAAT  TGATTTCCAA  GATGTATAAT   540
TATCATTTAC  GTAATAATAG  ATGGTTTCCG  AAACTTACGC  TTCCCTTTTT  TCTTTTGCAG   600
TCGTATGGAA  TAAAGTTGGA  TATGGAGGCA  TTCCCGGGCC  TTCAGGTGGA  AGAGACGGAG   660
CTGCTTCACA  AGGAGGGGGT  TGTTGTACTT  GAAATAGGC   ATTTATTCCG  TTCGCAAACC   720
TATCATGTTC  CTATGGTTGT  TTATTTGTAG  TTTGGTGTTC  TTAATATCGA  GTGTTCTTTA   780
GTTTGTTCCT  TTTAATGAAA  GGATAATATC  TCGTGCCAAA  AATAAGCAAA  TTCGGTACAT   840
AAAGACATTT  TTTTTCTTTC  GTGGATTTTC  TGTTTATGGA  GTTGTCAAAT  GTGGAATTTA   900
TTTCATAGCA  TGTGGAGTTT  CCTCCTCTCC  TTTTTCATGT  GCCCTTGGGC  CTTGCCTGTT   960
TCTTGCACCG  CAGTGTGCCA  GGGCAGTCGG  CAGATGGACA  TAAATGGCAC  ACCGCTCGGC  1020
TCGTGGAAAG  AGTATGGTCA  GTTTCATTGA  TAAGTATTTA  CTCGTATTCG  GCGTATACAT  1080
CAAGTTAATA  GAAAGTAAAC  ACATATGATA  TCATACATCC  ATTAGTTAAG  TATAAATGCC  1140
AACTTTTTAC  TTGAATCGCT  GAATAAATTT  ACTTACGATT  AATATTTAGT  TGTGTGTTCA  1200
AACATATCAT  GCATTATTTG  ATTAAGAATA  AATAAACGAT  GTGTAATTTG  AAAACCAATT  1260
AGAAAAGAAG  TATGACGGGA  TTGATGTTCT  GTGAAATCAC  TGGCAAATTG  AACGGACGAT  1320
GAAATTTGAT  CGTCATTTAA  ACATATCAAC  ATGGCTTTAG  TCATCATCAT  TATGTTATAA  1380
TTATTTTCTT  GAAACTTGAT  ACACCAACTC  TCATTGGGAA  AGTGACAGCA  TAATATAAAC  1440
TATAATATCA  ATCTGGCAAT  TTCGAATTAT  TCCAAATCTC  TTTTGTCATT  TCATTTCATC  1500
CCCTATGTCT  GCCTGCAAGT  ACCAATTATT  TAAATACAAA  AATCTTGATT  AAACAATTCA  1560
TTTTCTCACT  AATAATCACA  TTTAATAATA  AACGGTTCAT  ACACGTGCGT  CACCTTTTTT  1620
TCGATTTTCT  CTCAAGCGCA  TGTGATCATA  TCTAACTCTT  GTGCAAACAA  GTGAAATGAC  1680
GTCCATTAAT  AAATAATCTT  TTGAATACCT  GTTCATTTTA  ATTTATTTGG  ATTTGCTAAG  1740
GATTTTTTTT  AGTTTTGAG   ATTTTTTATA  ATTTTAAATT  AAAAAAAATA  AGTTAAATAT  1800
ATCGAAAATG  TCTTTTAATC  TTATTTTTGA  AAAAGATAAT  TAGCTCAAAC  AAATTAAAAT  1860
TGGTAACTAT  TTTTCGGAAA  AATAATGATT  CTTATTGTAC  ATTCTTTTTC  ATCGATTAGA  1920
TATTTTTTTT  AAGCTCAAGT  ACAAAAGTCA  TATTTCAATC  CCCAAAATAG  CCTCAATCAC  1980
AAGAAATGCT  TAAATCCCCA  AAATACCCTC  AATCACAAAA  AGTGTACCAA  TCATAACTAT  2040
GGTCCTCTGT  AAATTCCAAC  AAAATCAAGT  CTATAAAGTT  ACCCTTGATA  TCAGTACTAT  2100
AAAACCAAAA  ATCTCAGCTG  TAATTCAAGT  GCAATCACAC  TCTACCACAC  ACTCTCTAGT  2160
AGAGAAATCA  GTTGATAACA  AGCTTTGTTA  ACAATG                              2196
```

( 2 ) INFORMATION FOR SEQ ID NO:30:

( i ) SEQUENCE CHARACTERISTICS:
        ( A ) LENGTH: 226 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

| | | | | | |
|---|---|---|---|---|---|
| GAATCCATAC | GAGCTTTTAC | CCTTCTGTTC | CACACGAGAT | TTCTGTTCTC | GTTGAGCTCA | 60
| TCTTAGGACA | CCTGCGTTAT | CTTTTAACAG | ATGTGTCCGT | CCCCCAGCCA | AACTCCCACC | 120
| TGACAATGTC | TTCGCCCGGA | TCGGCCCGCG | AAGCAGCCTT | TGGGTCAGAA | AAGAGGGCAG | 180
| TGCCCGCTTC | GATTACGATA | GTAAATACGG | GTAAGTAGTG | TATTAC | | 226

( 2 ) INFORMATION FOR SEQ ID NO:31:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

| | | | | | |
|---|---|---|---|---|---|
| GGGGTTAAAT | GGTGAGATGG | AAGAGAGGTC | TTGGTGACCT | TACCTGGATT | TCTCGTGTTC | 60
| TGATTTGAAT | CAAGAAGATA | TCTTTGAAAG | ATACTTACAT | GACGGCAACA | ATGAGCTATG | 120
| GCTGGTATGG | TGTACATGCT | | | | | 140

( 2 ) INFORMATION FOR SEQ ID NO:32:

( i ) SEQUENCE CHARACTERISTICS:
        ( A ) LENGTH: 121 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

| | | | | | |
|---|---|---|---|---|---|
| CAAGCTACCG | TGTGCTGGAT | TAGTACTGAA | GCCCTCTAGT | CAGAATCCGG | GCTAGAGGCA | 60
| CGCATGCGTT | GCGCTCGCTT | GCGACCGAGT | AGGGCTGTCC | AGGCTCGTGT | GTGCTAGTGT | 120
| G | | | | | | 121

( 2 ) INFORMATION FOR SEQ ID NO:33:

( i ) SEQUENCE CHARACTERISTICS:
        ( A ) LENGTH: 185 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

| | | | | | |
|---|---|---|---|---|---|
| AAATATAGAT | ATGCCTTAGC | CAGGCTGTTT | CTTTTAATTT | ACGGCGTAAC | ACTAACCATA | 60
| TATGTAGCTG | CTAAAACATA | TAGTCTAGCT | AGAGNAGAAC | TTTGTTATTA | CTGGATTGCT | 120
| GAGGAGACAT | AAGAGGCATT | GTCTTACAGA | GCAAGCTTTC | ATTTGTGTAC | TACACACTTA | 180
| GCATG | | | | | | 185

( 2 ) INFORMATION FOR SEQ ID NO:34:

( i ) SEQUENCE CHARACTERISTICS:
        ( A ) LENGTH: 233 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

| | | | | | | |
|---|---|---|---|---|---|---|
| CTGGAAATAG | AATCAAACGA | GCTTTTACCC | TTCTGTTCCA | CGCGAGATTT | CTGTTCTGCT | 60 |
| TGAGCTCATC | TTAGGACACC | TGCGTTATCT | TTTAACAGAT | GTGCGTCCCA | GCCAAACTCC | 120 |
| CACCTGACAA | TGTCTCGCCC | GATCGCCCGC | GAGCAGCTTG | GGTCAAAAGA | GGGCAGTGCC | 180 |
| GTTCGATTAG | CATAGTAAAT | AGCTAAAGTA | GCGATTACTT | GCTTGCTCAC | TTA | 233 |

( 2 ) INFORMATION FOR SEQ ID NO:35:

( i ) SEQUENCE CHARACTERISTICS:
        ( A ) LENGTH: 186 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

| | | | | | | |
|---|---|---|---|---|---|---|
| CCGGAGCAAC | GAGCCCAGCA | GTGGAAGACT | CTTGAGAAAG | GCTTTAGTCA | CCGGTGTATC | 60 |
| CTATAGTCTA | CTCAAGTTTA | TGTCGAAGTA | TGCCAATGGT | GTAACGCCGT | CGACTTCTTG | 120 |
| GGAAAAGGAG | GGAAGAGTAC | TTTAATCTCT | GTTCGGAGAA | ATAGTGCTAC | GCGAGAGTGA | 180 |
| AGAAAC | | | | | | 186 |

( 2 ) INFORMATION FOR SEQ ID NO:36:

( i ) SEQUENCE CHARACTERISTICS:
        ( A ) LENGTH: 208 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

| | | | | | | |
|---|---|---|---|---|---|---|
| CCCTATTTAG | GGAGTGCAAT | AGAGACCTGA | GATCCGATGC | GAACAATCAG | TCGAAGGAGC | 60 |
| GGAGCTTAGA | GCCTTTACTT | TATGTAAAGC | GCACTCACTC | TAACGGCGTA | CCTTTTGCAT | 120 |
| GATGGGTCAG | CGAGGAATGG | GAACAGCGGC | TTAAAGCATT | AGGTGTAGGC | GCTTCCAGAG | 180 |
| GTGGAATCCT | TCTAGTTCTT | CCTATTAC | | | | 208 |

( 2 ) INFORMATION FOR SEQ ID NO:37:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

| | | | | | | |
|---|---|---|---|---|---|---|
| GGCATCTCGA | TGGGAAGATT | TCGTTCGTTG | ATCATTGTCG | ATCAGTTTTC | TTTTGGCAGG | 60 |
| ACGTGACACG | ACTTCACGTG | CATTGCATGG | TTTCTGGTTG | TTCGAGATCA | GACGGCGG | 118 |

( 2 ) INFORMATION FOR SEQ ID NO:38:

( i ) SEQUENCE CHARACTERISTICS:
        ( A ) LENGTH: 143 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

| ATTCGAATGC | GAACAGACCA | TAGTCGTACA | TTATTCTCTA | GCCAATCGAT | GTGCAGAGAC | 60 |
| ACACGAAGTA | ACGTCCTCCT | CCAAACGTTA | CTCTCTTGAT | TCACCTTGCA | TAATTCACAG | 120 |
| CTCTGCAGAT | GATGTATATC | GCT | | | | 143 |

( 2 ) INFORMATION FOR SEQ ID NO:39:

( i ) SEQUENCE CHARACTERISTICS:
    ( A ) LENGTH: 194 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:39:

| GGTTAGTTTG | GACACAGTTT | GAATGACCGT | GGGATTCAGA | GTGGATCTCT | CTGTCAACTT | 60 |
| CTCCAAGAGT | TCCTCTTTGT | ACTCTCTAGC | ACGACTCTCA | TTCTCGACAC | ACATGTGTGT | 120 |
| CTGGGGCTCA | GGCTCTTGAT | GCTTGCTCTG | CGCTCGTACT | CCTGAGTGCT | TGTCCTCACC | 180 |
| ACTGATAGAA | GTTT | | | | | 194 |

( 2 ) INFORMATION FOR SEQ ID NO:40:

( i ) SEQUENCE CHARACTERISTICS:
    ( A ) LENGTH: 120 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:40:

| GGCACAGACA | ATATTTTTGA | ATGGTCTACT | AAGTCCCTTT | AATGCGCGAA | CTGCATAGCC | 60 |
| CTAAAACATG | TCGCAAATTT | ATAAATAGCA | GCAACGCAGC | ACAAGCAGCA | GATAAAACAG | 120 |

( 2 ) INFORMATION FOR SEQ ID NO:41:

( i ) SEQUENCE CHARACTERISTICS:
    ( A ) LENGTH: 265 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:41:

| GTCGATTACA | ATTCACTGGC | CGACGTTTAC | AACGTCGTGA | CTGGGAAAAC | CCTGGCGTTA | 60 |
| CCCAACTTAA | TCGCCTTGCA | GCACATCCCC | CTTTCGCCAG | CTGGCGTAAT | AGCGAAGAGG | 120 |
| CCCGCACCGA | TCGCCCTTCC | AACAGTTGCG | CAGCCTGAAT | GGCGAATGGC | AAATTGTAAG | 180 |
| CGTTAATATT | TGTTAAATTC | GCGTTAAATT | TTGTTAAATC | AGCTCATTTT | ACAATAGCGA | 240 |
| ATCGCAAATC | TTATAAATCA | AAGAT | | | | 265 |

( 2 ) INFORMATION FOR SEQ ID NO:42:

( i ) SEQUENCE CHARACTERISTICS:
    ( A ) LENGTH: 232 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:42:

| CCTGTCGGCC | AGGCTATAGC | TCGTTGAATA | CTCAGTGTAG | CGCGCGTGCG | GCCCAGAACA | 60 |
| TCTAAGGGAC | TCACAGACCT | GTTATTGGCC | TCAAACTTCG | CGGCCTAAAA | GGCCGTAGTC | 120 |
| CTCTAAGAAG | CTGGCCGCGA | AGGGATACCT | CCGCATAGCT | AGTTAGCAGG | CTGAGGTCTG | 180 |
| TCGTAAGCAT | TACCAGACAA | ATGTCCACAA | CTAAGACGCA | TATCATCTAT | TA | 232 |

( 2 ) INFORMATION FOR SEQ ID NO:43:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

| GTTCTGAGAA | TCCAATTGTC | TCCCACAACT | TGTAGTATGA | TGATAATCTG | TACTCCCTGA | 60 |
| AGTTTATGAC | CAAGATGGCA | ATCGCTGAGG | ATTGGCTGAG | AGGTACATTA | TTAAGAATCT | 120 |
| CTCTGGGGCG | GGAGCGTAGT | ACTTGGACAA | TATTGAACTT | AAGTTCCAAG | C | 171 |

( 2 ) INFORMATION FOR SEQ ID NO:44:

( i ) SEQUENCE CHARACTERISTICS:
        ( A ) LENGTH: 189 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

| ATTGGCAATG | AGTACAATCT | AAAGGTCCCT | TAAGCAGGAT | CCATTGGAGG | GCAAGTCTGG | 60 |
| AGCCAGCAGC | CGCGTAATTC | CAGCTCCAAT | AGCGTATATT | TAAGTTGTTG | CAGTTAAAAG | 120 |
| CTGCTAGTTG | GACTTTGGGA | TGCGCCGGCC | GGTGCCGCCT | AGGTGTGCAC | CGTGCTCTCT | 180 |
| CCTTGCTGT | | | | | | 189 |

( 2 ) INFORMATION FOR SEQ ID NO:45:

( i ) SEQUENCE CHARACTERISTICS:
        ( A ) LENGTH: 200 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

| TGGGAGGCGT | GCTGCAATCC | CAACAATTGG | CAGTGTACTC | TAGTGAATAA | CGCTACTACG | 60 |
| GCGGCAAGGA | CACTCCTAAA | AGCTGCTGCA | ATGTATAGCC | TGTGTAGTTA | GGCGGCGGTG | 120 |
| TAAGTGGCAT | CAGGGCACAA | GATGAGCAAG | CTCTTAGTGG | TGCTGCTCAA | GCCACTGAAA | 180 |
| GAGCGACTTA | TCAATAGTAG | | | | | 200 |

( 2 ) INFORMATION FOR SEQ ID NO:46:

( i ) SEQUENCE CHARACTERISTICS:
        ( A ) LENGTH: 248 base pairs
        ( B ) TYPE: nucleic acid
        ( C ) STRANDEDNESS: single -continued ( D ) TOPOLOGY: linear ( i i ) MOLECULE TYPE: cDNA ( x i ) SEQUENCE DESCRIPTION: SEQ ID NO:46:

| GTTTGCCCAA | AGAGCGTATC | CCTTTTTCAT | AAGAGGTCTG | GGAAGCTTGT | GCCCACGAAG | 60 |
| TACAAAGCAA | GTACCTCAGT | AAGTCAAAGT | GCAACTTGAT | CAATGGGACT | GTGAGACAGA | 120 |
| GCCCAGACTT | TGACGAAAAT | AAAATTATGG | TATTCCTCAA | GTGCACGTGG | GACACAAAGG | 180 |
| TGGAAAACTA | GTCTACCCAA | GATTAAGCCA | GTCAAACCAT | AGACGCTTTT | ATCAGCAGAC | 240 |
| TGTAAATG | | | | | | 248 |

( 2 ) INFORMATION FOR SEQ ID NO:47:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

| GGCGTCGGCC | TTGCCTTGTT | GAAAGAACAA | AAGAGCAAAA | TTTGTTATNT | TCTATTTGTG | 60 |
| TGCCTTTTGT | TGGCTCCGGT | TTTTTGTCT | GGGATATCTG | ATGTGCACTT | AGTTTAAAC | 120 |
| AACATAAACA | TGCTAACACT | TTTTGTCAAA | AAA | | | 153 |

( 2 ) INFORMATION FOR SEQ ID NO:48:

( i ) SEQUENCE CHARACTERISTICS:
        ( A ) LENGTH: 224 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

| GGAGGTTGTG | CTGCGAATCC | CAACAATTGG | TAGTGTACTC | CTAGTGAATA | ACGCTACTAC | 60 |
| GGCGGCAAGG | GACACTCCTA | AAGCTGCTGC | AATGTATAGC | CCTGTGTAGT | TAGGCGCGTG | 120 |
| TAAGTGGCAT | CAGGGCACAA | GATGAGCAAG | CTCTTAGTGT | GCCTCGCTAA | GCACTGAAAG | 180 |
| CAGCTGCTAT | CAAAATCAGT | GGGCTATCTC | AGAGTACGAG | GACA | | 224 |

( 2 ) INFORMATION FOR SEQ ID NO:49:

( i ) SEQUENCE CHARACTERISTICS:
        ( A ) LENGTH: 215 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

| GGGTTAGAAG | GTTAGGCTAT | AGACGAAGAA | TACTCAAGTG | TGCGCGCTGC | GGCCCAGAAC | 60 |
| ATCTAAGGGC | ATCACAGACC | TGTTATTGCC | TCAAACTTCG | CGGCCTAAAA | GGCCGTAGTC | 120 |
| CTCTAAGAGC | TGGCCGCGAA | GGGATACCTC | GCATAGCTAG | TTAGCAGGCT | GAGTCTGTTC | 180 |
| GTACGATACC | AGACAAATGT | CACACTAGAC | GCATG | | | 215 |

( 2 ) INFORMATION FOR SEQ ID NO:50:

(i) SEQUENCE CHARACTERISTICS:
    (A) LENGTH: 239 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:50:

```
TTATAATGTG ACTTTTATAT ACCTTCATCA CATGATAAAA GAGAAACTAC TTACTGTGCC    60
TTTGTTATTT TTCATTCACT TCCCCTCTTA GTCTATTTCC ACAGCTTCAA TGTTCCAAAT   120
GTCTTTGGCA TATTCATGGA TTGTTCTGTC ACTGCTGAAC TTGTACGATC CCGCTGTATT   180
CAAGATTGAC ATCGTGTCAC TTTCTGGTCC GCGATATGCC TCATCGCTTT CTCTTTGCA    239
```

(2) INFORMATION FOR SEQ ID NO:51:

(i) SEQUENCE CHARACTERISTICS:
    (A) LENGTH: 170 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:51:

```
CCCTTCTGTC CACCACGAGA TTTCTGTTCT CGTTGAGCTC GTCTTAGGAC ACCTGCGTTA    60
TCTTTTAACA GATAGTGCCG CCCCAGCCCA AACTCCCCAC CTGACAATGT CTTCCGCCGG   120
ATCGGCCCGC GAAGCAGCCT TGGGTCAAAA GAGGGCAGTA CCGCTTGCAT             170
```